US009676676B2

(12) United States Patent
Hartung, Jr. et al.

(10) Patent No.: US 9,676,676 B2
(45) Date of Patent: Jun. 13, 2017

(54) SELECTIVE OLEFIN METATHESIS WITH CYCLOMETALATED RUTHENIUM COMPLEXES

(71) Applicant: CALIFORNIA INSTITUTE OF TECHNOLOGY, Pasadena, CA (US)

(72) Inventors: John Hartung, Jr., Evanston, IL (US); Brendan L. Quigley, Pasadena, CA (US); Peter K. Dornan, Pasadena, CA (US); Robert H. Grubbs, South Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 34 days.

(21) Appl. No.: 14/789,848

(22) Filed: Jul. 1, 2015

(65) Prior Publication Data

US 2016/0185684 A1 Jun. 30, 2016

Related U.S. Application Data

(60) Provisional application No. 62/137,091, filed on Mar. 23, 2015, provisional application No. 62/035,293, filed on Aug. 8, 2014, provisional application No. 62/023,666, filed on Jul. 11, 2014, provisional application No. 62/020,226, filed on Jul. 2, 2014.

(51) Int. Cl.
| | |
|---|---|
| *C07F 15/00* | (2006.01) |
| *C07B 37/02* | (2006.01) |
| *B01J 31/22* | (2006.01) |
| *C07C 67/293* | (2006.01) |
| *C07D 207/46* | (2006.01) |
| *C07F 7/18* | (2006.01) |
| *C07D 211/94* | (2006.01) |
| *C07D 471/04* | (2006.01) |
| *C07D 317/12* | (2006.01) |
| *C07C 6/04* | (2006.01) |
| *C07C 29/32* | (2006.01) |
| *C07C 67/343* | (2006.01) |
| *C07C 67/475* | (2006.01) |

(52) U.S. Cl.
CPC ........... *C07B 37/02* (2013.01); *B01J 31/2208* (2013.01); *B01J 31/2278* (2013.01); *C07C 6/04* (2013.01); *C07C 29/32* (2013.01); *C07C 67/293* (2013.01); *C07C 67/343* (2013.01); *C07C 67/475* (2013.01); *C07D 207/46* (2013.01); *C07D 211/94* (2013.01); *C07D 317/12* (2013.01); *C07D 471/04* (2013.01); *C07F 7/1892* (2013.01); *C07F 15/0046* (2013.01); *B01J 2231/54* (2013.01); *B01J 2231/543* (2013.01); *B01J 2531/821* (2013.01); *C07B 2200/09* (2013.01); *C07C 2101/08* (2013.01); *C07C 2101/14* (2013.01); *C07C 2102/08* (2013.01); *C07C 2531/22* (2013.01)

(58) Field of Classification Search
CPC .................................................. C07F 15/0046
See application file for complete search history.

(56) References Cited

U.S. PATENT DOCUMENTS 5,312,940 A    5/1994 Grubbs et al.

OTHER PUBLICATIONS

Keitz et al. "Improved Ruthenium Catalysts for Z-Selective Olefin Metathesis" Journal of the American Chemical Society, 2012, vol. 134, pp. 693-699.*
Seiders et al. "Enantioselective Ruthenium-Catalyzed Ring-Closing Metathesis" Organic Letters, 2001, vol. 3, pp. 3225-3228.*
Berlin et al., "Highly Active Chiral Ruthenium Catalysts for Asymmetric Cross- and Ring-Opening Cross-Metathesis," Angew. Chem. Int. Ed., 2006, 45, pp. 7591-7595 and supportive information.
Burke et al., "Desummetrization by Ring-Closing Metathesis Leading to 6,8-Dioxabicycle[3.2.1]octanes: A New Route for the Synthesis of (+)-exo- and endo-Brevicomin," Org. Lett., 1999, vol. 1, No. 11, pp. 1827-1829.
Costabile et a., "Origin of Enantioselectivity in the Asymmetric Ru-Catalyzed Metathesis of Olefins," J. Am. Chem. Soc., 2004, 126, pp. 9592-9600.
Endo et al., "Chelated Ruthenium Catalysts for Z-Selective Olefin Metathesis," J. Am. Chem. Soc., 2011, 133, pp. 8525-8527.
Funk et al., "Highly Active Chiral Ruthenium Catalysts for Asymmetric Ring-Closing Olefin Metathesis," J. Am. Chem. Soc., 2006, 128, pp. 1840-1846.
Greene et al., "Protective Groups in Organic Synthesis," Third Edition, 1999, John Wiley & Sons, Inc.
Hartung et al., "Catalytic, Enantioselective Synthesis of 1,2-anti Diols via Asymmetric Ring Opening/Cross Metathesis," NIH Author Manuscript, pp. 1-13.
Hartung et al., "Highly Z-Selective and Enantioselective Ring-Opening/Cross-Metatheis Catalyzed by a Resolved Stereogenic-at-Ru Complex," J. Am. Chem. Soc., 2013, 135, pp. 10183-10185 and supportive information.
Hartung et al., "Enantioselective Olefin Metathesis with Cyclometalated Ruthenium Complexes," J. Am. Chem. Soc., 2014, 136, pp. 12039-13037 and supportive information.
Herbert et al., "Decomposition Pathways of Z-Selective Ruthenium Metathesis Catalysts," J. Am. Chem. Soc., 2012, 134, pp. 7861-7866.

(Continued)

*Primary Examiner* — Joseph Kosack
(74) *Attorney, Agent, or Firm* — J.A. Lindeman & Co., PLLC

(57) ABSTRACT

This invention relates generally to C—H activated ruthenium olefin metathesis catalyst compounds which are stereogenic at the ruthenium center, to their preparation, and the use of such catalysts in the metathesis of olefins and olefin compounds. In particular, the invention relates to the use of C—H activated ruthenium olefin metathesis catalyst compounds in Z-selective olefin metathesis reactions, enantio-selective olefin metathesis reactions, and enantio-Z-selective olefin metathesis reactions. The invention has utility in the fields of catalysis, organic synthesis, polymer chemistry, and industrial and fine chemicals chemistry.

6 Claims, No Drawings

(56) References Cited

OTHER PUBLICATIONS

Amir H. Hoveyda, "Evolution of Catalytic Stereoselective Olefin Metathesis: From Ancillary Transformation to Purveyor of Stereochemical Identity," J. Org. Chem., 2014, 79, pp. 4763-4792.

Jafarpour et al., "Improved One-Pot Synthesis of Second-Generation Ruthenium Olefin Metathesis Catalysts," Organometallics, 2002, 21, pp. 442-444.

Kannenberg et al., "A Novel Ligand for the Enantioselective Ruthenium-Catalyzed Olefin Metathesis," Angew. Chem. Int. Ed., 2011, 50, pp. 3299-3302.

Keitz et al., "Z-Selective Homodimerization of Terminal Olefins with a Ruthenium Metathesis Catalyst," J. Am. Chem. Soc., 2011, 133, pp. 9686-9688.

Keitz et al., "Improved Ruthenium Catalysts for Z-Selective Olefin Metathesis," J. Am. Chem. Soc., 2012, 134, pp. 693-699.

Keitz et al., "Cis-Selective Ring-Opening Metathesis Polymerization with Ruthenium Catalysts," J. Am. Chem. Soc., 2012, 134, pp. 2040-2043.

Khan et al., "Z- and Enantioselective Ring-Opening/Cross-Metathesis with Enol Ethers Catalyzed by Stereogenic-at-Ru Carbenes: Reactivity, Selectivity, and Curtin-Hammett Kinetics," J. Am. Chem. Soc., 2012, 134, pp. 12774-12779.

La et al., "Catalytic Asymmetric Ring-Opening Metathesis/Cross Metathesis (AROM/CM) Reactions. Mechanism and Application to Enantioselective Synthesis of Functionalized Cyclopentanes," J. Am. Chem. Soc., 2001, 123, pp. 7767-7778.

Liu et al., "Z-Selectivity in Olefin Metathesis with Chelated Ru Catalysts: Computational Studies of Mechanism and Selectivity," J. Am. Chem. Soc., 2012, 134, pp. 1464-1467.

Pangborn et al., "Safe and Convenient Procedure for Solvent Purification," Organometallics, 1996, 15, pp. 1518-1520.

Paczal et al., "Modular Synthesis of Heterocyclic Carbene Precursors," J. Org. Chem., 2006, 71, pp. 5969-5979.

Ritter et al., "A Standard System of Characterization for Olefin Metathesis Catalysts," Organometallics, 2006, 25, pp. 5740-5745.

Rosebrugh et al., "Highlt Active Ruthenium Metathesis Catalysts Exhibiting Unprecedented Activity and Z-Selectivity," J. Am. Chem. Soc., 2013, 135, pp. 1276-1279 and supportive information.

Sattely et al., "Enantioselective Synthesis of Cyclic Amides and Amines through Mo-Catalyzed Asymmetric Ring-Closing Metathesis," J. Am. Chem. Soc., 2005, 127, pp. 8526-8533.

Savoie et al., "Improved Chiral Olefin Metathesis Catalysts: Increasing the Thermal and Solution Stability via Modification of a C1-Symmetrical N-Heterocyclic Carbene Ligand," Adv. Synth. Catal., 2009, 351, pp. 1826-1832.

Seiders et al., "Enantioselective Ruthenium-Catalyzed Ring-Closing Metathesis," Org. Lett., 2001, vol. 3, No. 20, pp. 3225-3228.

Stenne et al., "Desymmetrications Forming Tetrasubstituted Olefins Using Enantioselective Olefin Metathesis," Org. Lett., 2010, vol. 12, No. 9, pp. 2032-2035.

Tiede et al., "Highly Active Chiral Ruthenium-Based Metathesis Catalysts through a Monosubstitution in the N-Heterocyclic Carbene," Angew. Chem. Int. Ed., 2010, 49, pp. 3972-3975.

Van Veldhuizen et al., "A Recyclable Chiral Ru Catalyst for Enantioselective Olefin Metathesis. Efficient Catalytic Asymmetric Ring-Opnening/Cross Metathesis in Air," J. Am. Chem. Soc., 2002, 124, pp. 4954-4955.

Van Veldhuizen et al., "Chiral Ru-Based Complexes for Asymmetric Olefin Metathesis: Enhancement of Catalyst Activity through Steric and Electronic Modifications," J. Am. Chem. Soc., 2003, 125, pp. 12502-12508.

Van Veldhuizen et al., "A Readily Available Chiral Ag-Based N-Heterocyclic Carbene Complex for Use in Efficient and Highly Enantioselective Ru-Catalyzed Olefin Metathesis and Cu-Catalyzed Allylic Alkylation Reactions," J. Am. Chem. Soc., 2005, 127, pp. 6877-6882.

\* cited by examiner

SELECTIVE OLEFIN METATHESIS WITH CYCLOMETALATED RUTHENIUM COMPLEXES

CROSS REFERENCE TO RELATED APPLICATIONS

The present application claims the benefit of U.S. Provisional Patent Application No. 62/137,091, filed Mar. 23, 2015, of U.S. Provisional Patent Application No. 62/035,293, filed Aug. 8, 2014, of U.S. Provisional Patent Application No. 62/023,666, filed Jul. 11, 2014, and of U.S. Provisional Patent Application No. 62/020,226, filed Jul. 2, 2014, which are each incorporated herein by reference in their entirety.

STATEMENT OF FEDERAL SUPPORT

This invention was made with government support under GM031332 awarded by the National Institutes of Health and CHE1048404, CHE1212767, CHE1212797 awarded by the National Science Foundation. The government has certain rights in the invention.

TECHNICAL FIELD

This invention relates generally to C—H activated ruthenium olefin metathesis catalyst compounds which are stereogenic at ruthenium, to the preparation of such compounds, and the use of such catalysts in the metathesis of olefins and olefin compounds. In particular, the invention relates to the use of C—H activated ruthenium olefin metathesis catalyst compounds in Z-selective olefin metathesis reactions, enantio-selective olefin metathesis reactions, and enantio-Z-selective olefin metathesis reactions. The invention has utility in the fields of catalysis, organic synthesis, polymer chemistry, and industrial and fine chemicals chemistry.

BACKGROUND

Olefin metathesis is a powerful method for the construction of C=C bonds in a large number of synthetic contexts, including target oriented synthesis, (see *Metathesis in Natural Product Synthesis: Strategies, Substrates, and Catalysts*; 1st ed.; Cossy, J., Arseniyadis, S., Meyer, C., Eds.; Wiley-VCH: Weinheim, Germany, 2010. Nicolaou, K. C.; Bulger, P. G.; Sarlah, D. *Angew. Chem. Int. Ed.* 2005, 44, 4490-4527) polymer chemistry, (see *Handbook of Metathesis*; Grubbs, R., Ed.; Wiley-VCH: Weinheim, Germany, 2003; Sutthasupa, S.; Shiotsuki, M.; Sanda, F. *Polym. J.* 2010, 42, 905-915) and renewable feedstock derivatization (see Nickel, A.; Pedersen, R. L. In *Olefin Metathesis: Theory and Practice*; Grela, K., Ed.; Wiley-VCH: Weinheim, Germany, 2014). Extensive efforts have been made to design tailored catalysts for each application (see Vougioukalakis, G. C.; Grubbs, R. H. *Chem. Rev.* 2010, 110, 1746-1787). The development of asymmetric olefin metathesis catalysts has enabled the synthesis of enantioenriched compounds containing olefin functional groups, which are useful functional handles for further transformations. Generations of Mo- and Ru-based catalysts have been applied to asymmetric ring opening cross metathesis (AROCM), asymmetric ring closing metathesis (ARCM), asymmetric ring rearrangements (ARR) and asymmetric cross metathesis (ACM) to the synthesis of useful synthetic building blocks and natural products (Scheme 1) (see Stenne, B.; Collins, S. K. In *Olefin Metathesis: Theory and Practice*; Grela, K., Ed.; Wiley-VCH: Weinheim, Germany, 2014; Hoveyda, A. H.; Malcolmson, S. J.; Meek, S. J.; Zhugralin, A. R. *Angew. Chem. Int. Ed Engl.* 2010, 49, 34-44. Hoveyda, A. H. *J. Org. Chem.* 2014, 79, 4763-4792).

Scheme 1. Representative examples of the four manifolds of asymmetric olefin metathesis.

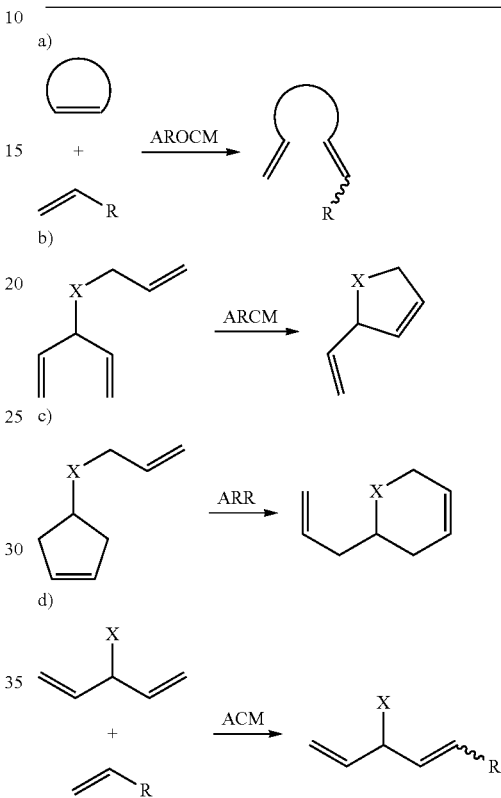

Despite progress in catalyst design, however, significant challenges remain. Controlling olefin geometry in AROCM and ACM while maintaining high enantioselectivity is difficult. Furthermore, ARCM of unhindered trienes has so far been unsuccessful, resulting in extremely low enantioselectivities.

The first chiral Ru-based catalyst 1 as shown in Scheme 2, (see Seiders, T. J.; Ward, D. W.; Grubbs, R. H. *Org. Lett.* 2001, 3, 3225-3228) possessed a $C_2$-symmetric NHC ligand with chiral centers on the backbone of the NHC and unsymmetrical N-aryl substituents. This chiral information was relayed to the metal center through a gearing effect (see Costabile, C.; Cavallo, L. *J. Am. Chem. Soc.* 2004, 126, 9592-9600). Complex 1 catalyzed desymmetrizing ARCM to afford dihydropyrans in high ee. It was found that substitution of chloride for iodide ligands resulted in higher ee but lower yield. The highest levels of enantioinduction were obtained on substrates with E-trisubstituted enantiotopic olefins; Z-trisubstituted or 1,1-disubstituted enantiotopic olefins reacted with much lower selectivity. Subsequent modifications of the N-aryl substituents resulted in a more selective catalyst 2 (see Funk, T. W.; Berlin, J. M.; Grubbs, R. H. *J. Am. Chem. Soc.* 2006, 128, 1840-1846) for ARCM and AROCM, although the latter transformation took place with poor E/Z selectivity (see Berlin, J. M.; Goldberg, S. D.; Grubbs, R. H. *Angew. Chem. Int. Ed.* 2006, 45, 7591-7595). C₁-symmetric NHC ligands employing a geared arene substituent have also been developed by Collins (see Fournier, P.-A.; Collins, S. K. *Organometallics* 2007, 26, 2945-2949, Fournier, P.-A.; Savoie, J.; Stenne, B.; Bedard, M.; Grandbois, A.; Collins, S. K. *Chem.-Eur. J.* 2008, 14, 8690-8695. Grandbois, A.; Collins, S. K. *Chem.-Eur. J.* 2008, 14, 9323-9329. Savoie, J.; Stenne, B.; Collins, S. K. *Adv. Synth. Catal.* 2009, 351, 1826-1832) and Blechert (see Tiede, S.; Berger, A.; Schlesiger, D.; Rost, D.; Lühl, A.; Blechert, S. *Angew. Chem. Int. Ed.* 2010, 49, 3972-3975; Kannenberg, A.; Rost, D.; Eibauer, S.; Tiede, S.; Blechert, S. *Angew. Chem. Int. Ed.* 2011, 50, 3299-3302). For example, C₁-symmetric catalyst 3 was capable of performing ARCM to generate tetrasubstituted olefins with good enantioselectivity (see Stenne, B.; Timperio, J.; Savoie, J.; Dudding, T.; Collins, S. K. *Org. Lett.* 2010, 12, 2032-2035).

Scheme 2. Selected Enantiopure Ru-based Olefin Metathesis Catalysts

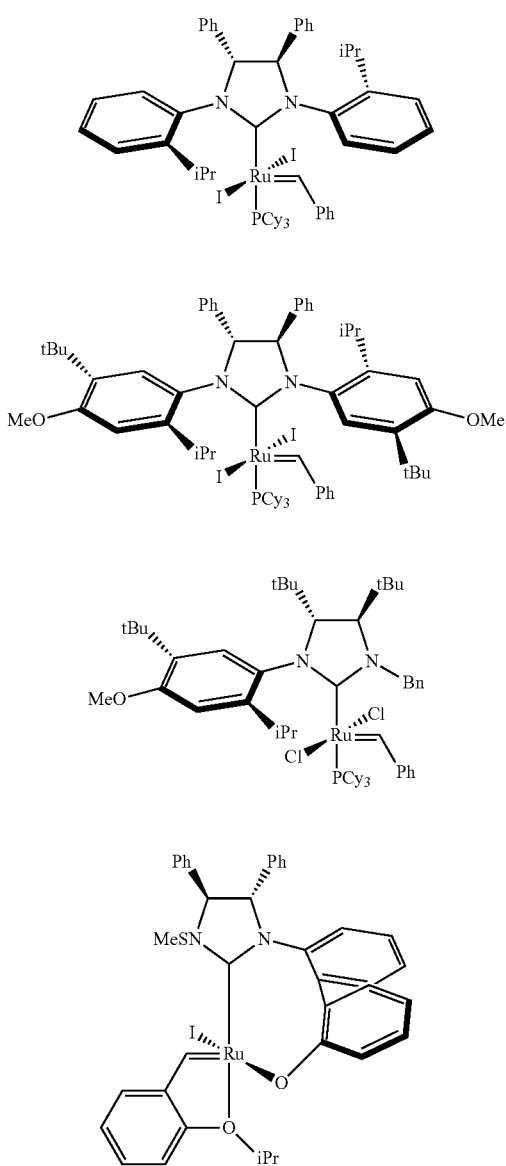

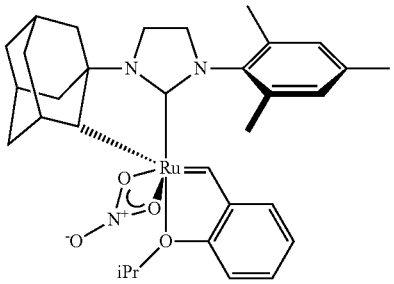

-continued

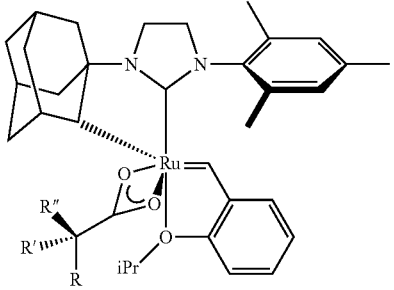

Hoveyda has developed stereogenic-at-Ru complexes bearing a binaphthyl aryloxide NHC substituent (see Van Veldhuizen, J. J.; Garber, S. B.; Kingsbury, J. S.; Hoveyda, A. H. *J. Am. Chem. Soc.* 2002, 124, 4954-4955, Van Veldhuizen, J. J.; Gillingham, D. G.; Garber, S. B.; Kataoka, O.; Hoveyda, A. H. *J. Am. Chem. Soc.* 2003, 125, 12502-12508). These complexes, which can be isolated as a single diastereomer, were used in E-selective AROCM and ARCM of trienes containing disubstituted enantiotopic olefins. Later a modified complex 4 containing NHC backbone chirality and a biphenyl aryloxide substituent was reported to have improved activity in E-selective AROCM of terminal olefins, (see Van Veldhuizen, J. J.; Campbell, J. E.; Giudici, R. E.; Hoveyda, A. H. *J. Am. Chem. Soc.* 2005, 127, 6877-6882) and to catalyze Z-selective AROCM with vinyl ethers and vinyl sulfides (see Khan, R. K. M.; O'Brien, R. V.; Torker, S.; Li, B.; Hoveyda, A. H. *J. Am. Chem. Soc.* 2012, 134, 12774-12779). Subsequent studies demonstrated that a higher energy diastereomer (differing in configuration at Ru) is accessible. These diastereomers can interconvert either through olefin metathesis, or a non-metathesis based polytopal rearrangement, thermal or Brønsted acid catalyzed, (see Khan, R. K. M.; Zhugralin, A. R.; Torker, S.; O'Brien, R. V.; Lombardi, P. J.; Hoveyda, A. H. *J. Am. Chem. Soc.* 2012, 134, 12438-12441, Torker, S.; Khan, R. K. M.; Hoveyda, A. H. *J. Am. Chem. Soc.* 2014, 136, 3439-3455).

Substantial progress has been made in the development of cyclometalated Ru complexes such as (rac)-5, which catalyze the Z-selective cross metathesis of terminal olefins (see Endo, K.; Grubbs, R. H. *J. Am. Chem. Soc.* 2011, 133, 8525-8527, Keitz, B. K.; Endo, K.; Herbert, M. B.; Grubbs, R. H. *J. Am. Chem. Soc.* 2011, 133, 9686-9688, Herbert, M. B.; Lan, Y.; Keitz, B. K.; Liu, P.; Endo, K.; Day, M. W.; Houk, K. N.; Grubbs, R. H. *J. Am. Chem. Soc.* 2012, 134, 7861-7866, Keitz, B. K.; Endo, K.; Patel, P. R.; Herbert, M. B.; Grubbs, R. H. *J. Am. Chem. Soc.* 2012, 134, 693-699, Quigley, B. L.; Grubbs, R. H. *Chem. Sci.* 2013, 5, 501-506, Rosebrugh, L. E.; Herbert, M. B.; Marx, V. M.; Keitz, B. K.; Grubbs, R. H. *J. Am. Chem. Soc.* 2013, 135, 1276-1279).

Despite the advances achieved in the art, a continuing need exists for further improvements in the areas of Asymmetric Ring Opening Cross Metathesis (AROCM), Asymmetric Ring Closing Metathesis (ARCM), and Asymmetric Cross Metathesis (ACM). The present invention is directed to addressing one or more of those concerns.

BRIEF SUMMARY OF THE DISCLOSURE

The success of enantioselective olefin metathesis relies on the design of enantioenriched alkylidene complexes capable of transferring stereochemical information from the catalyst structure to the reactants. Cyclometalation of the N-heterocyclic carbene ("NHC") ligand has proven to be a successful strategy to incorporate stereogenic atoms into the catalyst structure. Enantioenriched complexes incorporating this design element catalyze highly enantio-Z-selective asymmetric ring opening/cross metathesis of norbornenes and cyclobutenes, and the difference in ring strain between these two substrates leads to different propagating species in the catalytic cycle. Asymmetric ring closing metathesis of a selectivity is also analyzed leading to identification of nitrate 5 as the optimal catalyst for desymmetrizing transformations.

These complexes could also be used as highly enantioselective catalysts in asymmetric metathesis. A mechanistic proposal has been developed based on the preference of these complexes to react through side-bound metallacyclobutanes (syn to the NHC). This orientation forces all substituents in the forming metallacyclobutane to point away from the NHC N-aryl group, thus favoring the formation of the Z-olefin product (see Liu, P.; Xu, X.; Dong, X.; Keitz, B. K.; Herbert, M. B.; Grubbs, R. H.; Houk, K. N. *J. Am. Chem. Soc.* 2012, 134, 1464-1467). Recently, it has been shown that (rac)-5 can be resolved to generate enantioenriched 5 (Scheme 3). Complex 5 performs enantio- and Z-selective AROCM of norbornenes (see Hartung, J.; Grubbs, R. H. *J. Am. Chem. Soc.* 2013, 135, 10183-10185) and of cyclobutenes (see Hartung, J.; Grubbs, R. H. *Angew. Chem. Int. Ed.* 2014, 53, 3885-3888).

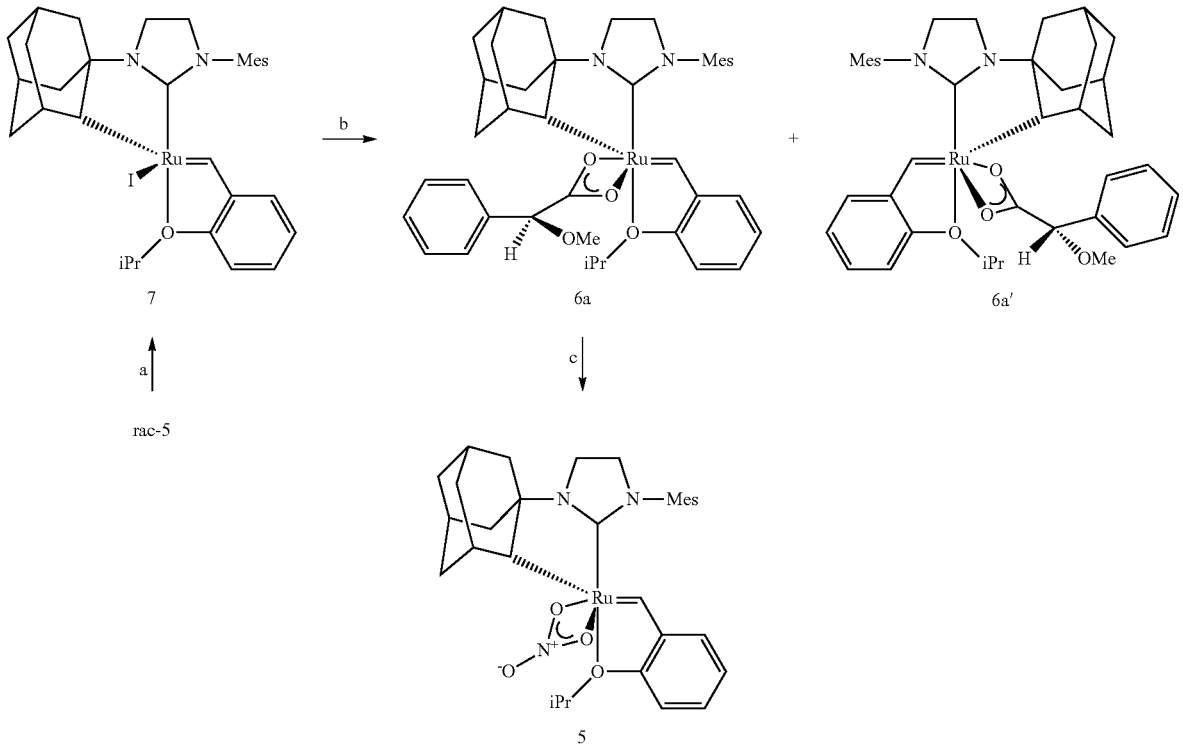

(a). a NaI, THF, 75% yield; b (S)-AgO$_2$CCH(Ph)(OMe) (8) (2 equiv), THF, 23° C., 1.5 h, 97%; c (1) 6a, pTsOH•H$_2$O, THF, 5 min; (2) NaNO$_3$, THF/MeOH, 15 min, 43%.

challenging class of prochiral trienes has also been achieved. The extent of reversibility and effect of reaction setup was also demonstrated. Finally, promising levels of enantioselectivity in an unprecedented Z-selective asymmetric cross metathesis of a prochiral 1,4-diene was demonstrated.

Synthetic and mechanistic studies involving cyclometalated Ru-complexes 5 and 6 in Z-selective AROCM are disclosed herein. Furthermore, these complexes are shown to provide promising levels of enantioinduction in two previously challenging transformations: ACM of prochiral dienes and ARCM of trienes composed of terminal olefins. The impact of X-type ligand substitution on reactivity and Resolution of (rac)-5 was accomplished by ligand exchange of nitrate for iodide, which facilitated a second exchange with enantiopure silver carboxylate 8 (Scheme 3). Attempted exchange with several other carboxylates was unsuccessful, for example reaction with the silver salts of α-methoxy-α-(trifluoromethyl)phenyl acid, N-acetyl tert-leucine, or N-acetyl phenylglycine resulted in rapid decomposition. The mandelate-derived diastereomers 6a and 6a' were chromatographically separable (under N$_2$ atmosphere), to afford a 45% yield (90% of theoretical) of diastereomer 6a (>95:5 dr) (see Hartung, J.; Grubbs, R. H. *J. Am. Chem. Soc.* 2013, 135, 10183-10185). A more rapid, but lower yielding route was discovered wherein trituration of the mixture of 6a and 6a' with 1:1 $Et_2O$/pentane resulted in the isolation of pure 6a (ranging from 49% to 77% of theoretical) due to the large difference in solubility between the diastereomers. The latter procedure is a marked improvement in the speed at which synthetically useful quantities of enantioenriched 5 can be produced. Waste is avoided by the easy recyclability of the washes containing the partially enriched diastereomeric mixture.

The invention is directed to addressing one or more of the aforementioned concerns, and, in one embodiment, provides an enantioenriched C—H activated catalyst compound composed of a Group 8 transition metal complex and a chelating ligand structure formed from the metal center M, a neutral electron donor ligand $L^1$, and a 2-electron anionic donor bridging moiety, Q*.

A general structure of catalyst compounds according to the invention is shown below, in Formula (I).

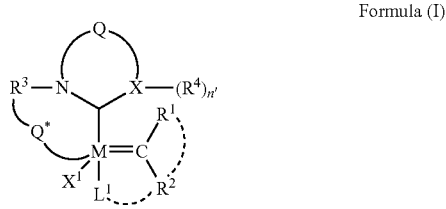

Formula (I)

wherein, M is a Group 8 transition metal (e.g., Ru or Os); $X^1$ is an anionic ligand; $L^1$ is a neutral two electron ligand, where $L^1$ may connect with $R^2$; $R^1$ and $R^2$ are independently selected from hydrogen, hydrocarbyl, substituted hydrocarbyl, heteroatom-containing hydrocarbyl, substituted heteroatom-containing hydrocarbyl, and functional groups, and wherein $R^1$ may connect with $R^2$ and/or $L^1$; Q* is a 2-electron anionic donor bridging moiety (e.g., alkyl, aryl, carboxylate, alkoxy, aryloxy, or sulfonate, etc.).

Enantiopure versions of these catalysts enable Asymmetric Ring Opening Cross Metathesis reactions, Asymmetric Ring Closing Metathesis reactions, and Asymmetric Cross Metathesis reactions.

Furthermore, enantioenriched versions of these catalysts also enable Asymmetric Ring Opening Cross Metathesis reactions, Asymmetric Ring Closing Metathesis reactions, and Asymmetric Cross Metathesis reactions.

Furthermore, racemic mixtures of these catalysts also enable Asymmetric Ring Opening Cross Metathesis reactions, Asymmetric Ring Closing Metathesis reactions, and Asymmetric Cross Metathesis reactions.

In another aspect, this invention describes a series of new ruthenium-based Z-selective olefin metathesis catalysts, which have an aryl substituent that is functionalized with one or more heteroatom or heteroatom-containing substituents. These differ from many of the earlier disclosed catalysts, which have aryl groups containing hydrogen or carbon-based substituents. A number of these catalysts display unique behaviour in solution, as a result of interactions involving these heteroaromatic substituents, which have not been observed in other classes of metathesis catalysts. In addition, these catalysts allow systematic and significant variation of the electronic and steric nature of the aryl group, aiding in clarifying the structure-activity and structure-selectivity relationships in the broader class of catalysts.

A number of these catalysts have been shown to promote Z-selective metathesis for one or more substrates. In these reactions, the nature of the substituents is demonstrated to affect both the activity and selectivity of the catalyst. Some of these catalysts are among the most Z-selective Ru-based metathesis catalysts disclosed to date in cross metathesis applications. While there are a number of previously reported Z-selective catalysts, there is always a need for more catalysts with improved activity, stability and selectivity. There are a wide variety of olefin metathesis transformations which are carried out under distinct experimental conditions and the efficiency of catalysts across this series of reactions and conditions is not uniform. Hence, it is advantageous to have a wide variety of catalysts with different reactivity profiles. These catalysts display different reactivity profiles to previous Z-selective metathesis catalysts.

DETAILED DESCRIPTION OF THE DISCLOSURE

Terminology and Definitions

Unless otherwise indicated, the invention is not limited to specific reactants, substituents, catalysts, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl (Me), ethyl (Et), n-propyl (Pr or n-Pr), isopropyl (i-Pr), n-butyl (Bu or n-Bu), isobutyl (i-Bu), t-butyl (t-Bu), octyl (Oct), decyl, and the like, as well as cycloalkyl groups such as cyclopentyl (Cp), cyclohexyl (Cy) and the like. Generally, although again not necessarily, alkyl groups herein contain 1 to about 12 carbon atoms. The term "lower alkyl" refers to an alkyl group of 1 to 6 carbon atoms, and the specific term "cycloalkyl" refers to a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" refers to an alkenyl group of 2 to 6 carbon atoms, and the specific term "cycloalkenyl" refers to a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a difunctional alkynyl group, where "alkynyl" is as defined above.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl (Ph), naphthyl, biphenyl, diphenylether, diphenylamine, benzophenone, and the like. "Substituted aryl" refers to an aryl moiety substituted with one or more substituent groups, and the terms "heteroatom containing aryl" and "heteroaryl" refer to aryl substituents in which at least one carbon atom is replaced with a heteroatom, as will be described in further detail herein.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, or (CO)-alkynyl wherein "alkyl," "aryl," "aralkyl," "alkaryl," "alkenyl," and "alkynyl" are as defined above. The acetoxy group (—O(CO)CH$_3$; often abbreviated as —OAc) is a common example of an acyloxy group.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" and "halide" are used in the conventional sense to refer to a fluoro, chloro, bromo, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, alkynyl groups, aryl groups, and the like. The term "lower hydrocarbyl" refers to a hydrocarbyl group of 1 to 6 carbon atoms, preferably 1 to 4 carbon atoms, and the term "hydrocarbylene" refers to a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

The term "heterocyclic carbene" refers to a neutral electron donor ligand comprising a carbene molecule, where the carbenic carbon atom is contained within a cyclic structure and where the cyclic structure also contains at least one heteroatom. Examples of heterocyclic carbenes include "N-heterocyclic carbenes" wherein the heteroatom is nitrogen and "P-heterocyclic carbenes" wherein the heteroatom is phosphorus.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—$C_6$-$C_{24}$, carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl) ($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino ((—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where, R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^{--}$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H)alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R includes without limitation alkyl or other hydrocarbyl), phosphono (—P(O)(OH)$_2$), phosphonato (—P(O)(O$^{--}$)$_2$), phosphinato (—P(O)(O$^{--}$)), phospho (—PO$_2$), phosphino (—PH$_2$), silyl (—SiR$_3$ wherein R is hydrogen or hydrocarbyl), and syloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above mentioned hydrocarbyl moieties may be further substituted with one or more functional groups or additional hydrocarbyl moieties such as those specifically mentioned above. Analogously, the above-mentioned hydrocarbyl moieties may be further substituted with one or more functional groups or additional hydrocarbyl moieties as noted above.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "internal olefin" as used herein means an olefin wherein each of the olefinic carbons is substituted by at least one non-hydrogen substituent. The internal olefin may be di-substituted, tri-substituted, or tetra-substituted.

The term "terminal olefin" as used herein means an olefin wherein one of the olefinic carbons is substituted by at least one non-hydrogen substituent. The terminal olefin may be di-substituted or mono-substituted.

The term "reactant internal olefin" as used herein means an internal olefin present in an olefin compound used in a cross-metathesis reaction with another olefin compound to form a cross-metathesis product. The "reactant internal olefin" may be di-substituted, tri-substituted, or tetra-substituted. The "reactant internal olefin" may have an E-configuration or a Z-configuration. The term "reactant terminal olefin" as used herein means a terminal olefin present in an olefin compound used in a cross-metathesis reaction with another olefin compound.

The term "product internal olefin" as used herein means an internal olefin present in a crossmetathesis product formed by a cross-metathesis reaction, wherein each of the olefinic carbons of the internal olefin is substituted by at least one non-hydrogen substituent. The "product internal olefin" may be di-substituted, tri-substituted, or tetra-substituted. The "product internal olefin" may have an E configuration or a Z-configuration. Preferably the "product internal olefin" has a Z-configuration.

The term "enantiomeric excess" (ee), as used herein, is a measurement of purity used for chiral substances. It reflects the degree to which a sample contains one enantiomer in greater amounts than the other. A racemic mixture has an ee of 0%, while a single completely pure enantiomer has an ee of 100%.

The term "enantioenriched," as used herein, refers to mirror images, when one chiral center is present or when 2 or more chiral centers are present and the enantiomeric or diastereomeric ratio is greater than 50:50 but less than 100:1.

The term "enantiopure," as used herein, refers to mirror images, when one chiral center is present or when 2 or more chiral centers are present and the enantiomeric or diastereomeric ratio is greater than 95%.

The term "C—H activated" refers to the cleavage of a carbon-hydrogen (C—H) bond of a ligand by the metal in a transition metal complex to form a resultant transition metal complex having a metal-carbon (M-C) bond. This reaction type is also called cyclometallation. See C. Elschenbroich in "Organometallics" 1989 VCH page 439; *ACS Symposium Series*, Vol. 485 "Organometallic CH Bond Activation: An Introduction" A. Goldman and K. Goldberg, publication date Jul. 12, 2004, Copyright © 2004 American Chemical Society; and Janowicz, A. H. & Bergman, R. G. *J. Am. Chem. Soc.* 1982, 104, 352-354.

The term "nil," as used herein, means absent or nonexistant.

Functional groups may be protected in cases where the functional group interferes with the metathesis catalyst, and any of the protecting groups commonly used in the art may be employed. Acceptable protecting groups may be found, for example, in Greene et al., Protective Groups in Organic Synthesis, 3rd Ed. (New York: Wiley, 1999). Examples of protecting groups include acetals, cyclic acetals, boronate esters (boronates), cyclic boronate esters (cyclic boronates), carbonates, or the like. Examples of protecting groups include cyclic acetals or cyclic boronate esters.

Catalyst Complexes

In general, the catalyst complexes of the invention comprise a Group 8 metal (M), an alkylidene moiety ($=CR^1R^2$), an anionic ligand ($X^1$), a neutral ligand ($L^1$) and a heterocyclic carbene ligand that is linked to the metal via a 2-electron anionic donor bridging moiety ($Q^*$). The olefin metathesis catalyst complex is preferably a Group 8 transition metal complex represented by the structure of Formula (I):

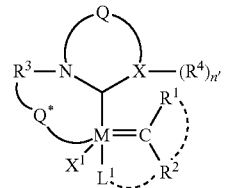

Formula (I)

wherein, M is a Group 8 transition metal (e.g., Ru or Os); $X^1$ is an anionic ligand; $L^1$ is a neutral two electron ligand, where $L^1$ may connect with $R^2$; $R^1$ and $R^2$ are independently selected from hydrogen, hydrocarbyl, substituted hydrocarbyl, heteroatom-containing hydrocarbyl, substituted heteroatom-containing hydrocarbyl, and functional groups, and wherein $R^1$ may connect with $R^2$ and/or $L^1$; $Q^*$ is a 2-electron anionic donor bridging moiety (e.g., alkyl, aryl, carboxylate, alkoxy, aryloxy, or sulfonate, etc.); $R^3$ and $R^4$ are independently selected from hydrocarbyl, substituted hydrocarbyl, heteroatom-containing hydrocarbyl, and substituted heteroatom-containing hydrocarbyl; X is an atom selected from C, N, O, S, and P, since O and S are divalent, n' is necessarily zero when X is O or S, similarly, when X is N or P, then n' is 1, and when X is C, then n' is 2.

In another aspect, the catalyst complexes of the invention comprise a Group 8 metal (M), preferably Ru, an alkylidene moiety ($=CR^1R^2$), an anionic ligand ($X^1$), a neutral ligand ($L^1$) and a heterocyclic carbene ligand that is linked to the metal via a 2-electron anionic donor bridging moiety ($Q^*$), and can be represented by the structure of Formula (II):

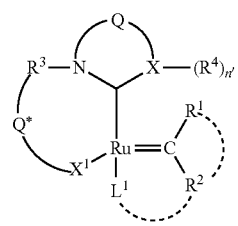

Formula (II)

in which:

$L^1$ is a neutral electron donor ligand;

$Q^*$ is a 2-electron anionic donor bridging moiety linking $R^3$ and Ru; and may be hydrocarbylene (including substituted hydrocarbylene, heteroatom-containing hydrocarbylene, and substituted heteroatom-containing hydrocarbylene, such as substituted and/or heteroatom-containing alkylene) or —(CO)—;

Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage;

X is an atom selected from C, N, O, S, and P. Since O and S are divalent, n' is necessarily zero when X is O or S. Similarly, when X is N or P, then n' is 1, and when X is C, then n' is 2;

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

$R^3$ and $R^4$ are independently selected from hydrocarbyl, substituted hydrocarbyl, heteroatom-containing hydrocarbyl, and substituted heteroatom-containing, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups.

$X^1$ is a bidentate anionic ligand. Typically, $X^1$ is nitrate, $C_1$-$C_{20}$ alkylcarboxylate, $C_6$-$C_{24}$ arylcarboxylate, $C_2$-$C_{24}$ acyloxy, $C_1$-$C_{20}$ alkylsulfonato, $C_5$-$C_{24}$ arylsulfonato, $C_1$-$C_{20}$ alkyl sulfanyl, $C_5$-$C_{24}$ arylsulfanyl, $C_1$-$C_{20}$ alkylsulfinyl, or $C_5$-$C_{24}$ arylsulfinyl. In some embodiments, $X^1$ is benzoate, pivalate, nitrate, an N-acetyl amino carboxylate, O-methyl mandelate, or a carboxylate derived from 2-phenylbutyric acid. More specifically, $X^1$ may be is $CF_3CO_2$, $CH_3CO_2$, $CH_3CH_2CO_2$, $CFH_2CO_2$, $(CH_3)_3CO_2$, $(CH_3)_2CHCO_2$, $(CF_3)_2(CH_3)CO_2$, $(CF_3)(CH_3)_2CO_2$, benzoate, naphthylate, tosylate, mesylate, or trifluoromethanesulfonate. In one more preferred embodiment, $X^1$ is nitrate ($NO_3^-$).

In certain catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, and phenyl. Most preferably, $R^2$ is phenyl or vinyl substituted with one or more moieties selected from methyl, ethyl, chloro, bromo, iodo, fluoro, nitro, dimethylamino, methyl, methoxy, and phenyl. More specifically, $R^2$ may be phenyl or —CH=C(CH$_3$)$_2$.

Any two or more (typically two, three, or four) of $X^1$, $L^1$, $R^1$, and $R^2$ can be taken together to form a cyclic group, including bidentate or multidentate ligands, as disclosed, for example, in U.S. Pat. No. 5,312,940 to Grubbs et al. When any of $X^1$, $L^1$, $R^1$, and $R^2$ are linked to form cyclic groups, those cyclic groups may contain 4 to 12, preferably 4, 5, 6, 7 or 8 atoms, or may comprise two or three of such rings, which may be either fused or linked.

In particular embodiments, Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of suitable functional groups include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers.

In more particular aspects, $R^3$ and $R^4$ maybe alkyl or aryl, and may be independently selected from alkyl, aryl, cycloalkyl, heteroalkyl, alkenyl, alkynyl, and halo or halogen-containing groups. More specifically, $R^3$ and $R^4$ may be independently selected from $C_1$-$C_{20}$ alkyl, $C_5$-$C_{14}$ cycloalkyl, $C_1$-$C_{20}$ heteroalkyl, or halide. Suitable alkyl groups include, without limitation, methyl, ethyl, n-propyl, isopropyl, isopropyl, n-butyl, isobutyl, t-butyl, octyl, decyl, and the like; suitable cycloalkyl groups include cyclopentyl, cyclohexyl, adamantyl, pinenyl, terpenes and terpenoid derivatives and the like; suitable alkenyl groups include ethenyl, n-propenyl, isopropenyl, n-butenyl, isobutenyl, octenyl, decenyl, tetradecenyl, hexadecenyl, eicosenyl, tetracosenyl, and the like; suitable alkynyl groups include ethynyl, n-propynyl, and the like.

When $R^3$ or $R^4$ are aromatic, each can be independently composed of one or two aromatic rings, which may or may not be substituted, e.g., $R^3$ and $R^4$ may be phenyl, substituted phenyl, biphenyl, substituted biphenyl, or the like. In a particular embodiment, $R^3$ and $R^4$ are independently an unsubstituted phenyl or phenyl substituted with up to three substituents selected from $C_1$-$C_{20}$ alkyl, $C_1$-$C_{20}$ alkylcarboxylate, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen $C_1$-$C_{12}$ alkyl, $C_1$-$C_{12}$ alkoxy, $C_5$-$C_{14}$ aryl, substituted, $C_5$-$C_{14}$ aryl, or halide. More particularly, $R^3$ and $R^4$ may be independently substituted with hydrogen, $C_1$-$C_4$ alkyl, $C_1$-$C_4$ alkylcarboxylate, $C_1$-$C_4$ alkoxy, $C_5$-$C_{14}$ aryl, substituted $C_5$-$C_{14}$ aryl, or halide. As an example, $R^3$ and $R^4$ are selected from cyclopentyl, cyclohexyl, adamantyl, norbonenyl, pinenyl, terpenes and terpenoid derivatives, mesityl, diisopropylphenyl or, more generally, cycloalkyl substituted with one, two or three $C_1$-$C_4$ alkyl or $C_1$-$C_4$ alkoxy groups, or a combination thereof.

In another embodiment, the olefin metathesis catalyst, that may be used in the invention disclosed herein, may be represented by the structure of Formula (IIa):

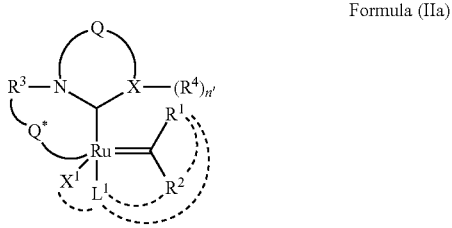

Formula (IIa)

wherein: $L^1$, $Q^*$, Q, X, $R^1$, $R^2$, $R^3$, $R^4$, n' and X are as defined previously for Formula (II), and wherein $R^1$ may connect with $R^2$, or $R^1$ may connect to $L^1$, or $R^2$ may connect to $L^1$, or $L^1$ may connect to $X^1$, to form cyclic groups, these cyclic groups may contain 4 to 12, preferably 4, 5, 6, 7 or 8 atoms, or may comprise two or three of such rings, which may be either fused or linked.

Particular complexes wherein $R^2$ and $L^1$ are linked to form a chelating carbene ligand are examples of another group of catalysts, and are commonly called "Grubbs-Hoveyda" catalysts. Grubbs-Hoveyda metathesis-active metal carbene complexes of the invention may be described by the Formula (III):

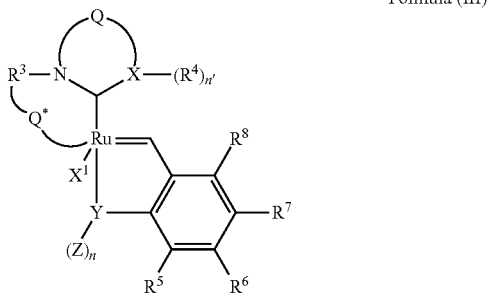

Formula (III)

wherein,

X, $X^1$, Q, $Q^*$, $R^3$, $R^4$ and n' are as previously defined herein;

Y is a heteroatom selected from N, O, S, and P; preferably Y is O or N;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^5$, $R^6$, $R^7$, and $R^8$ can be linked to form one or more cyclic groups;

n is 1 or 2, such that n is 1 when Y is the divalent heteroatoms O or S, and n is 2 when Y is the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, $Q^*$, Y, Z, $R^5$, $R^6$, $R^7$, and $R^8$ are linked to a support.

In another embodiment, the olefin metathesis catalyst complexes of the invention are C—H activated catalyst complexes having the structure of Formula (IV):

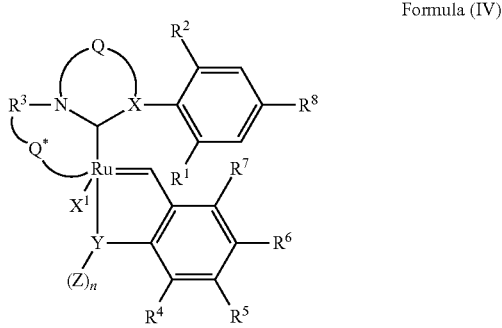

Formula (IV)

wherein, $R^1$ is $C_1$-$C_6$ alkyl, substituted $C_1$-$C_6$ alkyl, $C_5$-$C_8$ cycloalkyl, $C_5$-$C_8$ substituted cycloalkyl, $C_1$-$C_6$ alkoxy, or halide, where the substituents are selected from $C_1$-$C_6$ alkyl, $C_1$-$C_6$ alkoxy, or halide; in other embodiments $R^1$ is $C_1$-$C_6$ alkyl, or F; in other embodiments $R^1$ is $C_1$-$C_3$ alkyl, $C_1$-$C_3$ alkoxy, or F; in other embodiments $R^1$ is $C_1$-$C_4$ alkyl or F; in other embodiments $R^1$ is $C_1$-$C_3$ alkyl or F; in other embodiments $R^1$ is $OCH_3$ (i.e., OMe);

$R^2$ is heteroatom-containing hydrocarbyl, or substituted heteroatom-containing hydrocarbyl, where the substituents are selected from $C_1$-$C_6$ alkyl, $C_1$-$C_6$ alkoxy, or halide; in other embodiments $R^2$ is $C_1$-$C_6$ alkoxy; in other embodiments $R^2$ is $C_1$-$C_4$ alkoxy; in other embodiments $R^2$ is $C_1$-$C_3$ alkoxy; in other embodiments $R^2$ is $OCH_3$ (i.e., OMe);

$R^8$ is selected from hydrogen, $C_1$-$C_{10}$ alkyl, substituted $C_1$-$C_{10}$ alkyl, $C_5$-$C_{10}$ aryl, substituted $C_5$-$C_{10}$ aryl, $C_5$-$C_{10}$ heteroaryl, substituted $C_5$-$C_{10}$ heteroaryl, halide (—Cl, —F, —Br, —I), hydroxyl, $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, $C_5$-$C_{10}$ aryl, $C_5$-$C_{10}$ heteroaryl, halide (—Cl, —F, —Br, —I), $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), carboxylic acid (—COOH), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), cyano (—CN), where $R^9$ is hydrogen, methyl, $C_2$-$C_6$ alkyl; Q* is a 2-electron anionic donor bridging moiety linking $R^3$ and Ru; and may be hydrocarbylene (including substituted hydrocarbylene, heteroatom-containing hydrocarbylene, and substituted heteroatom-containing hydrocarbylene, such as substituted and/or heteroatom-containing alkylene) or —(CO)—;

Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage. In particular embodiments, Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of suitable functional groups include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers;

X is an atom selected from C, N, and P; in one embodiment X is an atom selected from N;

$R^3$ is independently selected from hydrocarbyl, substituted hydrocarbyl, heteroatom-containing hydrocarbyl, and substituted heteroatom-containing, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups;

$X^1$ is a bidentate anionic ligand; in one embodiment $X^1$ is nitrate ($NO_3^-$), $C_1$-$C_{20}$ alkylcarboxylate, $C_6$-$C_{24}$ arylcarboxylate, $C_2$-$C_{24}$ aryloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl; in another embodiment $X^1$ is benzoate, pivalate, nitrate ($NO_3^-$)$_5$ an N-acetyl amino carboxylate, O-methyl mandelate, or a carboxylate derived from 2-phenylbutyric acid; in another embodiment $X^1$ is $CF_3CO_2$, $CH_3CO_2$, $CH_3CH_2CO_2$, $CFH_2CO_2$, $(CH_3)_3CO_2$, $(CH_3)_2CHCO_2$, $(CF_3)_2(CH_3)CO_2$, $(CF_3)(CH_3)_2CO_2$, benzoate, naphthylate, tosylate, mesylate, or trifluoromethane-sulfonate; in another embodiment, $X^1$ is pivalate or nitrate ($NO_3^-$); in another embodiment, $X^1$ is nitrate ($NO_3^-$);

Y is a heteroatom selected from N, O, S, and P; in another embodiment Y is a heteroatom selected from O or N; in another embodiment Y is a heteroatom selected from O;

$R^4$, $R^5$, $R^6$, and $R^7$ are each, independently, selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^4$, $R^5$, $R^6$, and $R^7$ can be linked to form one or more cyclic groups;

n is 1 or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, Q*, Y, Z, $R^4$, $R^5$, $R^6$, and $R^7$ are linked to a support; in one embodiment Z is selected from $C_1$-$C_6$ alkyl; in one embodiment Z is selected from $C_1$-$C_3$ alkyl.

In a further embodiment, for the C—H activated catalyst complexes of the invention having the structure of Formula (IV), $R^3$ maybe alkyl or aryl, and may be independently selected from alkyl, aryl, cycloalkyl, heteroalkyl, alkenyl, alkynyl, and halo or halogen-containing groups. In one embodiment, $R^3$ is selected from $C_1$-$C_{20}$ alkyl, $C_5$-$C_{14}$ cycloalkyl, $C_1$-$C_{20}$ heteroalkyl, or halide. Suitable alkyl groups include, without limitation, methyl, ethyl, n-propyl, isopropyl, isopropyl, n-butyl, isobutyl, t-butyl, octyl, decyl, and the like; suitable cycloalkyl groups include cyclopentyl, cyclohexyl, adamantyl, pinenyl, terpenes and terpenoid derivatives and the like; suitable alkenyl groups include ethenyl, n-propenyl, isopropenyl, n-butenyl, isobutenyl, octenyl, decenyl, tetradecenyl, hexadecenyl, eicosenyl, tetracosenyl, and the like; suitable alkynyl groups include ethynyl, n-propynyl, and the like; in one embodiment $R^3$ is selected from t-butyl or adamantyl; in one embodiment $R^3$ is selected from adamantyl.

In one embodiment, for the C—H activated catalyst complexes of the invention having the structure of Formula (IV), when $R^3$ is aromatic, each can be independently composed of one or two aromatic rings, which may or may not be substituted, e.g., $R^3$ may be phenyl, substituted phenyl, biphenyl, substituted biphenyl, or the like. In a particular embodiment, $R^3$ is an unsubstituted phenyl or phenyl substituted with up to three substituents selected from $C_1$-$C_{20}$ alkyl, $C_1$-$C_{20}$ alkylcarboxylate, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. In one embodiment, any substituents present are hydrogen $C_1$-$C_{12}$ alkyl, $C_1$-$C_{12}$ alkoxy, $C_5$-$C_{14}$ aryl, substituted, $C_5$-$C_{14}$ aryl, or halide. In another embodiment, $R^3$ is substituted with hydrogen, $C_1$-$C_4$ alkyl, $C_1$-$C_4$ alkylcarboxylate, $C_1$-$C_4$ alkoxy, $C_5$-$C_{14}$ aryl, substituted $C_5$-$C_{14}$ aryl, or halide.

As an example, for the C—H activated catalyst complexes of the invention having the structure of Formula (IV), $R^3$ is selected from cyclopentyl, cyclohexyl, adamantyl, norbonenyl, pinenyl, terpenes and terpenoid derivatives, mesityl, diisopropylphenyl or, more generally, cycloalkyl substituted with one, two or three $C_1$-$C_4$ alkyl or $C_1$-$C_4$ alkoxy groups, or a combination thereof. In one embodiment, $R^3$ is selected from mesityl, t-butyl, or adamantyl. In one embodiment, $R^3$ is selected from mesityl or adamantyl.

In one embodiment, the olefin metathesis catalyst complexes of the invention are C—H activated catalyst complexes having the structure of Formula (V):

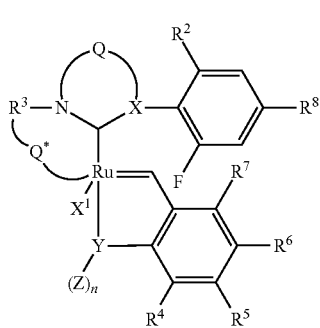

Formula (V)

wherein, $R^2$ is $C_2$-$C_6$ alkyl, methyl, substituted $C_1$-$C_6$ alkyl (e.g., $CFH_2$, $CF_2H$, $CF_3$, etc.), $C_5$-$C_8$ cycloalkyl, $C_5$-$C_8$ substituted cycloalkyl, heteroatom-containing hydrocarbyl, or substituted heteroatom-containing hydrocarbyl, where the substituents are selected from $C_1$-$C_6$ alkyl, $C_1$-$C_6$ alkoxy, or halide; in other embodiments $R^2$ is $C_2$-$C_6$ alkyl or $CF_3$; in other embodiments $R^2$ is $C_2$-$C_6$ alkyl; in other embodiments $R^2$ is $C_3$ alkyl (e.g., propyl or isopropyl);

$R^8$ is selected from hydrogen, $C_1$-$C_{10}$ alkyl, substituted $C_1$-$C_{10}$ alkyl, $C_5$-$C_{10}$ aryl, substituted $C_5$-$C_{10}$ aryl, $C_5$-$C_{10}$ heteroaryl, substituted $C_5$-$C_{10}$ heteroaryl, halide (—Cl, —F, —Br, —I), hydroxyl, $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, $C_5$-$C_{10}$ aryl, $C_5$-$C_{10}$ heteroaryl, halide (—Cl, —F, —Br, —I), $C_1$-$C_6$ alkoxy, nitro (—$NO_2$), ester (—COOR$^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), carboxylic acid (—COOH), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), cyano (—CN), where $R^9$ is hydrogen, methyl, $C_2$-$C_6$ alkyl;

Q* is a 2-electron anionic donor bridging moiety linking $R^3$ and Ru; and may be hydrocarbylene (including substituted hydrocarbylene, heteroatom-containing hydrocarbylene, and substituted heteroatom-containing hydrocarbylene, such as substituted and/or heteroatom-containing alkylene) or —(CO)—;

Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage. In particular embodiments, Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of suitable functional groups include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers;

X is an atom selected from C, N, and P; in one embodiment X is an atom selected from N;

$R^3$ is independently selected from hydrocarbyl, substituted hydrocarbyl, heteroatom-containing hydrocarbyl, and substituted heteroatom-containing, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups;

$X^1$ is a bidentate anionic ligand; in one embodiment $X^1$ is nitrate ($NO_3^-$), $C_1$-$C_{20}$ alkylcarboxylate, $C_6$-$C_{24}$ arylcarboxylate, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl; in another embodiment $X^1$ is benzoate, pivalate, nitrate ($NO_3^-$), an N-acetyl amino carboxylate, O-methyl mandelate, or a carboxylate derived from 2-phenylbutyric acid; in another embodiment $X^1$ is $CF_3CO_2$, $CH_3CO_2$, $CH_3CH_2CO_2$, $CFH_2CO_2$, $(CH_3)_3CO_2$, $(CH_3)_2CHCO_2$, $(CF_3)_2(CH_3)CO_2$, $(CF_3)(CH_3)_2CO_2$, benzoate, naphthylate, tosylate, mesylate, or trifluoromethane-sulfonate; in another embodiment, $X^1$ is pivalate or nitrate ($NO_3^-$); in another embodiment, $X^1$ is nitrate ($NO_3^-$);

Y is a heteroatom selected from N, O, S, and P; in another embodiment Y is a heteroatom selected from O or N; in another embodiment Y is a heteroatom selected from O;

$R^4$, $R^5$, $R^6$, and $R^7$ are each, independently, selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^4$, $R^5$, $R^6$, and $R^7$ can be linked to form one or more cyclic groups;

n is 1 or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, $Q^*$, Y, Z, $R^4$, $R^5$, $R^6$, and $R^7$ are linked to a support; in one embodiment Z is selected from $C_1$-$C_6$ alkyl; in one embodiment Z is selected from $C_1$-$C_3$ alkyl.

In another embodiment, for the C—H activated catalyst complexes of the invention having the structure of Formula (V), $R^3$ maybe alkyl or aryl, and may be independently selected from alkyl, aryl, cycloalkyl, heteroalkyl, alkenyl, alkynyl, and halo or halogen-containing groups. In one embodiment, $R^3$ is selected from $C_1$-$C_{20}$ alkyl, $C_5$-$C_{14}$ cycloalkyl, $C_1$-$C_{20}$ heteroalkyl, or halide. Suitable alkyl groups include, without limitation, methyl, ethyl, n-propyl, isopropyl, isopropyl, n-butyl, isobutyl, t-butyl, octyl, decyl, and the like; suitable cycloalkyl groups include cyclopentyl, cyclohexyl, adamantyl, pinenyl, terpenes and terpenoid derivatives, and the like; suitable alkenyl groups include ethenyl, n-propenyl, isopropenyl, n-butenyl, isobutenyl, octenyl, decenyl, tetradecenyl, hexadecenyl, eicosenyl, tetracosenyl, and the like; suitable alkynyl groups include ethynyl, n-propynyl, and the like; in one embodiment $R^3$ is selected from t-butyl or adamantyl; in one embodiment $R^3$ is selected from adamantyl.

In one embodiment, for the C—H activated catalyst complexes of the invention having the structure of Formula (V), when $R^3$ is aromatic, each can be independently composed of one or two aromatic rings, which may or may not be substituted, e.g., $R^3$ may be phenyl, substituted phenyl, biphenyl, substituted biphenyl, or the like. In a particular embodiment, $R^3$ is an unsubstituted phenyl or phenyl substituted with up to three substituents selected from $C_1$-$C_{20}$ alkyl, $C_1$-$C_{20}$ alkylcarboxylate, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. In one embodiment, any substituents present are hydrogen $C_1$-$C_{12}$ alkyl, $C_1$-$C_{12}$ alkoxy, $C_5$-$C_{14}$ aryl, substituted, $C_5$-$C_{14}$ aryl, or halide. In another embodiment, $R^3$ is substituted with hydrogen, $C_1$-$C_4$ alkyl, $C_1$-$C_4$ alkylcarboxylate, $C_1$-$C_4$ alkoxy, $C_5$-$C_{14}$ aryl, substituted $C_5$-$C_{14}$ aryl, or halide.

As an example, for the C—H activated catalyst complexes of the invention having the structure of Formula (V), $R^3$ is selected from cyclopentyl, cyclohexyl, adamantyl, norbonenyl, pinenyl, terpenes and terpenoid derivatives, mesityl, diisopropylphenyl or, more generally, cycloalkyl substituted with one, two or three $C_1$-$C_4$ alkyl or $C_1$-$C_4$ alkoxy groups, or a combination thereof. In one embodiment, $R^3$ is selected from mesityl, t-butyl, or adamantyl. In one embodiment, $R^3$ is selected from mesityl or adamantyl.

Still, in a further embodiment, the olefin metathesis catalyst complexes of the invention are C—H activated catalyst complexes having the structure of Formula (VI):

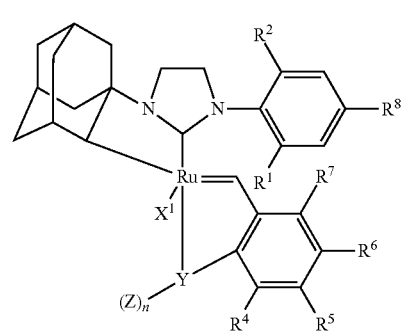

Formula (VI)

wherein, $R^1$ is $C_1$-$C_6$ alkyl, substituted $C_1$-$C_6$ alkyl, $C_5$-$C_8$ cycloalkyl, $C_5$-$C_8$ substituted cycloalkyl, $C_1$-$C_6$ alkoxy, or halide, where the substituents are selected from $C_1$-$C_6$ alkyl, $C_1$-$C_6$ alkoxy, or halide; in other embodiments $R^1$ is $C_1$-$C_6$ alkyl, or F; in other embodiments $R^1$ is $C_1$-$C_3$ alkyl, $C_1$-$C_3$ alkoxy, or F; in other embodiments $R^1$ is $C_1$-$C_4$ alkyl or F; in other embodiments $R^1$ is $C_1$-$C_3$ alkyl or F; in other embodiments $R^1$ is $OCH_3$ (i.e., OMe);

$R^2$ is heteroatom-containing hydrocarbyl, or substituted heteroatom-containing hydrocarbyl, where the substituents are selected from $C_1$-$C_6$ alkyl, $C_1$-$C_6$ alkoxy, or halide; in other embodiments $R^2$ is $C_1$-$C_6$ alkoxy; in other embodiments $R^2$ is $C_1$-$C_4$ alkoxy; in other embodiments $R^2$ is $C_1$-$C_3$ alkoxy; in other embodiments $R^2$ is $OCH_3$ (i.e., OMe);

$R^8$ is selected from hydrogen, $C_2$-$C_{10}$ alkyl, substituted $C_1$-$C_{10}$ alkyl, $C_5$-$C_{10}$ aryl, substituted $C_5$-$C_{10}$ aryl, $C_5$-$C_{10}$ heteroaryl, substituted $C_5$-$C_{10}$ heteroaryl, halide (—Cl, —F, —Br, —I), hydroxyl, $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, $C_5$-$C_{10}$ aryl, $C_5$-$C_{10}$ heteroaryl, halide (—Cl, —F, —Br, —I), $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), carboxylic acid (—COOH), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), cyano (—CN), where $R^9$ is hydrogen, methyl, $C_2$-$C_6$ alkyl;

$X^1$ is a bidentate anionic ligand; in one embodiment $X^1$ is nitrate ($NO_3^-$), $C_1$-$C_{20}$ alkylcarboxylate, $C_6$-$C_{24}$ arylcarboxylate, $C_2$-$C_{24}$ aryloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl; in another embodiment $X^1$ is benzoate, pivalate, nitrate ($NO_3^-$), an N-acetyl amino carboxylate, O-methyl mandelate, or a carboxylate derived from 2-phenylbutyric acid; in another embodiment $X^1$ is $CF_3CO_2$, $CH_3CO_2$, $CH_3CH_2CO_2$, $CFH_2CO_2$, $(CH_3)_3CO_2$, $(CH_3)_2CHCO_2$, $(CF_3)_2(CH_3)CO_2$, $(CF_3)(CH_3)_2CO_2$, benzoate, naphthylate, tosylate, mesylate, or trifluoromethane-sulfonate; in another embodiment, $X^1$ is pivalate or nitrate ($NO_3^-$); in another embodiment, $X^1$ is nitrate ($NO_3^-$);

Y is a heteroatom selected from N, O, S, and P; in another embodiment Y is a heteroatom selected from O or N; in another embodiment Y is a heteroatom selected from O;

$R^4$, $R^5$, $R^6$, and $R^7$ are each, independently, selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^4$, $R^5$, $R^6$, and $R^7$ can be linked to form one or more cyclic groups;

n is 1 or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more of the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, Y, Z, $R^4$, $R^5$, $R^6$, and $R^7$ are linked to a support; in one embodiment Z is selected from $C_1$-$C_6$ alkyl; in one embodiment Z is selected from $C_1$-$C_3$ alkyl; and the olefin metathesis catalyst complex of Formula (VI) is not:

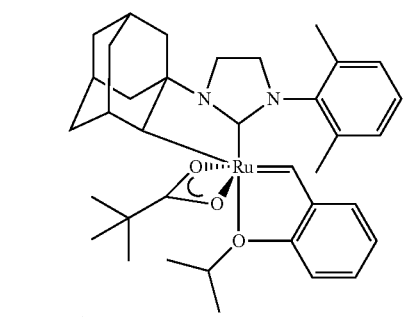
,

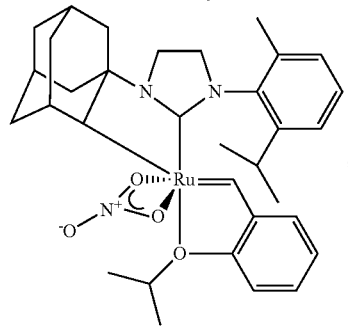
,

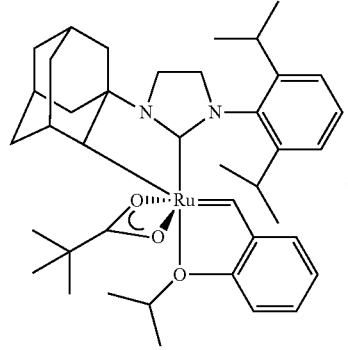
,

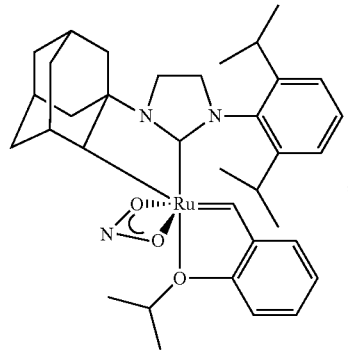
,

-continued

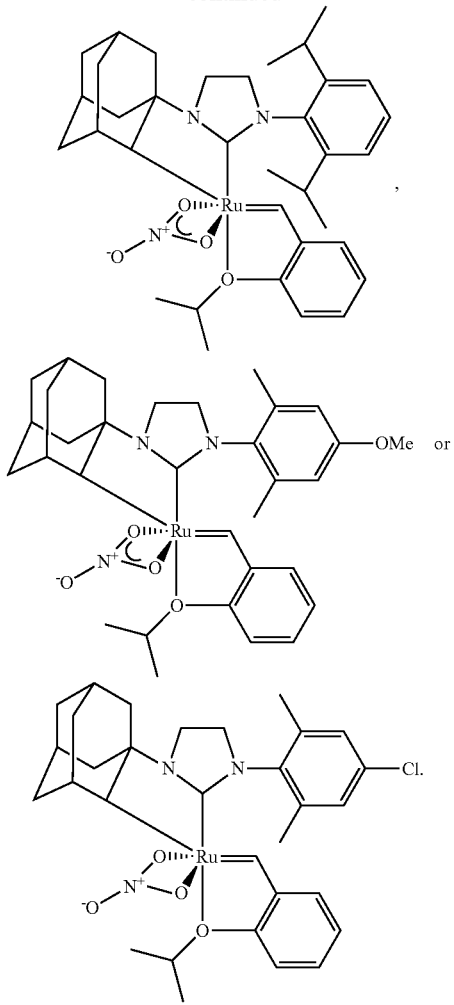

Still, in a further embodiment, the olefin metathesis catalyst complexes of the invention are C—H activated catalyst complexes having the structure of Formula (VII):

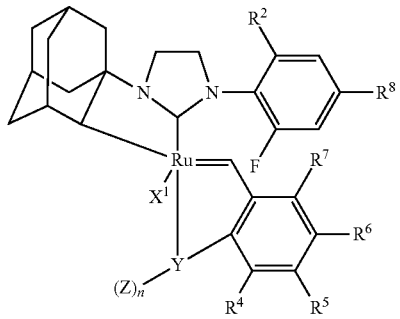

Formula (VII)

wherein, $R^2$ is $C_2$-$C_6$ alkyl, methyl, substituted $C_1$-$C_6$ alkyl (e.g., $CFH_2$, $CF_2H$, $CF_3$, etc.), $C_5$-$C_8$ cycloalkyl, $C_5$-$C_8$ substituted cycloalkyl, heteroatom-containing hydrocarbyl, or substituted heteroatom-containing hydrocarbyl, where the substituents are selected from $C_1$-$C_6$ alkyl, $C_1$-$C_6$ alkoxy, or halide; in other embodiments $R^2$ is $C_2$-$C_6$ alkyl or $CF_3$; in other embodiments $R^2$ is $C_2$-$C_6$ alkyl; in other embodiments $R^2$ is $C_3$ alkyl (e.g., propyl or isopropyl);

$R^8$ is selected from hydrogen, $C_1$-$C_{10}$ alkyl, substituted $C_1$-$C_{10}$ alkyl, $C_5$-$C_{10}$ aryl, substituted $C_5$-$C_{10}$ aryl, $C_5$-$C_{10}$ heteroaryl, substituted $C_5$-$C_{10}$ heteroaryl, halide (—Cl, —F, —Br, —I), hydroxyl, $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, $C_5$-$C_{10}$ aryl, $C_5$-$C_{10}$ heteroaryl, halide (—Cl, —F, —Br, —I), $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), carboxylic acid (—COOH), carbamate (—$NCO_2R^9$), cyano (—CN), sulfoxide (—$SOR^9$), sulfonyl (—$SO_2R^9$), sulfonic acid (—$SO_3H$), fluoromethyl (—CFO, fluroaryl (e.g., —$C_6F_5$, p-$CF_3C_6H_4$), where $R^9$ is hydrogen, methyl, $C_2$-$C_6$ alkyl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), cyano (—CN), where $R^9$ is hydrogen, methyl, $C_2$-$C_6$ alkyl;

$X^1$ is a bidentate anionic ligand; in one embodiment $X^1$ is nitrate ($NO_3^-$), $C_1$-$C_{20}$ alkylcarboxylate, $C_6$-$C_{24}$ arylcarboxylate, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl; in another embodiment $X^1$ is benzoate, pivalate, nitrate ($NO_3^-$), an N-acetyl amino carboxylate, O-methyl mandelate, or a carboxylate derived from 2-phenylbutyric acid; in another embodiment $X^1$ is $CF_3CO_2$, $CH_3CO_2$, $CH_3CH_2CO_2$, $CFH_2CO_2$, $(CH_3)_3CO_2$, $(CH_3)_2CHCO_2$, $(CF_3)_2(CH_3)CO_2$, $(CF_3)(CH_3)_2CO_2$, benzoate, naphthylate, tosylate, mesylate, or trifluoromethane-sulfonate; in another embodiment, $X^1$ is pivalate or nitrate ($NO_3^-$); in another embodiment, $X^1$ is nitrate ($NO_3^-$);

Y is a heteroatom selected from N, O, S, and P; in another embodiment Y is a heteroatom selected from O or N; in another embodiment Y is a heteroatom selected from O;

$R^4$, $R^5$, $R^6$, and $R^7$ are each, independently, selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^4$, $R^5$, $R^6$, and $R^7$ can be linked to form one or more cyclic groups;

n is 1 or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, Y, Z, $R^4$, $R^5$, $R^6$, and $R^7$ are linked to a support; in one embodiment Z is selected from $C_1$-$C_6$ alkyl; in one embodiment Z is selected from $C_1$-$C_3$ alkyl.

Still, in a further embodiment, the olefin metathesis catalyst complexes of the invention are C—H activated catalyst complexes having the structure of Formula (VIII):

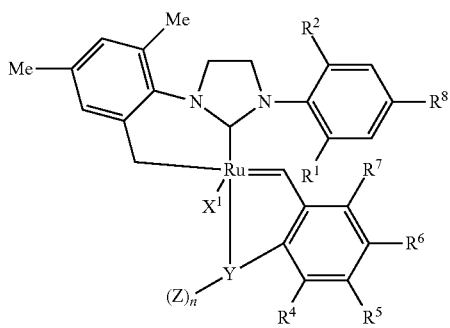

Formula (VIII)

wherein, $R^1$ is $C_1$-$C_6$ alkyl, substituted $C_1$-$C_6$ alkyl, $C_5$-$C_8$ cycloalkyl, $C_5$-$C_8$ substituted cycloalkyl, $C_1$-$C_6$ alkoxy, or halide, where the substituents are selected from $C_1$-$C_6$ alkyl, $C_1$-$C_6$ alkoxy, or halide; in other embodiments $R^1$ is $C_1$-$C_6$ alkyl, or F; in other embodiments $R^1$ is $C_1$-$C_3$ alkyl, $C_1$-$C_3$ alkoxy, or F; in other embodiments $R^1$ is $C_1$-$C_4$ alkyl or F; in other embodiments $R^1$ is $C_1$-$C_3$ alkyl or F; in other embodiments $R^1$ is $OCH_3$ (i.e., OMe);

$R^2$ is heteroatom-containing hydrocarbyl, or substituted heteroatom-containing hydrocarbyl, where the substituents are selected from $C_1$-$C_6$ alkyl, $C_1$-$C_6$ alkoxy, or halide; in other embodiments $R^2$ is $C_1$-$C_6$ alkoxy; in other embodiments $R^2$ is $C_1$-$C_4$ alkoxy; in other embodiments $R^2$ is $C_1$-$C_3$ alkoxy; in other embodiments $R^2$ is $OCH_3$ (i.e., OMe);

$R^8$ is selected from hydrogen, $C_1$-$C_{10}$ alkyl, substituted $C_1$-$C_{10}$ alkyl, $C_5$-$C_{10}$ aryl, substituted $C_5$-$C_{10}$ aryl, $C_5$-$C_{10}$ heteroaryl, substituted $C_5$-$C_{10}$ heteroaryl, halide (—Cl, —F, —Br, —I), hydroxyl, $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, $C_5$-$C_{10}$ aryl, $C_5$-$C_{10}$ heteroaryl, halide (—Cl, —F, —Br, —I), $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), cyano (—CN), where $R^9$ is hydrogen, methyl, $C_2$-$C_6$ alkyl;

$X^1$ is a bidentate anionic ligand; in one embodiment $X^1$ is nitrate ($NO_3^-$), $C_1$-$C_{20}$ alkylcarboxylate, $C_6$-$C_{24}$ arylcarboxylate, $C_2$-$C_{24}$ aryloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl; in another embodiment $X^1$ is benzoate, pivalate, nitrate ($NO_3^-$), an N-acetyl amino carboxylate, O-methyl mandelate, or a carboxylate derived from 2-phenylbutyric acid; in another embodiment $X^1$ is $CF_3CO_2$, $CH_3CO_2$, $CH_3CH_2CO_2$, $CFH_2CO_2$, $(CH_3)_3CO_2$, $(CH_3)_2CHCO_2$, $(CF_3)_2(CH_3)CO_2$, $(CF_3)(CH_3)_2CO_2$, benzoate, naphthylate, tosylate, mesylate, or trifluoromethane-sulfonate; in another embodiment, $X^1$ is pivalate or nitrate ($NO_3^-$); in another embodiment, $X^1$ is nitrate ($NO_3^-$);

Y is a heteroatom selected from N, O, S, and P; in another embodiment Y is a heteroatom selected from O or N; in another embodiment Y is a heteroatom selected from O;

$R^4$, $R^5$, $R^6$, and $R^7$ are each, independently, selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^4$, $R^5$, $R^6$, and $R^7$ can be linked to form one or more cyclic groups;

n is 1 or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, Y, Z, $R^4$, $R^5$, $R^6$, and $R^7$ are linked to a support; in one embodiment Z is selected from $C_1$-$C_6$ alkyl; in one embodiment Z is selected from $C_1$-$C_3$ alkyl.

Still in another embodiment, the olefin metathesis catalyst complexes of the invention are C—H activated catalyst complexes having the structure of Formula (IX):

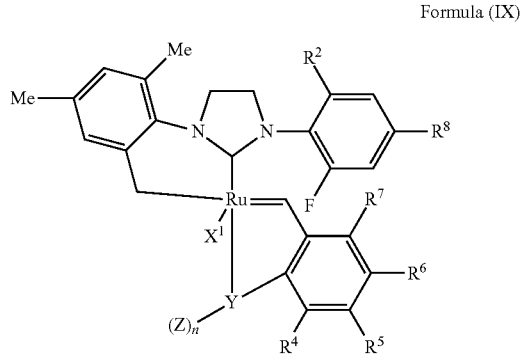

Formula (IX)

wherein, $R^2$ is $C_2$-$C_6$ alkyl, methyl, substituted $C_1$-$C_6$ alkyl (e.g., $CFH_2$, $CF_2H$, $CF_3$, etc.), $C_5$-$C_8$ cycloalkyl, $C_5$-$C_8$ substituted cycloalkyl, heteroatom-containing hydrocarbyl, or substituted heteroatom-containing hydrocarbyl, where the substituents are selected from $C_1$-$C_6$ alkyl, $C_1$-$C_6$ alkoxy, or halide; in other embodiments $R^2$ is $C_2$-$C_6$ alkyl or $CF_3$; in other embodiments $R^2$ is $C_2$-$C_6$ alkyl; in other embodiments $R^2$ is $C_3$ alkyl (e.g., propyl or isopropyl);

$R^8$ is selected from hydrogen, $C_1$-$C_{10}$ alkyl, substituted $C_1$-$C_{10}$ alkyl, $C_5$-$C_{10}$ aryl, substituted $C_5$-$C_{10}$ aryl, $C_5$-$C_{10}$ heteroaryl, substituted $C_5$-$C_{10}$ heteroaryl, halide (—Cl, —F, —Br, —I), hydroxyl, $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, $C_5$-$C_{10}$ aryl, $C_5$-$C_{10}$ heteroaryl, halide (—Cl, —F, —Br, —I), $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), carboxylic acid (—COOH), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), cyano (—CN), where $R^9$ is hydrogen, methyl, $C_2$-$C_6$ alkyl;

$X^1$ is a bidentate anionic ligand; in one embodiment $X^1$ is nitrate ($NO_3^-$), $C_1$-$C_{20}$ alkylcarboxylate, $C_6$-$C_{24}$ arylcarboxylate, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl; in another embodiment $X^1$ is benzoate, pivalate, nitrate ($NO_3^-$), an N-acetyl amino carboxylate, O-methyl mandelate, or a carboxylate derived from 2-phenylbutyric acid; in another embodiment $X^1$ is $CF_3CO_2$, $CH_3CO_2$, $CH_3CH_2CO_2$, $CFH_2CO_2$, $(CH_3)_3CO_2$, $(CH_3)_2CHCO_2$, $(CF_3)_2(CH_3)CO_2$, $(CF_3)(CH_3)_2CO_2$, benzoate, naphthylate, tosylate, mesylate, or trifluoromethane-sulfonate; in another embodiment, $X^1$ is pivalate or nitrate ($NO_3^-$); in another embodiment, $X^1$ is nitrate ($NO_3^-$);

Y is a heteroatom selected from N, O, S, and P; in another embodiment Y is a heteroatom selected from O or N; in another embodiment Y is a heteroatom selected from O;

$R^4$, $R^5$, $R^6$, and $R^7$ are each, independently, selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^4$, $R^5$, $R^6$, and $R^7$ can be linked to form one or more cyclic groups;

n is 1 or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, Y, Z, $R^4$, $R^5$, $R^6$, and $R^7$ are linked to a support; in one embodiment Z is selected from $C_1$-$C_6$ alkyl; in one embodiment Z is selected from $C_1$-$C_3$ alkyl.

Still, in another embodiment, the olefin metathesis catalyst complexes of the invention are C—H activated catalyst complexes having the structure of Formula (X):

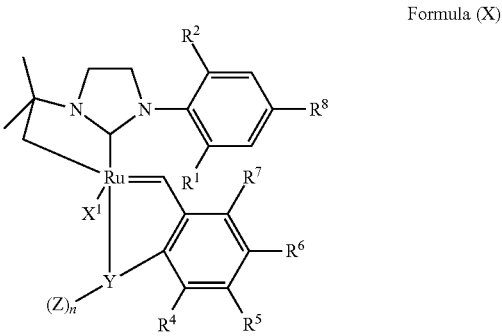

Formula (X)

wherein, $R^1$ is $C_1$-$C_6$ alkyl, substituted $C_1$-$C_6$ alkyl, $C_5$-$C_8$ cycloalkyl, $C_5$-$C_8$ substituted cycloalkyl, $C_1$-$C_6$ alkoxy, or halide, where the substituents are selected from $C_1$-$C_6$ alkyl, $C_1$-$C_6$ alkoxy, or halide; in other embodiments $R^1$ is $C_1$-$C_6$ alkyl, or F; in other embodiments $R^1$ is $C_1$-$C_3$ alkyl, $C_1$-$C_3$ alkoxy, or F; in other embodiments $R^1$ is $C_1$-$C_4$ alkyl or F; in other embodiments $R^1$ is $C_1$-$C_3$ alkyl or F; in other embodiments $R^1$ is $OCH_3$ (i.e., OMe);

$R^2$ is heteroatom-containing hydrocarbyl, or substituted heteroatom-containing hydrocarbyl, where the substituents are selected from $C_1$-$C_6$ alkyl, $C_1$-$C_6$ alkoxy, or halide; in other embodiments $R^2$ is $C_1$-$C_6$ alkoxy; in other embodiments $R^2$ is $C_1$-$C_4$ alkoxy; in other embodiments $R^2$ is $C_1$-$C_3$ alkoxy; in other embodiments $R^2$ is $OCH_3$ (i.e., OMe);

$R^8$ is selected from hydrogen, $C_1$-$C_{10}$ alkyl, substituted $C_1$-$C_{10}$ alkyl, $C_5$-$C_{10}$ aryl, substituted $C_5$-$C_{10}$ aryl, $C_5$-$C_{10}$ heteroaryl, substituted $C_5$-$C_{10}$ heteroaryl, halide (—Cl, —F, —Br, —I), hydroxyl, $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, $C_5$-$C_{10}$ aryl, $C_5$-$C_{10}$ heteroaryl, halide (—Cl, —F, —Br, —I), $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), carboxylic acid (—COOH), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, wherein n is 1, 2, or 3; in another embodiment $R^8$ is selected from hydrogen, $C_1$-$C_{10}$ alkyl, halide (—Cl, —F, —Br, —I), $C_1$-$C_6$ alkoxy, nitro (—$NO_2$), ester (—$COOR^9$), ketone (—$COR^9$), aldehyde (—COH), acyl (—$COR^9$), ester (—$OCOR^9$), cyano (—CN), where $R^9$ is hydrogen, methyl, $C_2$-$C_6$ alkyl;

$X^1$ is a bidentate anionic ligand; in one embodiment $X^1$ is nitrate ($NO_3^-$), $C_1$-$C_{20}$ alkylcarboxylate, $C_6$-$C_{24}$ arylcarboxylate, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl; in another embodiment $X^1$ is benzoate, pivalate, nitrate ($NO_3^-$), an N-acetyl amino carboxylate, O-methyl mandelate, or a carboxylate derived from 2-phenylbutyric acid; in another embodiment $X^1$ is $CF_3CO_2$, $CH_3CO_2$, $CH_3CH_2CO_2$, $CFH_2CO_2$, $(CH_3)_3CO_2$, $(CH_3)_2CHCO_2$, $(CF_3)_2(CH_3)CO_2$, $(CF_3)(CH_3)_2CO_2$, benzoate, naphthylate, tosylate, mesylate, or trifluoromethane-sulfonate; in another embodiment $X^1$ is pivalate or nitrate ($NO_3^-$); in another embodiment $X^1$ is nitrate ($NO_3^-$);

Y is a heteroatom selected from N, O, S, and P; in another embodiment Y is a heteroatom selected from O or N; in another embodiment Y is a heteroatom selected from O;

$R^4$, $R^5$, $R^6$, and $R^7$ are each, independently, selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^4$, $R^5$, $R^6$, and $R^7$ can be linked to form one or more cyclic groups;

n is 1 or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, Y, Z, $R^4$, $R^5$, $R^6$, and $R^7$ are linked to a support; in one embodiment Z is selected from $C_1$-$C_6$ alkyl; in one embodiment Z is selected from $C_1$-$C_3$ alkyl.

In a further embodiment, the olefin metathesis catalyst complexes of the invention are C—H activated catalyst complexes having the structure of Formula (XI):

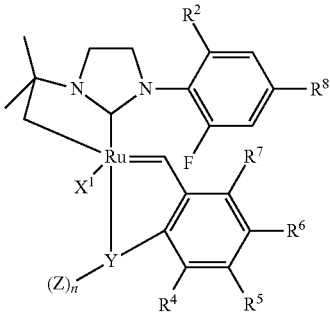

Formula (XI)

wherein, $R^2$ is $C_2$-$C_6$ alkyl, substituted $C_1$-$C_6$ alkyl (e.g., $CFH_2$, $CF_2H$, $CF_3$, etc.), $C_5$-$C_8$ cycloalkyl, $C_5$-$C_8$ substituted cycloalkyl, heteroatom-containing hydrocarbyl, or substituted heteroatom-containing hydrocarbyl, where the substituents are selected from $C_1$-$C_6$ alkyl, $C_1$-$C_6$ alkoxy, or halide; in other embodiments $R^2$ is $C_2$-$C_6$ alkyl or $CF_3$; in other embodiments $R^2$ is $C_2$-$C_6$ alkyl; in other embodiments $R^2$ is $C_3$ alkyl (e.g., propyl or isopropyl);

$R^8$ is selected from hydrogen, $C_1$-$C_{10}$ alkyl, substituted $C_1$-$C_{10}$ alkyl, $C_5$-$C_{10}$ aryl, substituted $C_5$-$C_{10}$ aryl, $C_5$-$C_{10}$ heteroaryl, substituted $C_5$-$C_{10}$ heteroaryl, halide (—Cl, —F, —Br, —I), hydroxyl, $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—$NR^9SO_2Ar$), carbamate (—$NCO_2R^9$), cyano (—CN), sulfoxide (—$SOR^9$), sulfonyl (—$SO_2R^9$), sulfonic acid (—$SO_3H$), fluoromethyl (—$CF_n$), fluroaryl (e.g., —$C_6F_5$, p-$CF_3C_6H_4$), where $R^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3; in another embodiment $R^8$ is selected from hydrogen, $C_1$-$C_{10}$ alkyl, $C_5$-$C_{10}$ aryl, $C_5$-$C_{10}$ heteroaryl, halide (—Cl, —F, —Br, —I), $C_1$-$C_6$ alkoxy, $C_5$-$C_{10}$ aryloxy, nitro (—$NO_2$), ester (—$COOR^9$), ketone (—$COR^9$), aldehyde (—COH), acyl (—$COR^9$), ester (—$OCOR^9$), carboxylic acid (—COOH), sulfonamide (—NR⁹SO₂Ar), carbamate (—NCO₂R⁹), cyano (—CN), sulfoxide (—SOR⁹), sulfonyl (—SO₂R⁹), sulfonic acid (—SO₃H), fluoromethyl (—CF$_n$), fluroaryl (e.g., —C₆F₅, p-CF₃C₆H₄), where R⁹ is hydrogen, methyl, C₂-C₆ alkyl, substituted C₂-C₆ alkyl, C₅-C₁₀ aryl, or substituted C₅-C₁₀ aryl, wherein n is 1, 2, or 3; in another embodiment R⁸ is selected from hydrogen, C₁-C₁₀ alkyl, halide (—Cl, —F, —Br, —I), C₁-C₆ alkoxy, nitro (—NO₂), ester (—COOR⁹), ketone (—COR⁹), aldehyde (—COH), acyl (—COR⁹), ester (—OCOR⁹), carboxylic acid (—COOH), carbamate (—NCO₂R⁹), cyano (—CN), sulfoxide (—SOR⁹), sulfonyl (—SO₂R⁹), sulfonic acid (—SO₃H), fluoromethyl (—CF$_n$), fluroaryl (e.g., —C₆F₅, p-CF₃C₆H₄), where R⁹ is hydrogen, methyl, C₂-C₆ alkyl, wherein n is 1, 2, or 3; in another embodiment R⁸ is selected from hydrogen, C₁-C₁₀ alkyl, halide (—Cl, —F, —Br, —I), C₁-C₆ alkoxy, nitro (—NO₂), ester (—COOR⁹), ketone (—COR⁹), aldehyde (—COH), acyl (—COR⁹), ester (—OCOR⁹), cyano (—CN), where R⁹ is hydrogen, methyl, C₂-C₆ alkyl;

X¹ is a bidentate anionic ligand; in one embodiment X¹ is nitrate (NO₃⁻), C₁-C₂₀ alkylcarboxylate, C₆-C₂₄ arylcarboxylate, C₂-C₂₄ aryloxy, C₁-C₂₀ alkylsulfonato, C₅-C₂₄ arylsulfonato, C₁-C₂₀ alkylsulfanyl, C₅-C₂₄ arylsulfanyl, C₁-C₂₀ alkylsulfinyl, or C₅-C₂₄ arylsulfinyl; in another embodiment X¹ is benzoate, pivalate, nitrate (NO₃⁻), an N-acetyl amino carboxylate, O-methyl mandelate, or a carboxylate derived from 2-phenylbutyric acid; in another embodiment X¹ is CF₃CO₂, CH₃CO₂, CH₃CH₂CO₂, CFH₂CO₂, (CH₃)₃CO₂, (CH₃)₂CHCO₂, (CF₃)₂(CH₃)CO₂, (CF₃)(CH₃)₂CO₂, benzoate, naphthylate, tosylate, mesylate, or trifluoromethane-sulfonate; in another embodiment, X¹ is pivalate or nitrate (NO₃⁻); in another embodiment, X¹ is nitrate (NO₃⁻);

Y is a heteroatom selected from N, O, S, and P; in another embodiment Y is a heteroatom selected from O or N; in another embodiment Y is a heteroatom selected from O;

R⁴, R⁵, R⁶, and R⁷ are each, independently, selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of R⁴, R⁵, R⁶, and R⁷ can be linked to form one or more cyclic groups;

n is 1 or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of X¹, Y, Z, R⁴, R⁵, R⁶, and R⁷ are linked to a support; in one embodiment Z is selected from C₁-C₆ alkyl; in one embodiment Z is selected from C₁-C₃ alkyl.

Examples of C—H activated catalyst complexes having the structure of Formula (VI) include the following:

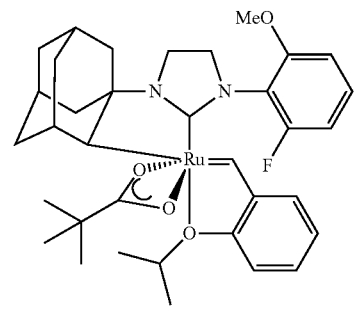

Ru-8

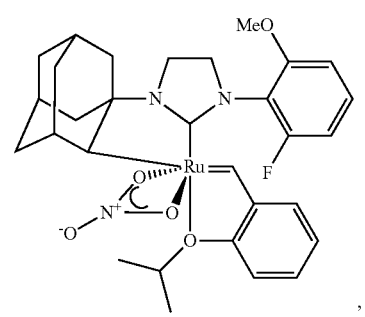

Ru-9

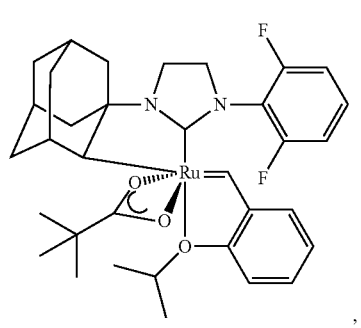

Ru-10

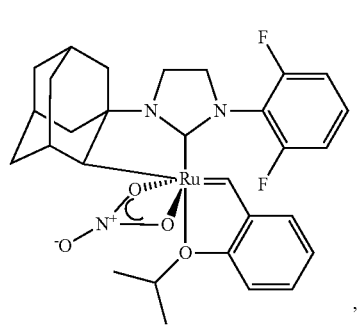

Ru-11

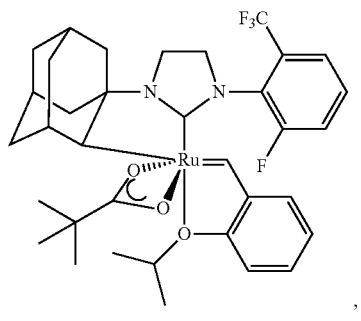

Ru-12

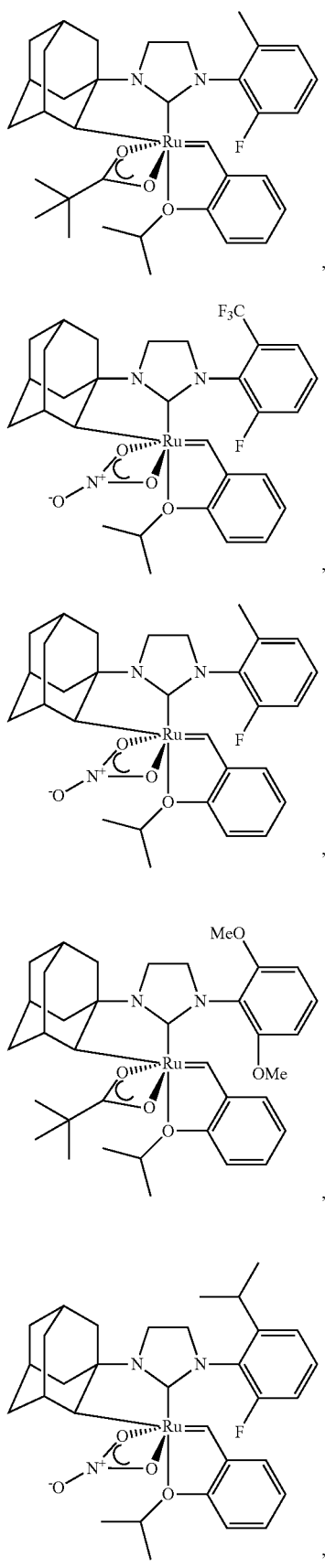
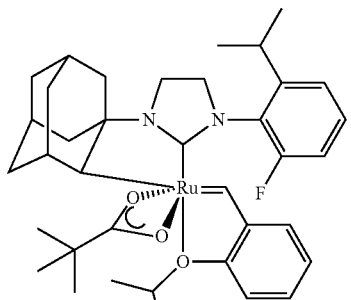
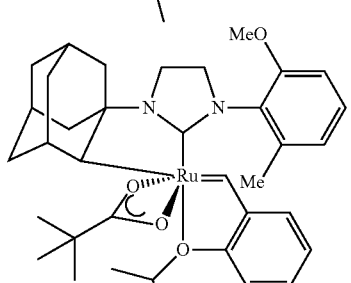
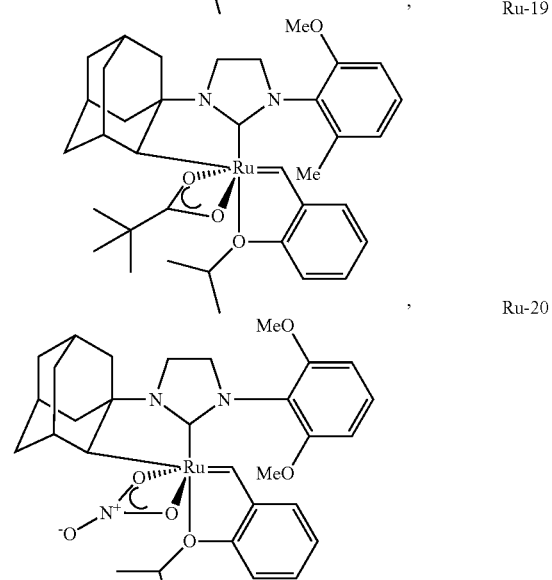
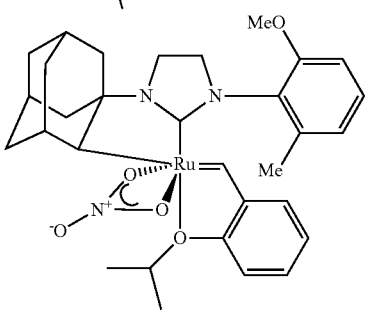
Examples of C—H activated catalyst complexes having the structure of Formula (VII) include the following:
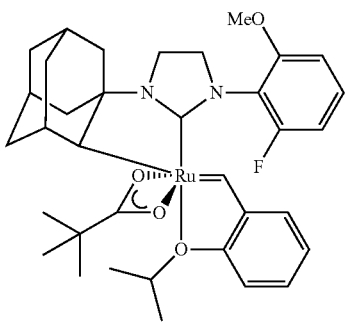

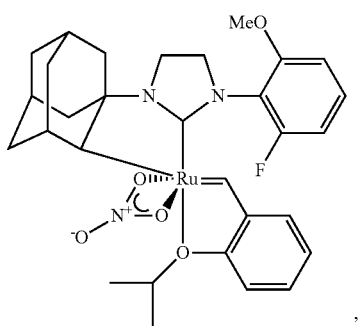 Ru-9
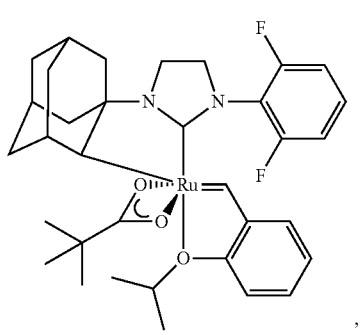 Ru-10
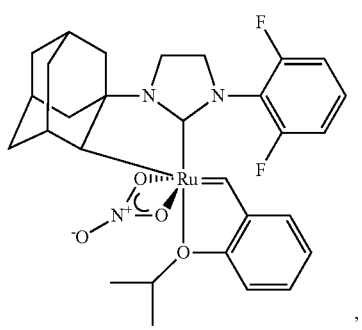 Ru-11
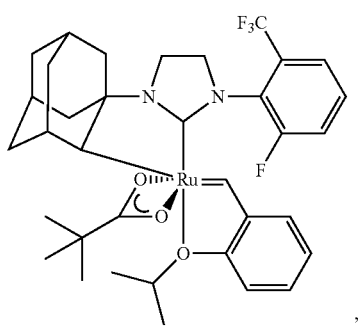 Ru-12
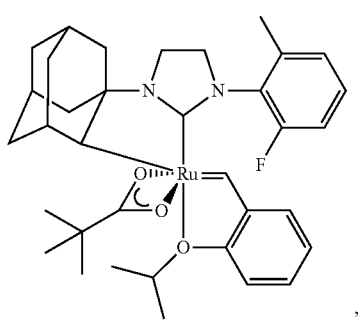 Ru-13
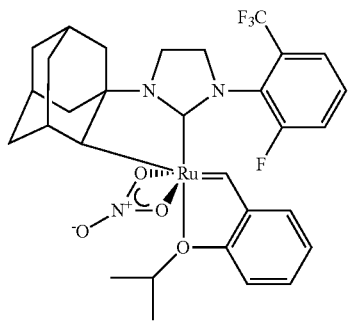 Ru-14
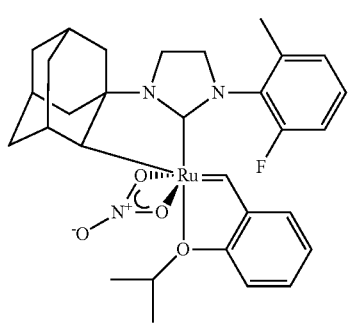 Ru-15
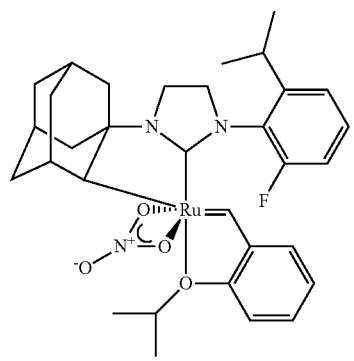 Ru-17
, and
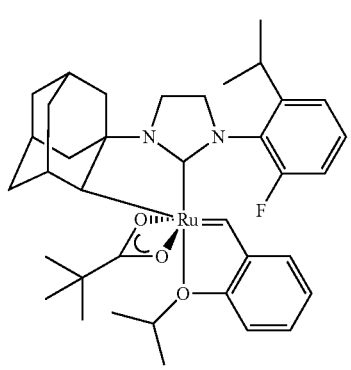 Ru-18
.
An example of a C—H activated catalyst complex having the structure of Formula (IV) or Formula (VI) includes the following:

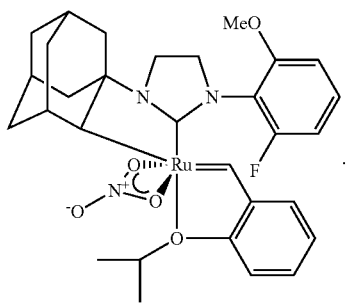
Ru-9
An example of a C—H activated catalyst complex having the structure of Formula (VI) includes the following:
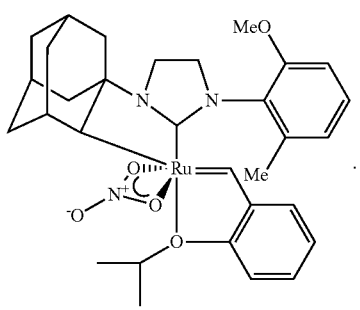
Ru-21
Examples of C—H activated catalyst complexes having the structure of Formula (VII) include the following:
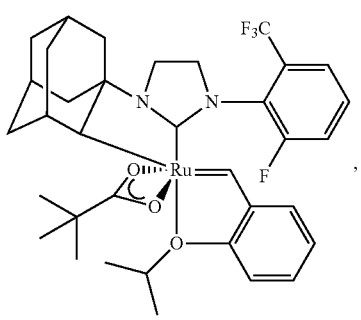
Ru-12
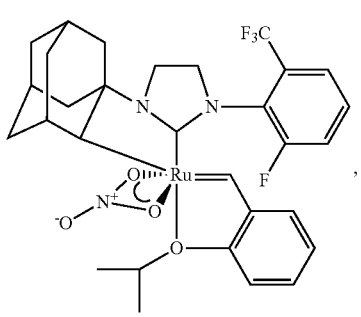
Ru-14
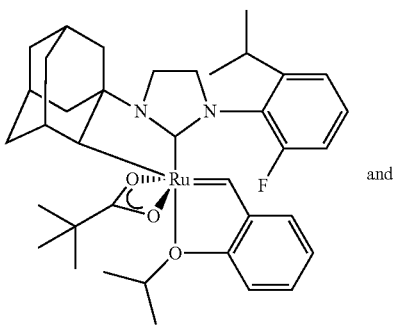
Ru-18
and
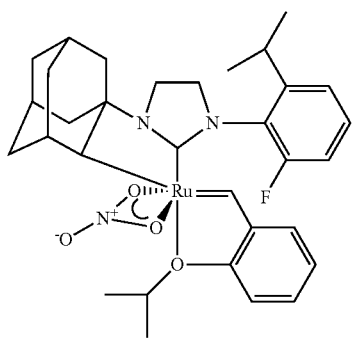
Ru-17
Examples of C—H activated catalyst complexes having the structure of Formula (VII) include the following:
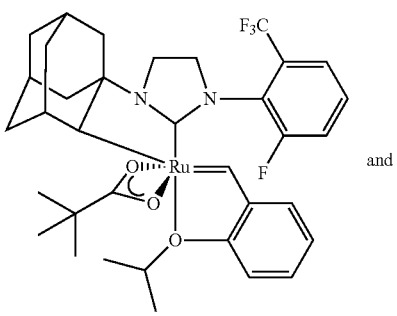
Ru-12
and
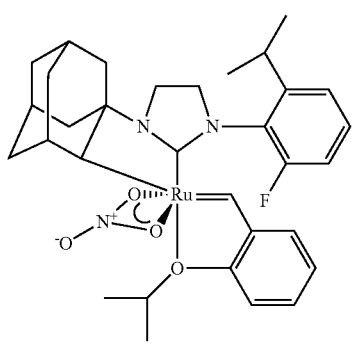
Ru-17

An example of a C—H activated catalyst complex having the structure of Formula (VII) includes the following:

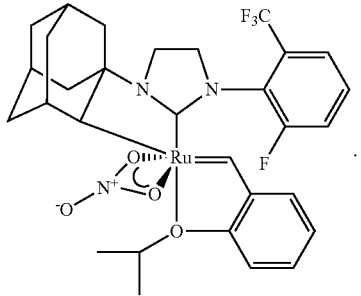

Ru-14

An example of a C—H activated catalyst complex having the structure of Formula (VII) includes the following:

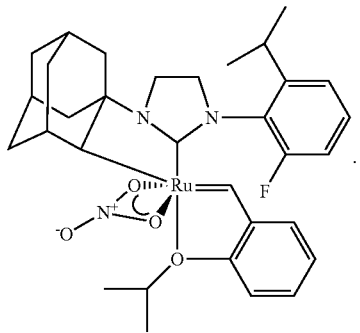

Ru-17

Asymmetric Ring Closing Metathesis (ARCM)

The Asymmetric Ring Closing Metathesis reactions catalyzed by the complexes described above involve an olefin reactant comprising three terminal olefins (i.e., an all-terminal triene), where the olefin reactant is contacted with a catalytically effective amount of the complex, under conditions and for a time period effective to allow the ARCM reaction to occur. In general, the olefin reactant comprising three terminal olefins may be represented by the structure of Formula (1):

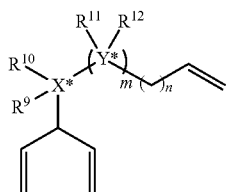

Formula (1)

wherein,
X* is an element independently selected from B, C, N, O, Si, P, S;
Y* is an element independently selected from B, C, N, O, Si, P, S;
n is 1, 2, 3, or 4;
m is zero or 1;

$R^9$, $R^{10}$, $R^{11}$, $R^{12}$ are independently selected from hydrogen, hydrocarbyl (e.g., $C_1$-$C_{20}$ alkyl, $C_5$-$C_{24}$ aryl, $C_6$-$C_{24}$ alkaryl, $C_6$-$C_{24}$ aralkyl), substituted hydrocarbyl (e.g., substituted $C_1$-$C_{20}$ alkyl, $C_5$-$C_{24}$ aryl, $C_6$-$C_{24}$ alkaryl, $C_6$-$C_{24}$ aralkyl), heteroatom-containing hydrocarbyl (e.g., heteroatom-containing $C_1$-$C_{20}$ alkyl, $C_5$-$C_{24}$ aryl, $C_6$-$C_{24}$ alkaryl, $C_6$-$C_{24}$ aralkyl), and substituted heteroatom-containing hydrocarbyl (e.g., substituted heteroatom-containing $C_1$-$C_{20}$ alkyl, $C_5$-$C_{24}$ aryl, $C_6$-$C_{24}$ alkaryl, $C_6$-$C_{24}$ aralkyl), and functional groups, wherein the substituent groups are selected from functional groups selected from the group consisting of halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO— alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O— alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—CN), cyanato (—O—Cl), thiocyanato (—S—C≡N), isocyanate (N═C═O), thioisocyanate (N═C═S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR═NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H)alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl);

$R^9$, $R^{10}$, $R^{11}$, $R^{12}$ and functional groups cannot contain olefinic carbon-carbon double bonds (i.e., —C=C—) or carbon-carbon triple bonds (i.e., —C≡C—);

$R^9$ and $R^{10}$ are not present when X* is O or S;

$R^{11}$ and $R^{12}$ are not present when m is 1 and Y* is O or S;

$R^9$ is not present when X* is N or P or B;

$R^{11}$ is not present when m is 1 and Y* is N or P or B; and wherein if either X* or Y* is B, N, O, P, or S, then the other of X* or Y* is selected from C or Si. $R^9$ and $R^{10}$ or $R^{11}$ and $R^{12}$ may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C=C—) or carbon-carbon triple bonds (i.e., —C≡C—).

Asymmetric Cross Metathesis (ACM)

The Asymmetric Cross Metathesis reactions catalyzed by the complexes described above involve a first olefin reactant comprising two terminal olefins (i.e., a diene) and a second olefin reactant, wherein the second olefin reactant comprises either a di-substituted (internal) olefin or a terminal olefin, wherein the first olefin reactant and the second olefin reactant are brought into contact in the presence of a catalytically effective amount of the complex, under conditions and for a time period effective to allow the ACM reaction to occur.

One example of a first olefin reactant comprising two terminal olefins (i.e., a diene) is a 1,4-diene represented by the structure of Formula (2):

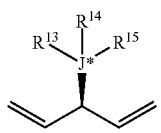

Formula (2)

wherein,

J* is an element selected from B, C, N, O, Si, P, S;

$R^{13}$, $R^{14}$, $R^{15}$ are independently selected from hydrogen, hydrocarbyl (e.g., $C_1$-$C_{20}$ alkyl, $C_5$-$C_{24}$ aryl, $C_6$-$C_{24}$ alkaryl, $C_6$-$C_{24}$ aralkyl), substituted hydrocarbyl (e.g., substituted $C_1$-$C_{20}$ alkyl, $C_5$-$C_{24}$ aryl, $C_6$-$C_{24}$ alkaryl, $C_6$-$C_{24}$ aralkyl), heteroatom-containing hydrocarbyl (e.g., heteroatom-containing $C_1$-$C_{20}$ alkyl, $C_5$-$C_{24}$ aryl, $C_6$-$C_{24}$ alkaryl, $C_6$-$C_{24}$ aralkyl), and substituted heteroatom-containing hydrocarbyl (e.g., substituted heteroatom-containing $C_1$-$C_{20}$ alkyl, $C_5$-$C_{24}$ aryl, $C_6$-$C_{24}$ alkaryl, $C_6$-$C_{24}$ aralkyl), and functional groups, wherein the substituent groups are selected from functional groups selected from the group consisting of halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO— alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O— alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO−), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—CN), cyanato (—O—C≡N), thiocyanato (—S—C≡N), isocyanate (N=C=O), thioisocyanate (N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O−), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O−)$_2$), phosphinato (—P(O)(O−)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl);

$R^{13}$, $R^{14}$, $R^{15}$, and functional groups cannot contain olefinic carbon-carbon double bonds (i.e., —C=C—) or carbon-carbon triple bonds (i.e., —C≡C—);

$R^{13}$ and $R^{14}$ are not present when J* is O or S; and $R^{13}$ is not present when J* is N or P or B.

Any two of $R^{13}$, $R^{14}$, or $R^{15}$ may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C=C—) or carbon-carbon triple bonds (i.e., —C≡C—).

Another example of a first olefin reactant comprising two terminal olefins (i.e., a diene) is a 1,5-diene represented by the structure of Formula (3):

Formula (3)

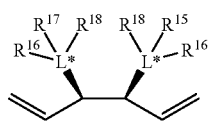

wherein,

L* is an element selected from B, C, N, O, Si, P, S;

$R^{16}$, $R^{17}$, $R^{18}$ are independently selected from hydrogen, hydrocarbyl (e.g., $C_1$-$C_{20}$ alkyl, $C_5$-$C_{24}$ aryl, $C_6$-$C_{24}$ alkaryl, $C_6$-$C_{24}$ aralkyl), substituted hydrocarbyl (e.g., substituted $C_1$-$C_{20}$ alkyl, $C_5$-$C_{24}$ aryl, $C_6$-$C_{24}$ alkaryl, $C_6$-$C_{24}$ aralkyl), heteroatom-containing hydrocarbyl (e.g., heteroatom-containing $C_1$-$C_{20}$ alkyl, $C_5$-$C_{24}$ aryl, $C_6$-$C_{24}$ alkaryl, $C_6$-$C_{24}$ aralkyl), and substituted heteroatom-containing hydrocarbyl (e.g., substituted heteroatom-containing $C_1$-$C_{20}$ alkyl, $C_5$-$C_{24}$ aryl, $C_6$-$C_{24}$ alkaryl, $C_6$-$C_{24}$ aralkyl), and functional groups, wherein the substituent groups are selected from functional groups selected from the group consisting of halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO— alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O— alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—NH_2), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)_2), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)_2), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)_2), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH_2), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)_2), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)_2), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH_2), cyano (—CN), cyanato (—O—Cl), thiocyanato (—S—C≡N), isocyanate (N═C═O), thioisocyanate (N═C═S), formyl (—(CO)—H), thioformyl (—(CS)—H), amino (—NH_2), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)_2), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)_2), $C_2$-$C_{24}$ alkylamido (—NH—(CO)-alkyl), $C_6$-$C_{24}$ arylamido (—NH—(CO)-aryl), imino (—CR═NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO_2), nitroso (—NO), sulfo (—SO_2—OH), sulfonato (—SO_2—O⁻), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO_2-alkyl), $C_1$-$C_{24}$ monoalkylaminosulfonyl (—SO_2—N(H) alkyl), $C_1$-$C_{24}$ dialkylaminosulfonyl (—SO_2—N(alkyl)_2), $C_5$-$C_{24}$ arylsulfonyl (—SO_2-aryl), boryl (—BH_2), borono (—B(OH)_2), boronato (—B(OR)_2 where R is alkyl or aryl), phosphono (—P(O)(OH)_2), phosphonato (—P(O)(O⁻)_2), phosphinato (—P(O)(O⁻)), phospho (—PO_2), and phosphino (—PH_2); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl);

$R^{16}$, $R^{17}$, $R^{18}$, and functional groups cannot contain olefinic carbon-carbon double bonds (i.e., —C═C—) or carbon-carbon triple bonds (i.e., —C≡C—);

$R^{16}$ and $R^{17}$ are not present when L* is O or S; and $R^{16}$ is not present when L* is N or P or B.

Any two of $R^{16}$, $R^{17}$, or $R^{18}$ may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C═C—) or carbon-carbon triple bonds (i.e., —C≡C—).

Another example of a first olefin reactant comprising two terminal olefins (i.e., a diene) is a 1,5-diene represented by the structure of Formula (4):

Formula (4)

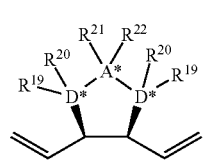

wherein,

D* is an element selected from B, C, Si;

A* is an element selected from C, N, O, P, S;

$R^{19}$, $R^{20}$, $R^{21}$, $R^{22}$ are independently selected from hydrogen, hydrocarbyl (e.g., $C_1$-$C_{20}$ alkyl, $C_5$-$C_{24}$ aryl, $C_6$-$C_{24}$ alkaryl, $C_6$-$C_{24}$ aralkyl), substituted hydrocarbyl (e.g., substituted $C_1$-$C_{20}$ alkyl, $C_5$-$C_{24}$ aryl, $C_6$-$C_{24}$ alkaryl, $C_6$-$C_{24}$ aralkyl), heteroatom-containing hydrocarbyl (e.g., heteroatom-containing $C_1$-$C_{20}$ alkyl, $C_5$-$C_{24}$ aryl, $C_6$-$C_{24}$ alkaryl, $C_6$-$C_{24}$ aralkyl), and substituted heteroatom-containing hydrocarbyl (e.g., substituted heteroatom-containing $C_1$-$C_{20}$ alkyl, $C_5$-$C_{24}$ aryl, $C_6$-$C_{24}$ alkaryl, $C_6$-$C_{24}$ aralkyl), and functional groups, wherein the substituent groups are selected from functional groups selected from the group consisting of halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—NH_2), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)_2), mono-($C_1$-$C_{24}$ halo alkyl)-substituted carbamoyl (—(CO)—NH(C$_1$-C$_{24}$ halo alkyl)), di-(C$_1$-C$_{24}$ haloalkyl)-substituted carbamoyl (—(CO)—N(C$_1$-C$_{24}$ haloalkyl)$_2$), mono-(C$_5$-C$_{24}$ aryl)-substituted carbamoyl (—(CO)—NH-aryl), di-(C$_5$-C$_{24}$ aryl)-substituted carbamoyl (—(CO)—N(C$_5$-C$_{24}$ aryl)$_2$), di-N—(C$_1$-C$_{24}$ alkyl), N—(C$_5$-C$_{24}$ aryl)-substituted carbamoyl (—(CO)—N(C$_1$-C$_{24}$ alkyl)(C$_5$-C$_{24}$ aryl), thiocarbamoyl (—(CS)—NH$_2$), mono-(C$_1$-C$_{24}$ alkyl)-substituted thiocarbamoyl (—(CS)—NH(C$_1$-C$_{24}$ alkyl)), di-(C$_1$-C$_{24}$ alkyl)-substituted thiocarbamoyl (—(CS)—N(C$_1$-C$_{24}$ alkyl)$_2$), mono-(C$_5$-C$_{24}$ aryl)-substituted thiocarbamoyl (—(CS)—NH-aryl), di-(C$_5$-C$_{24}$ aryl)-substituted thiocarbamoyl (—(CS)—N(C$_5$-C$_{24}$ aryl)$_2$), di-N—(C$_1$-C$_{24}$ alkyl), N—(C$_5$-C$_{24}$ aryl)-substituted thiocarbamoyl (—(CS)—N(C$_1$-C$_{24}$ alkyl)(C$_5$-C$_{24}$ aryl), carbamido (—NH—(CO)—NH$_2$), cyano (—CN), cyanato (—O—C≡N), thiocyanato (—S—C≡N), isocyanate (N═C═O), thioisocyanate (N═C═S), formyl (—(CO)—H), thioformyl (—(CS)—H), amino (—NH$_2$), mono-(C$_1$-C$_{24}$ alkyl)-substituted amino (—NH(C$_1$-C$_{24}$ alkyl), di-(C$_1$-C$_{24}$ alkyl)-substituted amino (—N(C$_1$-C$_{24}$ alkyl)$_2$), mono-(C$_5$-C$_{24}$ aryl)-substituted amino (—NH(C$_5$-C$_{24}$ aryl), di-(C$_5$-C$_{24}$ aryl)-substituted amino (—N(C$_5$-C$_{24}$ aryl)$_2$), C$_2$-C$_{24}$ alkylamido (—NH—(CO)-alkyl), C$_6$-C$_{24}$ arylamido (—NH—(CO)-aryl), imino (—CR═NH where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR═N(alkyl), where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR═N(aryl), where R includes without limitation hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl (—SO$_2$—N(H) alkyl), C$_1$-C$_{24}$ dialkylaminosulfonyl (—SO$_2$—N(alkyl)$_2$), C$_5$-C$_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties C$_1$-C$_{24}$ alkyl (preferably C$_1$-C$_{12}$ alkyl, more preferably C$_1$-C$_6$ alkyl), C$_5$-C$_{24}$ aryl (preferably C$_5$-C$_{14}$ aryl), C$_6$-C$_{24}$ alkaryl (preferably C$_6$ alkaryl), and C$_6$-C$_{24}$ aralkyl (preferably C$_6$-C$_{16}$ aralkyl);

R$^{19}$ is not present when D* is B;

R$^{21}$ and R$^{22}$ are not present when A* is O or S; and

R$^{21}$ is not present when A* is N or P.

R$^{19}$ and R$^{20}$ connected to the same D* may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C═C—) or carbon-carbon triple bonds (i.e., —C≡C—). R$^{21}$ and R$^{22}$ may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C═C—) or carbon-carbon triple bonds (i.e., —C≡C—).

Another example of a first olefin reactant comprising two terminal olefins (i.e., a diene) is a 1,6-diene represented by the structure of Formula (5):

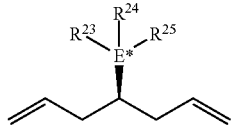

Formula (5)

wherein,

E* is an element selected from B, C, N, O, Si, P, S;

R$^{23}$, R$^{24}$, R$^{25}$ are independently selected from hydrogen, hydrocarbyl (e.g., C$_1$-C$_{20}$ alkyl, C$_5$-C$_{24}$ aryl, C$_6$-C$_{24}$ alkaryl, C$_6$-C$_{24}$ aralkyl), substituted hydrocarbyl (e.g., substituted C$_1$-C$_{20}$ alkyl, C$_5$-C$_{24}$ aryl, C$_6$-C$_{24}$ alkaryl, C$_6$-C$_{24}$ aralkyl), heteroatom-containing hydrocarbyl (e.g., heteroatom-containing C$_1$-C$_{20}$ alkyl, C$_5$-C$_{24}$ aryl, C$_6$-C$_{24}$ alkaryl, C$_6$-C$_{24}$ aralkyl), and substituted heteroatom-containing hydrocarbyl (e.g., substituted heteroatom-containing C$_1$-C$_{20}$ alkyl, C$_5$-C$_{24}$ aryl, C$_6$-C$_{24}$ alkaryl, C$_6$-C$_{24}$ aralkyl), and functional groups, wherein the substituent groups are selected from functional groups selected from the group consisting of halo, hydroxyl, sulfhydryl, C$_1$-C$_{24}$ alkoxy, C$_5$-C$_{24}$ aryloxy, C$_6$-C$_{24}$ aralkyloxy, C$_6$-C$_{24}$ alkaryloxy, acyl (including C$_2$-C$_{24}$ alkylcarbonyl (—CO— alkyl) and C$_6$-C$_{24}$ arylcarbonyl (—CO-aryl)), acyloxy (—O-acyl, including C$_2$-C$_{24}$ alkylcarbonyloxy (—O—CO-alkyl) and C$_6$-C$_{24}$ arylcarbonyloxy (—O—CO-aryl)), C$_2$-C$_{24}$ alkoxycarbonyl (—(CO)—O— alkyl), C$_6$-C$_{24}$ aryloxycarbonyl (—(CO)—O-aryl), halocarbonyl (—CO)—X where X is halo), C$_2$-C$_{24}$ alkylcarbonato (—O—(CO)—O-alkyl), C$_6$-C$_{24}$ arylcarbonato (—O—(CO)—O-aryl), carboxy (—COOH), carboxylato (—COO$^-$), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-(C$_1$-C$_{24}$ halo alkyl)-substituted carbamoyl (—(CO)—NH(C$_1$-C$_{24}$ halo alkyl)), di-(C$_1$-C$_{24}$ haloalkyl)-substituted carbamoyl (—(CO)—N(C$_1$-C$_{24}$ haloalkyl)$_2$), mono-(C$_5$-C$_{24}$ aryl)-substituted carbamoyl (—(CO)—NH-aryl), di-(C$_5$-C$_{24}$ aryl)-substituted carbamoyl (—(CO)—N(C$_5$-C$_{24}$ aryl)$_2$), di-N—(C$_1$-C$_{24}$ alkyl), N—(C$_5$-C$_{24}$ aryl)-substituted carbamoyl (—(CO)—N(C$_1$-C$_{24}$ alkyl)(C$_5$-C$_{24}$ aryl), thiocarbamoyl (—(CS)—NH$_2$), mono-(C$_1$-C$_{24}$ alkyl)-substituted thiocarbamoyl (—(CS)—NH(C$_1$-C$_{24}$ alkyl)), di-(C$_1$-C$_{24}$ alkyl)-substituted thiocarbamoyl (—(CS)—N(C$_1$-C$_{24}$ alkyl)$_2$), mono-(C$_5$-C$_{24}$ aryl)-substituted thiocarbamoyl (—(CS)—NH-aryl), di-(C$_5$-C$_{24}$ aryl)-substituted thiocarbamoyl (—(CS)—N(C$_5$-C$_{24}$ aryl)$_2$), di-N—(C$_1$-C$_{24}$ alkyl), N—(C$_5$-C$_{24}$ aryl)-substituted thiocarbamoyl (—(CS)—N(C$_1$-C$_{24}$ alkyl)(C$_5$-C$_{24}$ aryl), carbamido (—NH—(CO)—NH$_2$), cyano (—CN), cyanato (—O—Cl), thiocyanato (—S—C≡N), isocyanate (N═C═O), thioisocyanate (N═C═S), formyl (—(CO)—H), thioformyl (—(CS)—H), amino (—NH$_2$), mono-(C$_1$-C$_{24}$ alkyl)-substituted amino (—NH(C$_1$-C$_{24}$ alkyl), di-(C$_1$-C$_{24}$ alkyl)-substituted amino (—N(C$_1$-C$_{24}$ alkyl)$_2$), mono-(C$_5$-C$_{24}$ aryl)-substituted amino (—NH(C$_5$-C$_{24}$ aryl), di-(C$_5$-C$_{24}$ aryl)-substituted amino (—N(C$_5$-C$_{24}$ aryl)$_2$), C$_2$-C$_{24}$ alkylamido (—NH—(CO)-alkyl), C$_6$-C$_{24}$ arylamido (—NH—(CO)-aryl), imino (—CR═NH where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR═N(alkyl), where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR═N(aryl), where R includes without limitation hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO₂—OH), sulfonato (—SO₂—O⁻), C₁-C₂₄ alkylsulfanyl (—S-alkyl; also termed "alkylthio"), C₅-C₂₄ arylsulfanyl (—S-aryl; also termed "arylthio"), C₁-C₂₄ alkylsulfinyl (—(SO)-alkyl), C₅-C₂₄ arylsulfinyl (—(SO)-aryl), C₁-C₂₄ alkylsulfonyl (—SO₂-alkyl), C₁-C₂₄ monoalkylaminosulfonyl (—SO₂—N(H) alkyl), C₁-C₂₄ dialkylaminosulfonyl (—SO₂—N(alkyl)₂), C₅-C₂₄ arylsulfonyl (—SO₂-aryl), boryl (—BH₂), borono (—B(OH)₂), boronato (—B(OR)₂ where R is alkyl or aryl), phosphono (—P(O)(OH)₂), phosphonato (—P(O)(O⁻)₂), phosphinato (—P(O)(O⁻)), phospho (—PO₂), and phosphino (—PH₂); and the hydrocarbyl moieties C₁-C₂₄ alkyl (preferably C₁-C₁₂ alkyl, more preferably C₁-C₆ alkyl), C₅-C₂₄ aryl (preferably C₅-C₁₄ aryl), C₆-C₂₄ alkaryl (preferably C₆-C₁₆ alkaryl), and C₆-C₂₄ aralkyl (preferably C₆-C₁₆ aralkyl);

R²³, R²⁴, R²⁵, and functional groups cannot contain olefinic carbon-carbon double bonds (i.e., —C═C—) or carbon-carbon triple bonds (i.e., —C≡C—);

R²³ and R²⁴ are not present when E* is O or S; and

R²³ is not present when E* is N or P or B.

Any two of R²³, R²⁴, or R²⁵ may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C═C—) or carbon-carbon triple bonds (i.e., —C≡C—).

Another example of a first olefin reactant comprising two terminal olefins (i.e., a diene) is a 1,6-diene represented by the structure of Formula (6):

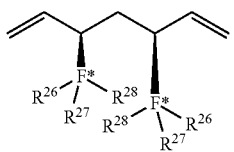

Formula (6)

wherein,

F* is an element selected from B, C, N, O, Si, P, S;

R²⁶, R²⁷, R²⁸ are independently selected from hydrogen, hydrocarbyl (e.g., C₁-C₂₀ alkyl, C₅-C₂₄ aryl, C₆-C₂₄ alkaryl, C₆-C₂₄ aralkyl), substituted hydrocarbyl (e.g., substituted C₁-C₂₀ alkyl, C₅-C₂₄ aryl, C₆-C₂₄ alkaryl, C₆-C₂₄ aralkyl), heteroatom-containing hydrocarbyl (e.g., heteroatom-containing C₁-C₂₀ alkyl, C₅-C₂₄ aryl, C₆-C₂₄ alkaryl, C₆-C₂₄ aralkyl), and substituted heteroatom-containing hydrocarbyl (e.g., substituted heteroatom-containing C₁-C₂₀ alkyl, C₅-C₂₄ aryl, C₆-C₂₄ alkaryl, C₆-C₂₄ aralkyl), and functional groups, wherein the substituent groups are selected from functional groups selected from the group consisting of halo, hydroxyl, sulfhydryl, C₁-C₂₄ alkoxy, C₅-C₂₄ aryloxy, C₆-C₂₄ aralkyloxy, C₆-C₂₄ alkaryloxy, acyl (including C₂-C₂₄ alkylcarbonyl (—CO— alkyl) and C₆-C₂₄ arylcarbonyl (—CO-aryl)), acyloxy (—O-acyl, including C₂-C₂₄ alkylcarbonyloxy (—O—CO-alkyl) and C₆-C₂₄ arylcarbonyloxy (—O—CO-aryl)), C₂-C₂₄ alkoxycarbonyl (—(CO)—O— alkyl), C₆-C₂₄ aryloxycarbonyl (—(CO)—O-aryl), halocarbonyl (—CO)—X where X is halo), C₂-C₂₄ alkylcarbonato (—O—(CO)—O-alkyl), C₆-C₂₄ arylcarbonato (—O—(CO)—O-aryl), carboxy (—COOH), carboxylato (—COO⁻), carbamoyl (—(CO)—NH₂), mono-(C₁-C₂₄ alkyl)-substituted carbamoyl (—(CO)—NH(C₁-C₂₄ alkyl)), di-(C₁-C₂₄ alkyl)-substituted carbamoyl (—(CO)—N(C₁-C₂₄ alkyl)₂), mono-(C₁-C₂₄ halo alkyl)-substituted carbamoyl (—(CO)—NH(C₁-C₂₄ halo alkyl)), di-(C₁-C₂₄ haloalkyl)-substituted carbamoyl (—(CO)—N(C₁-C₂₄ haloalkyl)₂), mono-(C₅-C₂₄ aryl)-substituted carbamoyl (—(CO)—NH-aryl), di-(C₅-C₂₄ aryl)-substituted carbamoyl (—(CO)—N(C₅-C₂₄ aryl)₂), di-N—(C₁-C₂₄ alkyl), N—(C₅-C₂₄ aryl)-substituted carbamoyl (—(CO)—N(C₁-C₂₄ alkyl)(C₅-C₂₄ aryl), thiocarbamoyl (—(CS)—NH₂), mono-(C₁-C₂₄ alkyl)-substituted thiocarbamoyl (—(CS)—NH(C₁-C₂₄ alkyl)), di-(C₁-C₂₄ alkyl)-substituted thiocarbamoyl (—(CS)—N(C₁-C₂₄ alkyl)₂), mono-(C₅-C₂₄ aryl)-substituted thiocarbamoyl (—(CS)—NH-aryl), di-(C₅-C₂₄ aryl)-substituted thiocarbamoyl (—(CS)—N(C₅-C₂₄ aryl)₂), di-N—(C₁-C₂₄ alkyl), N—(C₅-C₂₄ aryl)-substituted thiocarbamoyl (—(CS)—N(C₁-C₂₄ alkyl)(C₅-C₂₄ aryl), carbamido (—NH—(CO)—NH₂), cyano (—CN), cyanato (—O—CI), thiocyanato (—S—C≡N), isocyanate (N═C═O), thioisocyanate (N═C═S), formyl (—(CO)—H), thioformyl (—(CS)—H), amino (—NH₂), mono-(C₁-C₂₄ alkyl)-substituted amino (—NH(C₁-C₂₄ alkyl), di-(C₁-C₂₄ alkyl)-substituted amino (—N(C₁-C₂₄ alkyl)₂), mono-(C₅-C₂₄ aryl)-substituted amino (—NH(C₅-C₂₄ aryl), di-(C₅-C₂₄ aryl)-substituted amino (—N(C₅-C₂₄ aryl)₂), C₂-C₂₄ alkylamido (—NH—(CO)-alkyl), C₆-C₂₄ arylamido (—NH—(CO)-aryl), imino (—CR═NH where R includes without limitation hydrogen, C₁-C₂₄ alkyl, C₅-C₂₄ aryl, C₆-C₂₄ alkaryl, C₆-C₂₄ aralkyl, etc.), C₂-C₂₀ alkylimino (—CR═N(alkyl), where R includes without limitation hydrogen, C₁-C₂₄ alkyl, C₅-C₂₄ aryl, C₆-C₂₄ alkaryl, C₆-C₂₄ aralkyl, etc.), arylimino (—CR═N(aryl), where R includes without limitation hydrogen, C₁-C₂₀ alkyl, C₅-C₂₄ aryl, C₆-C₂₄ alkaryl, C₆-C₂₄ aralkyl, etc.), nitro (—NO₂), nitroso (—NO), sulfo (—SO₂—OH), sulfonato (—SO₂—O⁻), C₁-C₂₄ alkylsulfanyl (—S-alkyl; also termed "alkylthio"), C₅-C₂₄ arylsulfanyl (—S-aryl; also termed "arylthio"), C₁-C₂₄ alkylsulfinyl (—(SO)-alkyl), C₅-C₂₄ arylsulfinyl (—(SO)-aryl), C₁-C₂₄ alkylsulfonyl (—SO₂-alkyl), C₁-C₂₄ monoalkylaminosulfonyl (—SO₂—N(H) alkyl), C₁-C₂₄ dialkylaminosulfonyl (—SO₂—N(alkyl)₂), C₅-C₂₄ arylsulfonyl (—SO₂-aryl), boryl (—BH₂), borono (—B(OH)₂), boronato (—B(OR)₂ where R is alkyl or aryl), phosphono (—P(O)(OH)₂), phosphonato (—P(O)(O⁻)₂), phosphinato (—P(O)(O⁻)), phospho (—PO₂), and phosphino (—PH₂); and the hydrocarbyl moieties C₁-C₂₄ alkyl (preferably C₁-C₁₂ alkyl, more preferably C₁-C₆ alkyl), C₅-C₂₄ aryl (preferably C₅-C₁₄ aryl), C₆-C₂₄ alkaryl (preferably C₆-C₁₆ alkaryl), and C₆-C₂₄ aralkyl (preferably C₆-C₁₆ aralkyl);

R²⁶, R²⁷, R²⁸, and functional groups cannot contain olefinic carbon-carbon double bonds (i.e., —C═C—) or carbon-carbon triple bonds (i.e., —C≡C—);

R²⁶ and R²⁷ are not present when F* is O or S; and

R²⁶ is not present when F* is N or P or B.

Any two of R²⁶, R²⁷, or R²⁸ may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C═C—) or carbon-carbon triple bonds (i.e., —C≡C—).

Another example of a first olefin reactant comprising two terminal olefins (i.e., a diene) is a 1,6-diene represented by the structure of Formula (7):

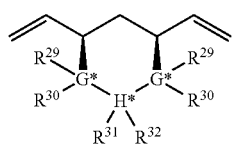

Formula (7)

wherein,

G* is an element selected from B, C, Si;

H* is an element selected form C, N, O, P, S;

$R^{29}$, $R^{30}$, $R^{31}$, $R^{32}$ are independently selected from hydrogen, hydrocarbyl (e.g., $C_1$-$C_{20}$ alkyl, $C_5$-$C_{24}$ aryl, $C_6$-$C_{24}$ alkaryl, $C_6$-$C_{24}$ aralkyl), substituted hydrocarbyl (e.g., substituted $C_1$-$C_{20}$ alkyl, $C_5$-$C_{24}$ aryl, $C_6$-$C_{24}$ alkaryl, $C_6$-$C_{24}$ aralkyl), heteroatom-containing hydrocarbyl (e.g., heteroatom-containing $C_1$-$C_{20}$ alkyl, $C_5$-$C_{24}$ aryl, $C_6$-$C_{24}$ alkaryl, $C_6$-$C_{24}$ aralkyl), and substituted heteroatom-containing hydrocarbyl (e.g., substituted heteroatom-containing $C_1$-$C_{20}$ alkyl, $C_5$-$C_{24}$ aryl, $C_6$-$C_{24}$ alkaryl, $C_6$-$C_{24}$ aralkyl), and functional groups, wherein the substituent groups are selected from functional groups selected from the group consisting of halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo, $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—CN), cyanato (—O—C≡N), thiocyanato (—S—C≡N), isocyanate (N=C=O), thioisocyanate (N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl);

$R^{29}$ is not present when G* is B;

$R^{31}$ and $R^{32}$ are not present when H* is O or S; and $R^{31}$ is not present when H* is N or P.

$R^{29}$ and $R^{30}$ connected to the same G* may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C=C—) or carbon-carbon triple bonds (i.e., —C≡C—). $R^{31}$ and $R^{32}$ may also be linked to form a cyclic group, which may be aliphatic or aromatic, and may contain substituents and/or heteroatoms. Generally, such a cyclic group will contain 4 to 12, preferably 5, 6, 7, or 8 ring atoms. The cyclic group and any substituents cannot contain olefinic carbon-carbon double bonds (i.e., —C=C—) or carbon-carbon triple bonds (i.e., —C≡C—).

In general the second olefin reactant comprising a terminal olefin may be represented by the structure of Formula (8):

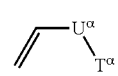

Formula (8)

wherein, $U^\alpha$ is selected from the group comprising nil, CH$_2$, O, or S; and $T^\alpha$ is selected from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge).

In another example the second olefin reactant comprising a terminal olefin may be represented by the structure of Formula (9):

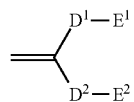

Formula (9)

wherein $D^1$ and $D^2$ are independently selected from nil, $CH_2$, O, or S; and $E^1$ and $E^2$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (N═C═O), thioisocyanate (N═C═S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR═NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N (alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Moreover, in one embodiment, for an olefin reactant comprising a reactant terminal olefin represented by the structure of Formula (9), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—CF), fluroaryl (e.g., —C6F5, p-CF$_3$C$_6$H$_4$), cyano (—CN), sulfoxide (—SOR), sulfonyl (—SO$_2$R), sulfonic acid (—SO$_3$H), phthalamide, 1°, 2° and 3° ammonium (—NR$_3^+$), or nitro (—NO$_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1°, 2° and 3° ammonium (—NR$_3^+$), nitro (—NO$_2$), or phthalamide.

In one embodiment, for an olefin reactant comprising a reactant terminal olefin represented by the structure of Formula (9), where if $E^1$ and $E^2$ are the same, then $D^1$ and $D^2$ must be different, and if $D^1$ and $D^2$ are the same then $E^1$ and $E^2$ must be different.

In general the second olefin reactant comprising a di-substituted (internal) olefin may be represented by the structure of Formula (10):

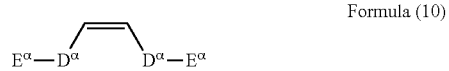

Formula (10)

wherein, $D^\alpha$ is selected from the group comprising nil, $CH_2$, O, or S; and $E^\alpha$ is selected from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge).

In another example the second olefin reactant comprising a di-substituted (internal) olefin may be represented by the structure of Formula (11):

Formula (11)

wherein, $D^{11}$ and $D^{12}$ are independently selected from nil, $CH_2$, O, or S; and $E^{11}$ and $E^{12}$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (N=C=O), thioisocyanate (N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O⁻)$_2$), phosphinato (—P(O)(O⁻)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Moreover, in one embodiment, for an olefin reactant comprising a reactant internal olefin represented by the structure of Formula (11), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—CF$_n$), fluroaryl (e.g., —C$_6$F$_5$, p-CF$_3$C$_6$H$_4$), cyano (—CN), sulfoxide (—SOR), sulfonyl (—SO$_2$R), sulfonic acid (—SO$_3$H), phthalamide, 1°, 2° and 3° ammonium (—NR$_3^+$), or nitro (—NO$_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—$SO_3H$), 1°, 2° and 3° ammonium (—$NR_3^+$), nitro (—$NO_2$), or phthalamide.

In one embodiment, for an olefin reactant comprising a reactant internal olefin represented by the structure of Formula (11), where if $E^{11}$ is hydrogen, then $D^{11}$ cannot be nil; and where if $E^{12}$ is hydrogen, then $D^{12}$ cannot be nil.

In a further example the second di-substituted olefin reactant comprising a reactant internal olefin may be represented by the structure of Formula (12):

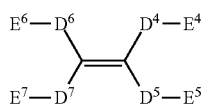

Formula (12)

wherein, $D^4$, $D^5$, $D^6$, and $D^7$ are independently selected from nil, $CH_2$, O, or S; and $E^4$, $E^5$, $E^6$, and $E^7$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—$COO^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—$NH_2$), cyano (—C≡N), cyanato (—O—C≡N), thiocyanato (—S—C≡N), isocyanate (N=C=O), thioisocyanate (N=C=S), formyl (—(CO)—H), thioformyl (—(CS)—H), amino (—$NH_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl (—$SO_2$—N(H) alkyl), $C_1$-$C_{24}$ dialkylaminosulfonyl (—$SO_2$—N(alkyl)$_2$), $C_5$-$C_{24}$ arylsulfonyl (—$SO_2$-aryl), boryl (—$BH_2$), borono (—B(OH)$_2$), boronato (—B(OR)$_2$ where R is alkyl or aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Moreover, in one embodiment, for an olefin reactant comprising a reactant internal olefin represented by the structure of Formula (12), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—$NRSO_2Ar$), carbamate (—$NCO_2R$), epoxide (e.g., epoxybutadiene), halides (—Cl, —F, —Br, —I), fluoromethyl (—$CF_n$), fluoraryl (e.g., —$C_6F_5$, p-$CF_3C_6H_4$), cyano (—CN), sulfoxide (—SOR), sulfonyl (—$SO_2R$), sulfonic acid (—$SO_3H$), phthalamide, 1°, 2° and 3° ammonium (—$NR_3^+$), or nitro (—$NO_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—$NRSO_2Ar$), carbamate (—$NCO_2R$), sulfonyl (—$SO_2R$), fluoromethyl (—$CF_n$), fluoraryl (e.g., —$C_6F_5$, p-$CF_3C_6H_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—$SO_3H$), 1°, 2° and 3° ammonium (—$NR_{31}$, nitro (—$NO_2$), or phthalamide.

In one embodiment, for an olefin reactant comprising a reactant internal olefin represented by the structure of Formula (12), where if $E^4$ and $E^5$ are the same, then $D^4$ and $D^5$ must be different, and if $D^4$ and $D^5$ are the same then $E^4$ and $E^5$ must be different, and where if $E^6$ and $E^7$ are the same, then $D^6$ and $D^7$ must be different, and if $D^6$ and $D^7$ are the same then $E^6$ and $E^7$ must be different.

In one embodiment, for an olefin reactant comprising a reactant internal olefin represented by the structure of Formula (12), where if $E^4$ and $E^5$ are hydrogen, then both of $D^4$ and $D^5$ cannot be nil.

In a further example the second di-substituted olefin reactant comprising a reactant internal olefin may be represented by the structure of Formula (13):

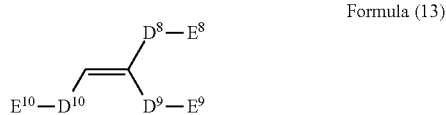

Formula (13)

wherein, $D^8$, $D^9$, and $D^{10}$ are independently selected from nil, $CH_2$, O, or S; and $E^8$, $E^9$, and $E^{10}$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—CN), cyanato (—O—C≡N), thiocyanato (—S—C≡N), isocyanate (N═C═O), thioisocyanate (N═C═S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR═NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl); and where if $E^{10}$ is hydrogen, then $D^{10}$ cannot be nil.

Moreover, in one embodiment, for an olefin reactant comprising a reactant internal olefin represented by the structure of Formula (13), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—CF$_n$), fluoroaryl (e.g., —C$_6$F$_5$, p-CF$_3$C$_6$H$_4$), cyano (—CN), sulfoxide (—SOR), sulfonyl (—SO$_2$R), sulfonic acid (—SO$_3$H), phthalamide, 1°, 2° and 3° ammonium (—NR$_3^+$), or nitro (—NO$_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluoroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1°, 2° and 3° ammonium (—NR$_3^+$), nitro (—NO$_2$), or phthalamide.

In one embodiment, for an olefin reactant comprising a reactant internal olefin represented by the structure of Formula (13), where if $E^8$ and $E^9$ are the same, then $D^8$ and $D^9$ must be different, and if $D^8$ and $D^9$ are the same then $E^8$ and $E^9$ must be different, and where if $E^{10}$ is hydrogen, then $D^{10}$ cannot be nil.

In one embodiment, for an olefin reactant comprising a reactant internal olefin represented by the structure of Formula (13), where if $E^{10}$ is hydrogen, then $D^{10}$ cannot be nil In a further embodiment the second olefin reactant comprising a di-substituted (internal) olefin may be represented by the structure of Formula (14):

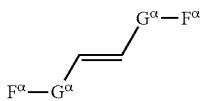

Formula (14)

wherein, $G^\alpha$ is selected from the group comprising nil, $CH_2$, O, or S; and $F^\alpha$ is selected from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge).

In a further example the second di-substituted olefin reactant comprising a reactant internal olefin may be represented by the structure of Formula (15):

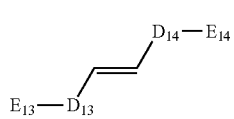

Formula (15)

wherein, $D^{13}$ and $D^{14}$ are independently selected from nil, $CH_2$, O, or S; and $E^{13}$ and $E^{14}$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—(CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl) ($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (N═C═O), thioisocyanate (N═C═S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR═NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Moreover, in one embodiment, for an olefin reactant comprising a reactant internal olefin represented by the structure of Formula (15), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—$CF_n$), fluoroaryl (e.g., —$C_6F_5$, p-$CF_3C_6H_4$), cyano (—CN), sulfoxide (—SOR), sulfonyl (—$SO_2R$), sulfonic acid (—$SO_3H$), phthalamide, 1°, 2° and 3° ammonium (—$NR_3^+$), or nitro (—$NO_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—$NRSO_2Ar$), carbamate (—$NCO_2R$), sulfonyl (—$SO_2R$), fluoromethyl (—$CF_n$), fluroaryl (e.g., —$C_6F_5$, p-$CF_3C_6H_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—$SO_3H$), 1°, 2° and 3° ammonium (—$NR_3^+$), nitro (—$NO_2$), or phthalamide.

In one embodiment, for an olefin reactant comprising a reactant internal olefin represented by the structure of Formula (15), where if $E^{13}$ is hydrogen, then $D^{13}$ cannot be nil; and where if $E^{14}$ is hydrogen, then $D^{14}$ cannot be nil.

Cross Metathesis Product Comprising a Product Internal Olefin

Generally, the cross-metathesis reactions of the invention provides at least one cross-metathesis product comprising a product internal olefin, wherein the product internal olefin is in the E-configuration or Z-configuration, preferably in the Z-configuration, wherein the at least one cross-metathesis product comprising a product internal olefin may be the same or different.

In one example an at least one cross-metathesis product comprising a product internal olefin, wherein the product internal olefin is in the Z-configuration may be represented by the structure of Formula (16):

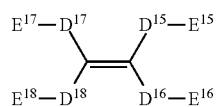

Formula (16)

wherein, $D^{15}$, $D^{16}$, $D^{17}$, and $D^{18}$ are independently selected from nil, $CH_2$, O, or S; and $E^{15}$, $E^{16}$, $E^{17}$, and $E^{18}$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—$COO^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl) ($C_5$-$C_{24}$ aryl), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—$NH_2$), cyano (—C≡N), cyanato (—O—C≡N), thiocyanato (—S—C≡N), isocyanate (N=C=O), thioisocyanate (N=C=S), formyl (—(CO)—H), thioformyl (—(CS)—H), amino (—$NH_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N (alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl (—$SO_2$—N(H) alkyl), $C_1$-$C_{24}$ dialkylaminosulfonyl (—$SO_2$—N(alkyl)$_2$), $C_5$-$C_{24}$ arylsulfonyl (—$SO_2$-aryl), boryl (—$BH_2$), borono (—B(OH)$_2$), boronato (—B(OR)$_2$ where R is alkyl or aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Moreover, in one embodiment, for at least one cross-metathesis product comprising a product internal olefin represented by the structure of Formula (16), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—$NRSO_2Ar$), carbamate (—$NCO_2R$), epoxide (e.g., epoxybutadiene), halides (—Cl, —F, —Br, —I), fluoromethyl (—$CF_n$), fluroaryl (e.g., —$C_6F_5$, p-$CF_3C_6H_4$), cyano (—CN), sulfoxide (—SOR), sulfonyl (—$SO_2$R), sulfonic acid (—$SO_3$H), phthalamide, 1°, 2° and 3° ammonium (—$NR_3^+$), or nitro (—$NO_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—$NRSO_2$Ar), carbamate (—$NCO_2$R), sulfonyl (—$SO_2$R), fluoromethyl (—$CF_n$), fluroaryl (e.g., —$C_6F_5$, p-$CF_3C_6H_4$), epoxide (e.g., epoxybutadiene), or cyano (—CN), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—$SO_3$H), 1°, 2° and 3° ammonium (—$NR_3^+$), nitro (—$NO_2$), or phthalamide.

In one embodiment, for at least one cross-metathesis product comprising a product internal olefin represented by the structure of Formula (16), where if $E^{15}$ and $E^{16}$ are the same, then $D^{15}$ and $D^{16}$ must be different, and if $D^{15}$ and $D^{16}$ are the same then $E^{15}$ and $E^{16}$ must be different, and where if $E^{17}$ and $E^{18}$ are the same, then $D^{17}$ and $D^{18}$ must be different, and if $D^{17}$ and $D^{18}$ are the same then $E^{17}$ and $E^{18}$ must be different.

In another example an at least one cross-metathesis product comprising a product internal olefin, wherein the product internal olefin is in the Z-configuration may be represented by the structure of Formula (17):

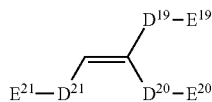

Formula (17)

wherein, $D^{19}$, $D^{20}$, and $D^{21}$ are independently selected from nil, $CH_2$, O, or S; and $E^{19}$, $E^{20}$, and $E^{21}$ are independently selected from hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as halo, hydroxyl, sulfhydryl, $C_1$-$C_{24}$ alkoxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—(CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ halo alkyl)-substituted carbamoyl (—(CO)—NH($C_1$-$C_{24}$ halo alkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl) ($C_5$-$C_{24}$ aryl), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—$NH_2$), cyano (—C≡N), cyanato (—O—C≡N), thiocyanato (—S—C≡N), isocyanate (N=C=O), thioisocyanate (N=C=S), formyl (—(CO)—H), thioformyl (—(CS)—H), amino (—$NH_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—O⁻), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl (—$SO_2$—N(H) alkyl), $C_1$-$C_{24}$ dialkylaminosulfonyl (—$SO_2$—N(alkyl)$_2$), $C_5$-$C_{24}$ arylsulfonyl (—$SO_2$-aryl), boryl (—$BH_2$), borono (—B(OH)$_2$), boronato (—B(OR)$_2$ where R is alkyl or aryl), phosphono (—P(O)(OH)$_2$), phosphonato (—P(O)(O⁻)$_2$), phosphinato (—P(O)(O⁻)), phospho (—$PO_2$), and phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Moreover, in one embodiment, for at least one cross-metathesis product comprising a product internal olefin represented by the structure of Formula (17), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—$NRSO_2$Ar), carbamate (—$NCO_2$R), epoxide (e.g., epoxybutadiene), halides (—Cl, —F, —Br, —I), fluoromethyl (—$CF_n$), fluroaryl (e.g., —$C_6F_5$, p-$CF_3C_6H_4$), cyano (—CN), sulfoxide (—SOR), sulfonyl (—$SO_2$R), sulfonic acid (—$SO_3$H), phthalamide, 1°, 2° and 3° ammonium (—$NR_3^+$), or nitro (—$NO_2$), wherein n is 1, 2, or 3, and R is a hydrogen, methyl, substituted $C_2$-$C_6$ alkyl, unsubstituted $C_2$-$C_6$ alkyl, substituted aryl, or unsubstituted aryl. Examples of electron withdrawing groups of various embodiments include ester (—OCOR), sulfonamide (—$NRSO_2$Ar), carbamate (—$NCO_2$R), sulfonyl (—$SO_2$R), fluoromethyl (—$CF_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1°, 2° and 3° ammonium (—NR$_3^+$), nitro (—NO$_2$), or phthalamide.

In a further embodiment, for at least one cross-metathesis product comprising a product internal olefin represented by the structure of Formula (17), where if E$^{19}$ and E$^{20}$ are the same, then D$^{19}$ and D$^{20}$ must be different, and if D$^{19}$ and D$^{20}$ are the same then E$^{19}$ and E$^{20}$ must be different, and where if E$^{21}$ is hydrogen, then D$^{21}$ cannot be nil.

In another embodiment, for at least one cross-metathesis product comprising a product internal olefin represented by the structure of Formula (17), where if E$^{21}$ is hydrogen, then D$^{21}$ cannot be nil.

In another example, an at least one cross-metathesis product comprising a product internal olefin, wherein the product internal olefin is in the Z-configuration may be represented by the structure of Formula (18):

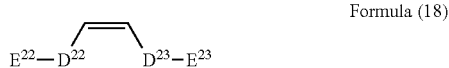

Formula (18)

wherein,

D$^{22}$ and D$^{23}$ are independently selected from nil, CH$_2$, O, or S; and

E$^{22}$ and E$^{23}$ are independently selected from hydrogen, hydrocarbyl (e.g., C$_1$-C$_{20}$ alkyl, C$_5$-C$_{20}$ aryl, C$_5$-C$_{30}$ aralkyl, or C$_5$-C$_{30}$ alkaryl), substituted hydrocarbyl (e.g., substituted C$_1$-C$_{20}$ alkyl, C$_5$-C$_{20}$ aryl, C$_5$-C$_{30}$ aralkyl, or C$_5$-C$_{30}$ alkaryl), heteroatom-containing hydrocarbyl (e.g., C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl), and substituted heteroatom-containing hydrocarbyl (e.g., substituted C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl) and, if substituted hydrocarbyl or substituted heteroatom-containing hydrocarbyl, wherein the substituents may be functional groups ("Fn") such as halo, hydroxyl, sulfhydryl, C$_1$-C$_{24}$ alkoxy, C$_5$-C$_{24}$ aryloxy, C$_6$-C$_{24}$ aralkyloxy, C$_6$-C$_{24}$ alkaryloxy, acyl (including C$_2$-C$_{24}$ alkylcarbonyl (—CO-alkyl) and C$_6$-C$_{24}$ arylcarbonyl (—CO-aryl)), acyloxy (—O-acyl, including C$_2$-C$_{24}$ alkylcarbonyloxy (—O—CO-alkyl) and C$_6$-C$_{24}$ arylcarbonyloxy (—O—CO-aryl)), C$_2$-C$_{24}$ alkoxycarbonyl (—(CO)—O-alkyl), C$_6$-C$_{24}$ aryloxycarbonyl (—(CO)—O-aryl), halocarbonyl (—CO)—X where X is halo), C$_2$-C$_{24}$ alkylcarbonato (—O—(CO)—O-alkyl), C$_6$-C$_{24}$ arylcarbonato (—O—(CO)—O-aryl), carboxy (—COOH), carboxylato (—COO$^-$), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-(C$_1$-C$_{24}$ halo alkyl)-substituted carbamoyl (—(CO)—NH(C$_1$-C$_{24}$ halo alkyl)), di-(C$_1$-C$_{24}$ haloalkyl)-substituted carbamoyl (—(CO)—N(C$_1$-C$_{24}$ haloalkyl)$_2$), mono-(C$_5$-C$_{24}$ aryl)-substituted carbamoyl (—(CO)—NH-aryl), di-(C$_5$-C$_{24}$ aryl)-substituted carbamoyl (—(CO)—N(C$_5$-C$_{24}$ aryl)$_2$), di-N—(C$_1$-C$_{24}$ alkyl), N—(C$_5$-C$_{24}$ aryl)-substituted carbamoyl (—(CO)—N(C$_1$-C$_{24}$ alkyl) (C$_5$-C$_{24}$ aryl), thiocarbamoyl (—(CS)—NH$_2$), mono-(C$_1$-C$_{24}$ alkyl)-substituted thiocarbamoyl (—(CS)—NH(C$_1$-C$_{24}$ alkyl)), di-(C$_1$-C$_{24}$ alkyl)-substituted thiocarbamoyl (—(CS)—N(C$_1$-C$_{24}$ alkyl)$_2$), mono-(C$_5$-C$_{24}$ aryl)-substituted thiocarbamoyl (—(CS)—NH-aryl), di-(C$_5$-C$_{24}$ aryl)-substituted thiocarbamoyl (—(CS)—N(C$_5$-C$_{24}$ aryl)$_2$), di-N—(C$_1$-C$_{24}$ alkyl), N—(C$_5$-C$_{24}$ aryl)-substituted thiocarbamoyl (—(CS)—N(C$_1$-C$_{24}$ alkyl)(C$_5$-C$_{24}$ aryl), carbamido (—NH—(CO)—NH$_2$), cyano (—CN), cyanato (—O—C≡N), thiocyanato (—S—C≡N), isocyanate (N=C=O), thioisocyanate (N=C=S), formyl (—(CO)—H), thioformyl (—(CS)—H), amino (—NH$_2$), mono-(C$_1$-C$_{24}$ alkyl)-substituted amino (—NH(C$_1$-C$_{24}$ alkyl), di-(C$_1$-C$_{24}$ alkyl)-substituted amino (—N(C$_1$-C$_{24}$ alkyl)$_2$), mono-(C$_5$-C$_{24}$ aryl)-substituted amino (—NH(C$_5$-C$_{24}$ aryl), di-(C$_5$-C$_{24}$ aryl)-substituted amino (—N(C$_5$-C$_{24}$ aryl)$_2$), C$_2$-C$_{24}$ alkylamido (—NH—(CO)-alkyl), C$_6$-C$_{24}$ arylamido (—NH—(CO)-aryl), imino (—CR=NH where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), C$_2$-C$_{20}$ alkylimino (—CR=N(alkyl), where R includes without limitation hydrogen, C$_1$-C$_{24}$ alkyl, C$_5$-C$_{24}$ aryl, C$_6$-C$_{24}$ alkaryl, C$_6$-C$_{24}$ aralkyl, etc.), arylimino (—CR=N(aryl), where R includes without limitation hydrogen, C$_1$-C$_{20}$ alkyl, C$_5$-C$_{24}$ aryl, C$_6$-C$_{24}$ alkaryl, C$_6$-C$_{24}$ aralkyl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_5$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl (—SO$_2$—N(H) alkyl), C$_1$-C$_{24}$ dialkylaminosulfonyl (—SO$_2$—N(alkyl)$_2$), C$_5$-C$_{24}$ arylsulfonyl (—SO$_2$-aryl), boryl (—BH$_2$), borono (—B(OH)$_2$), boronato (—B(OR)$_2$ where R is alkyl or aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties C$_1$-C$_{24}$ alkyl (preferably C$_1$-C$_{12}$ alkyl, more preferably C$_1$-C$_6$ alkyl), C$_5$-C$_{24}$ aryl (preferably C$_5$-C$_{14}$ aryl), C$_6$-C$_{24}$ alkaryl (preferably C$_6$-C$_{16}$ alkaryl), and C$_6$-C$_{24}$ aralkyl (preferably C$_6$-C$_{16}$ aralkyl).

Moreover, in one embodiment, for at least one cross-metathesis product comprising a product internal olefin represented by the structure of Formula (18), the functional groups may be selected from electron withdrawing groups. Examples of electron withdrawing groups of various embodiments may include, but are not limited to, aldehyde (—COH), ketone (—COR), acyl (—COR), carbonyl (—CO), carboxylic acid (—COOH), ester (—COOR), ester (—OCOR), sulfonamide (—NRSO$_2$Ar), carbamate (—NCO$_2$R), epoxide (e.g., epoxybutadiene), halides (—Cl, —F, —Br, —I), fluoromethyl (—CF$_n$), fluroaryl (e.g., —C$_6$F$_5$, p-CF$_3$C$_6$H$_4$), cyano (—CN), sulfoxide (—SOR), sulfonyl (—SO$_2$R), sulfonic acid (—SO$_3$H), phthalamide, 1°, 2° and 3° ammonium (—NR$_3^+$), or nitro (—NO$_2$), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—OCOR), sulfonamide (—NRSO$_2$Ar), carbamate (—NCO$_2$R), sulfonyl (—SO$_2$R), fluoromethyl (—CF$_n$), fluroaryl (e.g., —C$_6$F$_5$, p-CF$_3$C$_6$H$_4$), epoxide (e.g., epoxybutadiene), or cyano (—CN), wherein n is 1, 2, or 3, and R is a hydrogen, methyl, substituted C$_2$-C$_6$ alkyl, unsubstituted C$_2$-C$_6$ alkyl, substituted aryl, or unsubstituted aryl. Examples of electron withdrawing groups of various embodiments include ester (—COOR), ketone (—COR), aldehyde (—COH), halides (—Cl, —F, —Br, —I), carboxylic acid (—COOH), sulfonic acid (—SO$_3$H), 1°, 2° and 3° ammonium (—NR$_3^+$), nitro (—NO$_2$), or phthalamide.

In another embodiment, for at least one cross-metathesis product comprising a product internal olefin represented by the structure of Formula (18), where if E$^{22}$ is hydrogen, then D$^{22}$ cannot be nil; and where if E$^{23}$ is hydrogen, then D$^{23}$ cannot be nil.

Asymmetric Ring Opening Cross Metathesis (AROCM)

The Asymmetric Ring Opening Cross Metathesis reactions catalyzed by the complexes described above involve a strained olefin reactant and a second α-olefin reactant, wherein the two reactants are brought into contact in the presence of a catalytically effective amount of the complex, under conditions and for a time period effective to allow the AROCM reaction to occur.

In general, the strained olefin reactant may be represented by the structure of Formula (19):

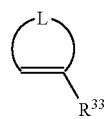

Formula (19)

wherein J and R$^{33}$ are as follows:

R$^{33}$ is selected from the group consisting of hydrogen, hydrocarbyl (e.g., C$_1$-C$_{20}$ alkyl, C$_5$-C$_{20}$ aryl, C$_5$-C$_{30}$ aralkyl, or C$_5$-C$_{30}$ alkaryl), substituted hydrocarbyl (e.g., substituted C$_1$-C$_{20}$ alkyl, C$_5$-C$_{20}$ aryl, C$_5$-C$_{30}$ aralkyl, or C$_5$-C$_{30}$ alkaryl), heteroatom-containing hydrocarbyl (e.g., C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl), and substituted heteroatom-containing hydrocarbyl (e.g., substituted C$_1$-C$_{20}$ heteroalkyl, C$_5$-C$_{20}$ heteroaryl, heteroatom-containing C$_5$-C$_{30}$ aralkyl, or heteroatom-containing C$_5$-C$_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, C$_1$-C$_{20}$ alkylsulfanyl, C$_5$-C$_{20}$ arylsulfanyl, C$_1$-C$_{20}$ alkylsulfonyl, C$_5$-C$_{20}$ arylsulfonyl, C$_1$-C$_{20}$ alkylsulfinyl, C$_5$-C$_{20}$ arylsulfinyl, sulfonamido, amino, amido, imino, nitro, nitroso, hydroxyl, C$_1$-C$_{20}$ alkoxy, C$_5$-C$_{20}$ aryloxy, C$_2$-C$_{20}$ alkoxycarbonyl, C$_5$-C$_{20}$ aryloxycarbonyl, carboxyl, carboxylato, mercapto, formyl, C$_1$-C$_{20}$ thioester, cyano, cyanato, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge). R$^{13}$ may itself be one of the aforementioned groups, such that the Fn moiety is directly bound to the olefinic carbon atom indicated in the structure. In the latter case, however, the functional group will generally not be directly bound to the olefinic carbon through a heteroatom containing one or more lone pairs of electrons, e.g., an oxygen, sulfur, nitrogen or phosphorus atom, or through an electron-rich metal or metalloid such as Ge, Sn, As, Sb, Se, Te, etc. With such functional groups, there will normally be an intervening linkage Z, such that R$^{13}$ then has the structure —(Z)$_n$—Fn wherein n is 1, Fn is the functional group, and Z is a hydrocarbylene linking group such as an alkylene, substituted alkylene, heteroalkylene, substituted heteroalkene, arylene, substituted arylene, heteroarylene, or substituted heteroarylene linkage.

J is a saturated or unsaturated hydrocarbylene, substituted hydrocarbylene, heteroatom-containing hydrocarbylene, or substituted heteroatom-containing hydrocarbylene linkage, wherein when J is substituted hydrocarbylene or substituted heteroatom-containing hydrocarbylene, the substituents may include one or more —(Z)$_n$-Fn groups, wherein n is zero or 1, and Fn and Z are as defined previously. Additionally, two or more substituents attached to ring carbon (or other) atoms within J may be linked to form a bicyclic or polycyclic olefin. J will generally contain in the range of approximately 4 to 14 ring atoms, typically 4 to 8 ring atoms, for a monocyclic olefin, and, for bicyclic and polycyclic olefins, each ring will generally contain 4 to 8, typically 5 to 7, ring atoms.

Mono-unsaturated cyclic olefin reactants encompassed by Formula (19) may be represented by the structure of Formula (20):

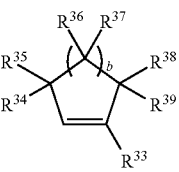

Formula (20)

wherein b is an integer generally although not necessarily in the range of 0 to 10, typically 0 to 5, R$^{33}$ is as defined above, and R$^{34}$, R$^{35}$, R$^{36}$, R$^{37}$, R$^{38}$, and R$^{39}$ are independently selected from the group consisting of hydrogen, hydrocarbyl, substituted hydrocarbyl, heteroatom-containing hydrocarbyl, substituted heteroatom-containing hydrocarbyl and —(Z)$_n$-Fn where n, Z and Fn are as defined previously, and wherein if any of the R$^{34}$ through R$^{39}$ moieties is substituted hydrocarbyl or substituted heteroatom-containing hydrocarbyl, the substituents may include one or more —(Z)$_n$-Fn groups. Accordingly, R$^{34}$, R$^{35}$, R$^{36}$, R$^{37}$, R$^{38}$, and R$^{39}$ may be, for example, hydrogen, hydroxyl, C$_1$-C$_{20}$ alkyl, C$_5$-C$_{20}$ aryl, C$_1$-C$_{20}$ alkoxy, C$_5$-C$_{20}$ aryloxy, C$_2$-C$_{20}$ alkoxycarbonyl, C$_5$-C$_{20}$ aryloxycarbonyl, amino, amido, nitro, etc. Furthermore, any of the R$^{34}$ through R$^{39}$ moieties can be linked to any other of the R$^{34}$ through R$^{39}$ moieties to provide a bicyclic or polycyclic olefin, and the linkage may include heteroatoms or functional groups, e.g., the linkage may include an ether, ester, thioether, amino, alkylamino, imino, or anhydride moiety.

Examples of monounsaturated, monocyclic olefins encompassed by Formula (20) include, without limitation, cyclopentene, cyclohexene, cycloheptene, cyclooctene, cyclononene, cyclodecene, cycloundecene, cyclododecene, tricyclodecene, tetracyclodecene, octacyclodecene, and cycloeicosene, and substituted versions thereof such as 1-methylcyclopentene, 1-ethylcyclopentene, 1-isopropylcyclohexene, 1-chloropentene, 1-fluorocyclopentene, 1-methylcyclopentene, 4-methoxy-cyclopentene, 4-ethoxy-cyclopentene, cyclopent-3-ene-thiol, cyclopent-3-ene, 4-methylsulfanyl-cyclopentene, 3-methylcyclohexene, 1-methylcyclooctene, 1,5-dimethylcyclooctene, etc.

Monocyclic diene reactants encompassed by Formula (19) may be generally represented by the structure represented by Formula (21):

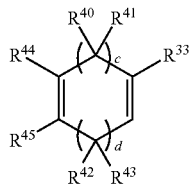

Formula (21)

wherein, c and d are independently integers in the range of 1 to about 8, typically 2 to 4, preferably 2 (such that the reactant is a cyclooctadiene), $R^{33}$ is as defined above, and $R^{40}$, $R^{41}$, $R^{42}$, $R^{43}$, $R^{44}$, and $R^{45}$ are defined as for $R^{34}$ through $R^{39}$. In this case, it is preferred that $R^{44}$ and $R^{45}$ be nonhydrogen substituents, in which case the second olefinic moiety is tetrasubstituted, so that the ROCM reaction proceeds selectively at only one of the two olefin functionalities. Examples of monocyclic diene reactants include, without limitation, 1,3-cyclopentadiene, 1,3-cyclohexadiene, 1,3-cyclohexadiene, 5-ethyl-1,3-cyclohexadiene, 1,3-cycloheptadiene, cyclohexadiene, 1,5-cyclooctadiene, 1,3-cyclooctadiene, and substituted analogs thereof. Triene reactants are analogous to the diene structure (XV), and will generally contain at least one methylene linkage between any two olefinic segments.

Bicyclic and polycyclic olefinic reactants encompassed by Formula (19) may be generally represented by the structure of Formula (22):

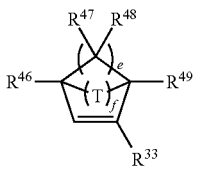

Formula (22)

wherein e is an integer in the range of 1 to 8, typically 2 to 4, f is generally 1 or 2, T is lower alkylene or lower alkenylene, generally substituted or unsubstituted methyl or ethyl, $R^{33}$ is as defined above, and $R^{46}$, $R^{47}$, $R^{48}$, and $R^{49}$ are as defined for $R^{34}$ through $R^{39}$ Preferred olefinic reactants within this group are in the norbornene family, having the Formula (23)

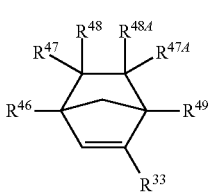

Formula (23)

wherein, $R^{33}$, and $R^{46}$ through $R^{49}$ are as defined previously, and $R^{47A}$ and $R^{48A}$ are defined as for $R^{47}$ and $R^{48}$.

Examples of bicyclic and polycyclic olefinic reactants thus include, without limitation, dicyclopentadiene, tricyclopentadiene, dicyclohexadiene, norbornene, 5-methyl-2-norbornene, 5-ethyl-2-norbornene, 5-isobutyl-2-norbornene, 5,6-dimethyl-2-norbornene, 5-phenylnorbornene, 5-benzylnorbornene, 5-acetylnorbornene, 5-methoxycarbonylnorbornene, 5-ethoxycarbonyl norbornene, 5-methyl-5-methoxy-carbonylnorbornene, 5-cyanonorbornene, 5,5,6-trimethyl-2-norbornene, cyclo-hexenylnorbornene, endo, exo-5,6-dimethoxynorbornene, endo, endo-5,6-dimethoxynorbornene, endo, exo-5,6-dimethoxycarbonyl-norbornene, endo, endo-5,6-dimethoxy carbonylnorbornene, 2,3-dimethoxynorbornene, norbornadiene, tricycloundecene, tetra cyclododecene, 8-methyltetracyclododecene, 8-ethyl-tetracyclododecene, 8-methoxy carbonyl tetracyclododecene, 8-methyl-8-tetracyclo-dodecene, 8-cyanotetracyclododecene, pentacyclo pentadecene, pentacyclohexadecene, 1,9-octadecadiene, and the like.

In general, the second α-olefin reactant may be represented by the structure of Formula (24):

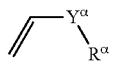

Formula (24)

wherein, $Y^\alpha$ is selected from the group comprising nil, $CH_2$, O, or S; and $R^\alpha$ is selected from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge).

Methods of the Invention

In one embodiment, the invention provides a method for performing a cross metathesis reaction, comprising: contacting a first olefin reactant with a second olefin reactant in the presence of a C—H activated catalyst under conditions effective to allow a cross metathesis reaction to occur.

In another embodiment, the invention provides a method for performing a cross metathesis reaction, comprising: contacting a first olefin reactant with a second olefin reactant in the presence of a C—H activated catalyst under conditions effective to allow a cross metathesis reaction to occur, wherein the first olefin reactant and the second olefin reactant may be the same or different.

In another embodiment, the invention provides a method for performing a cross metathesis reaction, comprising: contacting a first olefin reactant with a second olefin reactant in the presence of an enantioenriched C—H activated catalyst under conditions effective to allow a cross metathesis reaction to occur, wherein the first olefin reactant and the second olefin reactant may be the same or different.

In another embodiment, the invention provides a method for performing a cross metathesis reaction, comprising: contacting a first olefin reactant with a second olefin reactant in the presence of an enantiopure C—H activated catalyst under conditions effective to allow a cross metathesis reaction to occur, wherein the first olefin reactant and the second olefin reactant may be the same or different.

In another embodiment, the invention provides a method for performing an asymmetric cross metathesis reaction, comprising: contacting a first olefin reactant with a second olefin reactant in the presence of a C—H activated catalyst under conditions effective to allow a cross metathesis reaction to occur, wherein the first olefin reactant and the second olefin reactant may be the same or different.

In another embodiment, the invention provides a method for performing an asymmetric cross metathesis reaction, comprising: contacting a first olefin reactant with a second olefin reactant in the presence of an enantioenriched C—H activated catalyst under conditions effective to allow a cross metathesis reaction to occur, wherein the first olefin reactant and the second olefin reactant may be the same or different.

In another embodiment, the invention provides a method for performing an asymmetric cross metathesis reaction, comprising: contacting a first olefin reactant with a second olefin reactant in the presence of an enantiopure C—H activated catalyst under conditions effective to allow a cross metathesis reaction to occur, wherein the first olefin reactant and the second olefin reactant may be the same or different.

In another embodiment, the invention provides a method for performing an asymmetric cross metathesis reaction, comprising: contacting a first olefin reactant comprising two terminal olefins (i.e., a diene) and a second olefin reactant, wherein the second olefin reactant comprises either a di-substituted (internal) olefin or a terminal olefin, wherein the first olefin reactant and the second olefin reactant are brought into contact in the presence of a catalytically effective amount of an enantioenriched C—H activated complex, under conditions and for a time period effective to allow the asymmetric cross metathesis reaction to occur.

In another embodiment, the invention provides a method for performing an asymmetric cross metathesis reaction, comprising: contacting a first olefin reactant comprising two terminal olefins, which is a 1,4-diene and a second olefin reactant, wherein the second olefin reactant comprises a di-substituted (internal) olefin, wherein the first olefin reactant and the second olefin reactant are brought into contact in the presence of a catalytically effective amount of an enantioenriched C—H activated catalyst, under conditions and for a time period effective to allow the asymmetric cross metathesis reaction to occur.

In another embodiment, the invention provides a method for performing an asymmetric cross metathesis reaction, comprising: contacting a first olefin reactant comprising two terminal olefins, which is a 1,5-diene and a second olefin reactant, wherein the second olefin reactant comprises a di-substituted (internal) olefin, wherein the first olefin reactant and the second olefin reactant are brought into contact in the presence of a catalytically effective amount of an enantioenriched C—H activated catalyst, under conditions and for a time period effective to allow the asymmetric cross metathesis reaction to occur.

In another embodiment, the invention provides a method for performing an asymmetric cross metathesis reaction, comprising: contacting a first olefin reactant comprising two terminal olefins, which is a 1,6-diene and a second olefin reactant, wherein the second olefin reactant comprises a di-substituted (internal) olefin, wherein the first olefin reactant and the second olefin reactant are brought into contact in the presence of a catalytically effective amount of an enantioenriched C—H activated catalyst, under conditions and for a time period effective to allow the asymmetric cross metathesis reaction to occur.

In another embodiment, the invention provides a method for performing an asymmetric cross metathesis reaction, comprising: contacting a first olefin reactant comprising two terminal olefins, which is a 1,4-diene and a second olefin reactant, wherein the second olefin reactant comprises a terminal olefin, wherein the first olefin reactant and the second olefin reactant are brought into contact in the presence of a catalytically effective amount of an enantioenriched C—H activated catalyst, under conditions and for a time period effective to allow the asymmetric cross metathesis reaction to occur.

In another embodiment, the invention provides a method for performing an asymmetric cross metathesis reaction, comprising: contacting a first olefin reactant comprising two terminal olefins, which is a 1,5-diene and a second olefin reactant, wherein the second olefin reactant comprises a terminal olefin, wherein the first olefin reactant and the second olefin reactant are brought into contact in the presence of a catalytically effective amount of an enantioenriched C—H activated catalyst, under conditions and for a time period effective to allow the asymmetric cross metathesis reaction to occur.

In another embodiment, the invention provides a method for performing an asymmetric cross metathesis reaction, comprising: contacting a first olefin reactant comprising two terminal olefins, which is a 1,6-diene and a second olefin reactant, wherein the second olefin reactant comprises a terminal olefin, wherein the first olefin reactant and the second olefin reactant are brought into contact in the presence of a catalytically effective amount of an enantioenriched C—H activated catalyst, under conditions and for a time period effective to allow the asymmetric cross metathesis reaction to occur.

In another embodiment, the invention provides a method for performing an asymmetric ring closing metathesis reaction, comprising: contacting a olefin reactant comprising three terminal olefins (i.e., a triene), wherein the olefin reactant is brought into contact in the presence of a catalytically effective amount of the complex, under conditions and for a time period effective to allow the ring closing metathesis reaction to occur.

In another embodiment, the invention provides a method for performing an asymmetric ring closing metathesis reaction, comprising: contacting a olefin reactant comprising three terminal olefins (i.e., a triene), wherein the olefin reactant is brought into contact in the presence of a catalytically effective amount of the enantioenriched C—H activated catalyst, under conditions and for a time period effective to allow the asymmetric ring closing metathesis reaction to occur.

In another embodiment, the invention provides a method for performing an asymmetric ring closing metathesis reaction, comprising: contacting an olefin reactant comprising three terminal olefins with an enantioenriched C—H activated catalyst under conditions effective to allow the asymmetric ring closing metathesis reaction to occur to form at least one ring closing metathesis product.

In another embodiment, the invention provides a method for performing an asymmetric ring closing metathesis reaction, comprising: contacting an olefin reactant comprising three terminal olefins with an enantioenriched C—H activated catalyst under conditions effective to allow the asymmetric ring closing metathesis reaction to occur to form at least one ring closing metathesis product, the at least one ring closing metathesis product having an enantiomeric excess of greater than 50%.

In another embodiment, the invention provides a method for performing an asymmetric ring closing metathesis reaction, comprising: contacting an olefin reactant comprising three terminal olefins with an enantiopure C—H activated catalyst under conditions effective to allow the asymmetric ring closing metathesis reaction to occur to form at least one ring closing metathesis product.

In another embodiment, the invention provides a method for performing an asymmetric ring closing metathesis reaction, comprising: contacting an olefin reactant comprising three terminal olefins with an enantiopure C—H activated catalyst under conditions effective to allow the asymmetric ring closing metathesis reaction to occur to form at least one ring closing metathesis product, the at least one ring closing metathesis product having an enantiomeric excess of greater than 50%.

In another embodiment, the invention provides a method for performing an asymmetric ring closing metathesis reaction, comprising: contacting an olefin reactant comprising three terminal olefins with a C—H activated catalyst under conditions effective to allow the asymmetric ring closing metathesis reaction to occur to form at least one ring closing metathesis product.

In another embodiment, the invention provides a method for performing an asymmetric ring closing metathesis reaction, comprising: contacting an olefin reactant comprising three terminal olefins with a C—H activated catalyst under conditions effective to allow the asymmetric ring closing metathesis reaction to occur to form at least one ring closing metathesis product, the at least one ring closing metathesis product having an enantiomeric excess of greater than 50%.

In another embodiment, the invention provides a method for performing a ring closing metathesis reaction, comprising: contacting an olefin reactant comprising three terminal olefins with an enantioenriched C—H activated catalyst under conditions effective to allow the ring closing metathesis reaction to occur to form at least one ring closing metathesis product.

In another embodiment, the invention provides a method for performing a ring closing metathesis reaction, comprising: contacting an olefin reactant comprising three terminal olefins with an enantioenriched C—H activated catalyst under conditions effective to allow the ring closing metathesis reaction to occur to form at least one ring closing metathesis product, the at least one ring closing metathesis product having an enantiomeric excess of greater than 50%.

In another embodiment, the invention provides a method for performing a ring closing metathesis reaction, comprising: contacting an olefin reactant comprising three terminal olefins with an enantiopure C—H activated catalyst under conditions effective to allow the ring closing metathesis reaction to occur to form at least one ring closing metathesis product.

In another embodiment, the invention provides a method for performing a ring closing metathesis reaction, comprising: contacting an olefin reactant comprising three terminal olefins with an enantiopure C—H activated catalyst under conditions effective to allow the ring closing metathesis reaction to occur to form at least one ring closing metathesis product, the at least one ring closing metathesis product having an enantiomeric excess of greater than 50%.

In another embodiment, the invention provides a method for performing a ring closing metathesis reaction, comprising: contacting an olefin reactant comprising three terminal olefins with a C—H activated catalyst under conditions effective to allow the ring closing metathesis reaction to occur to form at least one ring closing metathesis product.

In another embodiment, the invention provides a method for performing a ring closing metathesis reaction, comprising: contacting an olefin reactant comprising three terminal olefins with a C—H activated catalyst under conditions effective to allow the ring closing metathesis reaction to occur to form at least one ring closing metathesis product, the at least one ring closing metathesis product having an enantiomeric excess of greater than 50%.

In another embodiment, the invention provides a method for performing an enantio-selective ring closing metathesis reaction, comprising: contacting an olefin reactant comprising three terminal olefins with an enantioenriched C—H activated catalyst under conditions effective to allow the enantio-selective ring closing metathesis reaction to occur to form at least one ring closing metathesis product.

In another embodiment, the invention provides a method for performing an enantio-selective ring closing metathesis reaction, comprising: contacting an olefin reactant comprising three terminal olefins with an enantioenriched C—H activated catalyst under conditions effective to allow the enantio-selective ring closing metathesis reaction to occur to form at least one ring closing metathesis product, the at least one ring closing metathesis product having an enantiomeric excess of greater than 50%.

In another embodiment, the invention provides a method for performing an enantio-selective ring closing metathesis reaction, comprising: contacting an olefin reactant comprising three terminal olefins with an enantiopure C—H activated catalyst under conditions effective to allow the enantio-selective ring closing metathesis reaction to occur to form at least one ring closing metathesis product.

In another embodiment, the invention provides a method for performing an enantio-selective ring closing metathesis reaction, comprising: contacting an olefin reactant comprising three terminal olefins with an enantiopure C—H activated catalyst under conditions effective to allow the enantio-selective ring closing metathesis reaction to occur to form at least one ring closing metathesis product, the at least one ring closing metathesis product having an enantiomeric excess of greater than 50%.

In another embodiment, the invention provides a method for performing an enantio-selective ring closing metathesis reaction, comprising: contacting an olefin reactant comprising three terminal olefins with a C—H activated catalyst under conditions effective to allow the enantio-selective ring closing metathesis reaction to occur to form at least one ring closing metathesis product.

In another embodiment, the invention provides a method for performing an enantio-selective ring closing metathesis reaction, comprising: contacting an olefin reactant comprising three terminal olefins with a C—H activated catalyst under conditions effective to allow the enantio-selective ring closing metathesis reaction to occur to form at least one ring closing metathesis product, the at least one ring closing metathesis product having an enantiomeric excess of greater than 50%.

In a further embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form a cross-metathesis mixture, wherein the cross-metathesis mixture comprises at least one cross-metathesis product, wherein the at least one cross-metathesis product comprises a product internal olefin, wherein the product internal olefin is in a Z-configuration.

Still, in one embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form a cross-metathesis mixture, wherein the cross-metathesis mixture comprises at least one cross-metathesis product, wherein the at least one cross-metathesis product comprises a product internal olefin, wherein the product internal olefin is in a Z-configuration, wherein the first olefin reactant and the second olefin reactant may be the same or different.

Still, in another embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form at least one cross-metathesis product, wherein the at least one cross-metathesis product comprises a product internal olefin, wherein the product internal olefin is in a Z-configuration.

Still, in a further embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form at least one cross-metathesis product, wherein the at least one cross-metathesis product comprises a product internal olefin, wherein the product internal olefin is in a Z-configuration, wherein the first olefin reactant and the second olefin reactant may be the same or different.

Still, in another embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form at least one cross-metathesis product having a Z:E ratio greater than 1:1.

Still, in another embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form at least one cross-metathesis product having a Z:E ratio greater than 1:1, wherein the first olefin reactant and the second olefin reactant may be the same or different.

Further, in one embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form at least one cross-metathesis product having a Z:E ratio greater than 1:1 in favor or the Z-isomer.

Further, in one embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form at least one cross-metathesis product having a Z:E ratio greater than 1:1 in favor or the Z-isomer, the at least one cross-metathesis product having an enantiomeric excess of greater than 50%.

Further, in one embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form at least one cross-metathesis product having a Z:E ratio greater than 1:1 in favor or the Z-isomer and an enantiomeric excess of greater than 50%.

Further, in one embodiment, the invention provides a method for performing a cross-metathesis reaction, comprising: contacting a first olefin reactant and a second olefin reactant in the presence of an enantioenriched C—H activated catalyst under conditions effective to allow the cross-metathesis reaction to occur to form at least one cross-metathesis product having a Z:E ratio greater than 1:1 in favor or the Z-isomer.

Further, in one embodiment, the invention provides a method for performing a cross-metathesis reaction, comprising: contacting a first olefin reactant and a second olefin reactant in the presence of an enantioenriched C—H activated catalyst under conditions effective to allow the cross-metathesis reaction to occur to form at least one cross-metathesis product having a Z:E ratio greater than 1:1 in favor or the Z-isomer, the at least one cross-metathesis product having an enantiomeric excess of greater than 50%.

Further, in one embodiment, the invention provides a method for performing a cross-metathesis reaction, comprising: contacting a first olefin reactant and a second olefin reactant in the presence of an enantioenriched C—H activated catalyst under conditions effective to allow the cross-metathesis reaction to occur to form at least one cross-metathesis product having a Z:E ratio greater than 1:1 in favor or the Z-isomer and an enantiomeric excess of greater than 50%.

Further, in one embodiment, the invention provides a method for performing a cross-metathesis reaction, comprising: contacting a first olefin reactant and a second olefin reactant in the presence of an enantiopure C—H activated catalyst under conditions effective to allow the cross-metathesis reaction to occur to form at least one cross-metathesis product having a Z:E ratio greater than 1:1 in favor or the Z-isomer.

Further, in one embodiment, the invention provides a method for performing a cross-metathesis reaction, comprising: contacting a first olefin reactant and a second olefin reactant in the presence of an enantiopure C—H activated catalyst under conditions effective to allow the cross-metathesis reaction to occur to form at least one cross-metathesis product having a Z:E ratio greater than 1:1 in favor or the Z-isomer, the at least one cross-metathesis product having an enantiomeric excess of greater than 50%.

Further, in one embodiment, the invention provides a method for performing a cross-metathesis reaction, comprising: contacting a first olefin reactant and a second olefin reactant in the presence of an enantiopure C—H activated catalyst under conditions effective to allow the cross-metathesis reaction to occur to form at least one cross-metathesis product having a Z:E ratio greater than 1:1 in favor or the Z-isomer and an enantiomeric excess of greater than 50%.

Further, in one embodiment, the invention provides a method for performing an asymmetric cross-metathesis reaction, comprising: contacting a first olefin reactant and a second olefin reactant in the presence of a C—H activated catalyst under conditions effective to allow the asymmetric cross-metathesis reaction to occur to form at least one cross-metathesis product having a Z:E ratio greater than 1:1 in favor or the Z-isomer, the at least one cross-metathesis product having an enantiomeric excess of greater than 50%.

Further, in one embodiment, the invention provides a method for performing an asymmetric cross-metathesis reaction, comprising: contacting a first olefin reactant and a second olefin reactant in the presence of a C—H activated catalyst under conditions effective to allow the asymmetric cross-metathesis reaction to occur to form at least one cross-metathesis product having a Z:E ratio greater than 1:1 in favor or the Z-isomer and an enantiomeric excess of greater than 50%.

Further, in one embodiment, the invention provides a method for performing an asymmetric cross-metathesis reaction, comprising: contacting a first olefin reactant and a second olefin reactant in the presence of an enantioenriched C—H activated catalyst under conditions effective to allow the asymmetric cross-metathesis reaction to occur to form at least one cross-metathesis product having a Z:E ratio greater than 1:1 in favor or the Z-isomer.

Further, in one embodiment, the invention provides a method for performing an asymmetric cross-metathesis reaction, comprising: contacting a first olefin reactant and a second olefin reactant in the presence of an enantioenriched C—H activated catalyst under conditions effective to allow the asymmetric cross-metathesis reaction to occur to form at least one cross-metathesis product having a Z:E ratio greater than 1:1 in favor or the Z-isomer, the at least one cross-metathesis product having an enantiomeric excess of greater than 50%.

Further, in one embodiment, the invention provides a method for performing an asymmetric cross-metathesis reaction, comprising: contacting a first olefin reactant and a second olefin reactant in the presence of an enantioenriched C—H activated catalyst under conditions effective to allow the asymmetric cross-metathesis reaction to occur to form at least one cross-metathesis product having a Z:E ratio greater than 1:1 in favor or the Z-isomer and an enantiomeric excess of greater than 50%.

Further, in one embodiment, the invention provides a method for performing an asymmetric cross-metathesis reaction, comprising: contacting a first olefin reactant and a second olefin reactant in the presence of an enantiopure C—H activated catalyst under conditions effective to allow the asymmetric cross-metathesis reaction to occur to form at least one cross-metathesis product having a Z:E ratio greater than 1:1 in favor or the Z-isomer.

Further, in one embodiment, the invention provides a method for performing an asymmetric cross-metathesis reaction, comprising: contacting a first olefin reactant and a second olefin reactant in the presence of an enantiopure C—H activated catalyst under conditions effective to allow the asymmetric cross-metathesis reaction to occur to form at least one cross-metathesis product having a Z:E ratio greater than 1:1 in favor or the Z-isomer, the at least one cross-metathesis product having an enantiomeric excess of greater than 50%.

Further, in one embodiment, the invention provides a method for performing an asymmetric cross-metathesis reaction, comprising: contacting a first olefin reactant and a second olefin reactant in the presence of an enantiopure C—H activated catalyst under conditions effective to allow the asymmetric cross-metathesis reaction to occur to form at least one cross-metathesis product having a Z:E ratio greater than 1:1 in favor or the Z-isomer and an enantiomeric excess of greater than 50%.

In another embodiment, the invention provides a method for performing an asymmetric cross-metathesis reaction, comprising: contacting a first olefin reactant and a second olefin reactant in the presence of a C—H activated catalyst under conditions effective to allow the asymmetric cross-metathesis reaction to occur to form at least cross-metathesis product, wherein the first olefin reactant is a prochiral diene.

In another embodiment, the invention provides a method for performing an asymmetric cross-metathesis reaction, comprising: contacting a first olefin reactant and a second olefin reactant in the presence of an enantioenriched C—H activated catalyst under conditions effective to allow the asymmetric cross-metathesis reaction to occur to form at least cross-metathesis product, wherein the first olefin reactant is a prochiral diene.

In another embodiment, the invention provides a method for performing an asymmetric cross-metathesis reaction, comprising: contacting a first olefin reactant and a second olefin reactant in the presence of an enantiopure C—H activated catalyst under conditions effective to allow the asymmetric cross-metathesis reaction to occur to form at least cross-metathesis product, wherein the first olefin reactant is a prochiral diene.

In another embodiment, the invention provides a method for performing an asymmetric cross-metathesis reaction, comprising: contacting a first olefin reactant and a second olefin reactant in the presence of a C—H activated catalyst under conditions effective to allow the asymmetric cross-metathesis reaction to occur to form at least cross-metathesis product, wherein the first olefin reactant is selected from a prochiral 1,4-, 1,5-, or 1,6-diene.

In another embodiment, the invention provides a method for performing an asymmetric cross-metathesis reaction, comprising: contacting a first olefin reactant and a second olefin reactant in the presence of a C—H activated catalyst under conditions effective to allow the asymmetric cross-metathesis reaction to occur to form at least one desymmetrized metathesis product, wherein the first olefin reactant is selected from a prochiral 1,4-, 1,5-, or 1,6-diene.

A method for performing an asymmetric ring closing metathesis reaction, comprising: contacting a prochiral triene with a C—H activated catalyst under conditions effective to allow the asymmetric ring closing metathesis reaction to occur to form at least one ring closing metathesis product.

A method for performing an asymmetric ring closing metathesis reaction, comprising: contacting a prochiral triene with an enantioenriched C—H activated catalyst under conditions effective to allow the asymmetric ring closing metathesis reaction to occur to form at least one ring closing metathesis product.

A method for performing an asymmetric ring closing metathesis reaction, comprising: contacting a prochiral triene with an enantiopure C—H activated catalyst under conditions effective to allow the asymmetric ring closing metathesis reaction to occur to form at least one ring closing metathesis product.

Further, in another embodiment, the invention provides a method for performing a cross-metathesis reaction, comprising: contacting a first olefin reactant and a second olefin reactant in the presence of a C—H activated catalyst under conditions effective to allow the cross-metathesis reaction to occur to form at least one cross-metathesis product having a Z:E ratio greater than 1:1 in favor or the Z-isomer, wherein the first olefin reactant and the second olefin reactant may be the same or different.

In another embodiment, the invention provides a method for preparing at least one cross-metathesis product, comprising: contacting a first olefin reactant and a second olefin reactant in the presence of a C—H activated catalyst under conditions effective to allow a cross-metathesis reaction to occur to form the at least one cross-metathesis product, the at least one cross-metathesis product having a Z:E ratio greater than 1:1.

In another embodiment, the invention provides a method for preparing at least one cross-metathesis product, comprising: contacting a first olefin reactant and a second olefin reactant in the presence of a C—H activated catalyst under conditions effective to allow a cross-metathesis reaction to occur to form the at least one cross-metathesis product, the at least one cross-metathesis product having a Z:E ratio greater than 1:1, wherein the first olefin reactant and the second olefin reactant may be the same or different.

In a further embodiment, the invention provides a method for preparing at least one cross-metathesis product, comprising: contacting a first olefin reactant and a second olefin reactant in the presence of a C—H activated catalyst under conditions effective to allow a cross-metathesis reaction to occur to form the at least one cross-metathesis product, the at least one cross-metathesis product having a Z:E ratio greater than 1:1 in favor of the Z-isomer.

In a further embodiment, the invention provides a method for preparing at least one cross-metathesis product, comprising: contacting a first olefin reactant and a second olefin reactant in the presence of a C—H activated catalyst under conditions effective to allow a cross-metathesis reaction to occur to form the at least one cross-metathesis product, the at least one cross-metathesis product having a Z:E ratio greater than 1:1 in favor of the Z-isomer, the at least one cross-metathesis product having an enantiomeric excess of greater than 50%.

In a further embodiment, the invention provides a method for preparing at least one cross-metathesis product, comprising: contacting a first olefin reactant and a second olefin reactant in the presence of a C—H activated catalyst under conditions effective to allow a cross-metathesis reaction to occur to form the at least one cross-metathesis product, the at least one cross-metathesis product having a Z:E ratio greater than 1:1 in favor of the Z-isomer and an enantiomeric excess of greater than 50%.

In a further embodiment, the invention provides a method for preparing at least one cross-metathesis product, comprising: contacting a first olefin reactant and a second olefin reactant in the presence of an enantioenriched C—H activated catalyst under conditions effective to allow a cross-metathesis reaction to occur to form the at least one cross-metathesis product, the at least one cross-metathesis product having a Z:E ratio greater than 1:1 in favor of the Z-isomer.

In a further embodiment, the invention provides a method for preparing at least one cross-metathesis product, comprising: contacting a first olefin reactant and a second olefin reactant in the presence of an enantioenriched C—H activated catalyst under conditions effective to allow a cross-metathesis reaction to occur to form the at least one cross-metathesis product, the at least one cross-metathesis product having a Z:E ratio greater than 1:1 in favor of the Z-isomer, the at least one cross-metathesis product having an enantiomeric excess of greater than 50%.

In a further embodiment, the invention provides a method for preparing at least one cross-metathesis product, comprising: contacting a first olefin reactant and a second olefin reactant in the presence of an enantioenriched C—H activated catalyst under conditions effective to allow a cross-metathesis reaction to occur to form the at least one cross-metathesis product, the at least one cross-metathesis product having a Z:E ratio greater than 1:1 in favor of the Z-isomer and an enantiomeric excess of greater than 50%.

In a further embodiment, the invention provides a method for preparing at least one cross-metathesis product, comprising: contacting a first olefin reactant and a second olefin reactant in the presence of an enantiopure C—H activated catalyst under conditions effective to allow a cross-metathesis reaction to occur to form the at least one cross-metathesis product, the at least one cross-metathesis product having a Z:E ratio greater than 1:1 in favor of the Z-isomer.

In a further embodiment, the invention provides a method for preparing at least one cross-metathesis product, comprising: contacting a first olefin reactant and a second olefin reactant in the presence of an enantiopure C—H activated catalyst under conditions effective to allow a cross-metathesis reaction to occur to form the at least one cross-metathesis product, the at least one cross-metathesis product having a Z:E ratio greater than 1:1 in favor of the Z-isomer, the at least one cross-metathesis product having an enantiomeric excess of greater than 50%.

In a further embodiment, the invention provides a method for preparing at least one cross-metathesis product, comprising: contacting a first olefin reactant and a second olefin reactant in the presence of an enantiopure C—H activated catalyst under conditions effective to allow a cross-metathesis reaction to occur to form the at least one cross-metathesis product, the at least one cross-metathesis product having a Z:E ratio greater than 1:1 in favor of the Z-isomer and an enantiomeric excess of greater than 50%.

In a further embodiment, the invention provides a method for preparing at least one cross-metathesis product, comprising: contacting a first olefin reactant and a second olefin reactant in the presence of a C—H activated catalyst under conditions effective to allow a cross-metathesis reaction to occur to form the at least one cross-metathesis product, the at least one cross-metathesis product having a Z:E ratio greater than 1:1 in favor of the Z-isomer, wherein the first olefin reactant and the second olefin reactant may be the same or different.

In a further embodiment, the invention provides a method for performing Z-selective cross metathesis reaction, comprising: contacting a first olefin reactant with a second olefin reactant in the presence of a C—H activated catalyst, under conditions effective to allow the Z-selective cross metathesis reaction to occur to form at least one cross metathesis product.

In a further embodiment, the invention provides a method for performing Z-selective cross metathesis reaction, comprising: contacting a first olefin reactant with a second olefin reactant in the presence of an enantioenriched C—H activated catalyst, under conditions effective to allow the Z-selective cross metathesis reaction to occur to form at least one cross metathesis product.

In a further embodiment, the invention provides a method for performing Z-selective cross metathesis reaction, comprising: contacting a first olefin reactant with a second olefin reactant in the presence of an enantiopure C—H activated catalyst, under conditions effective to allow the Z-selective cross metathesis reaction to occur to form at least one cross metathesis product.

In a further embodiment, the invention provides a method for performing an enantio-selective cross metathesis reaction, comprising: contacting a first olefin reactant with a second olefin reactant in the presence of a C—H activated catalyst, under conditions effective to allow the an enantio-selective cross metathesis reaction to occur to form at least one cross metathesis product.

In a further embodiment, the invention provides a method for performing an enantio-selective cross metathesis reaction, comprising: contacting a first olefin reactant with a second olefin reactant in the presence of an enantioenriched C—H activated catalyst, under conditions effective to allow the an enantio-selective cross metathesis reaction to occur to form at least one cross metathesis product.

In a further embodiment, the invention provides a method for performing an enantio-selective cross metathesis reaction, comprising: contacting a first olefin reactant with a second olefin reactant in the presence of an enantiopure C—H activated catalyst, under conditions effective to allow the an enantio-selective cross metathesis reaction to occur to form at least one cross metathesis product.

In a further embodiment, the invention provides a method for performing an metathesis reaction, comprising: contacting a first olefin reactant with a second olefin reactant in the presence of an enantioenriched C—H activated catalyst, under conditions effective to allow the enantio-Z-selective cross metathesis reaction to occur to form at least one cross metathesis product.

In a further embodiment, the invention provides a method for performing an enantio-Z-selective cross metathesis reaction, comprising: contacting a first olefin reactant with a second olefin reactant in the presence of an enantiopure C—H activated catalyst, under conditions effective to allow the enantio-Z-selective cross metathesis reaction to occur to form at least one cross metathesis product.

In a further embodiment, the invention provides a method for performing an enantio-Z-selective cross metathesis reaction, comprising: contacting a first olefin reactant with a second olefin reactant in the presence of a C—H activated catalyst, under conditions effective to allow the enantio-Z-selective cross metathesis reaction to occur to form at least one cross metathesis product.

In a further embodiment, the invention provides a method for performing an enantio-Z-selective cross metathesis reaction, comprising: contacting a first olefin reactant with a second olefin reactant in the presence of an enantioenriched C—H activated catalyst, under conditions effective to allow the enantio-Z-selective cross metathesis reaction to occur to form at least one cross metathesis product, the at least one cross-metathesis product having a Z:E ratio greater than 1:1 in favor of the Z-isomer and an enantiomeric excess of greater than 50%.

In a further embodiment, the invention provides a method for performing an enantio-Z-selective cross metathesis reaction, comprising: contacting a first olefin reactant with a second olefin reactant in the presence of an enantiopure C—H activated catalyst, under conditions effective to allow the enantio-Z-selective cross metathesis reaction to occur to form at least one cross metathesis product, the at least one cross-metathesis product having a Z:E ratio greater than 1:1 in favor of the Z-isomer and an enantiomeric excess of greater than 50%.

In a further embodiment, the invention provides a method for performing an enantio-Z-selective cross metathesis reaction, comprising: contacting a first olefin reactant with a second olefin reactant in the presence of a C—H activated catalyst, under conditions effective to allow the enantio-Z-selective cross metathesis reaction to occur to form at least one cross metathesis product, the at least one cross-metathesis product having a Z:E ratio greater than 1:1 in favor of the Z-isomer and an enantiomeric excess of greater than 50%.

In a further embodiment, the invention provides a method for performing an olefin metathesis reaction, comprising: contacting at least one olefin with at least one C—H activated catalyst complex under conditions effective to allow the olefin metathesis reaction to occur.

In a further embodiment, the invention provides a method for performing an olefin metathesis reaction, comprising: contacting at least one olefin with at least one enantioenriched C—H activated catalyst complex under conditions effective to allow the olefin metathesis reaction to occur.

In a further embodiment, the invention provides a method for performing an olefin metathesis reaction, comprising: contacting at least one olefin with at least one enantiopure C—H activated catalyst complex under conditions effective to allow the olefin metathesis reaction to Occur.

Catalyzed Asymmetric Ring Opening of Olefins

AROCM of strained olefins is a powerful method for the construction of enantioenriched cyclic and acyclic dienes containing up to 5 stereocenters. The products contain two differentially substituted alkenes, which are poised for subsequent chemoselective transformations (see Hoveyda, A. H. *J. Org. Chem.* 2014, 79, 4763-4792).

Without being limited by any hypothesis, it is likely that the chelating NHC ligand of 5 and 6, which contains stereogenic carbon and Ru atoms, would control the approach of the strained olefin reactant to the reactive metal center leading to a highly stereoselective AROCM reaction. The bulky adamantyl group limits approach of the reactant olefin solely toward the opposite face of the alkylidene. Strong preference for side-bound metallacyclic intermediates would result in higher fidelity communication of the stereochemical information stored in the NHC ligand. Finally, the pocket capped by the N-aryl substituent of the NHC is well suited for the Z-selective ring opening as it favors the formation of all-cis metallacyclobutanes, which had been previously observed in the context of ring opening metathesis polymerization (ROMP) (see Keitz, B. K.; Fedorov, A.; Grubbs, R. H. *J. Am. Chem. Soc.* 2012, 134, 2040-2043, Rosebrugh, L. E.; Marx, V. M.; Keitz, B. K.; Grubbs, R. H. *J. Am. Chem. Soc.* 2013, 135, 10032-10035).

In accord with this hypothesis, enantioenriched cyclometalated complex 5 catalyzed the AROCM of norbornenes (see Hartung, J.; Grubbs, R. H. *J. Am. Chem. Soc.* 2013, 135, 10183-10185) and cyclobutenes, (see Hartung, J.; Grubbs, R. H. *Angew. Chem. Int. Ed.* 2014, 53, 3885-3888) resulting in the first ruthenium-catalyzed Z-selective and enantioselective ring opening of these strained rings with simple terminal olefins (Table 1). 2,3-Di-endo substituted norbornenes afforded products in high Z-selectivity, with 2,3-dibenzyloxy substitution resulting in high enantioselectivity (93%, Table 1, entry 1). Substrates bearing 7-anti and 7-syn substitution (9c and 9d) were well tolerated, affording products in high ee (entries 3 and 4). However, the lack of 2, 3 disubstitution appeared to have a strong influence on the diastereoselectivity of the reaction, with the strongest influence observed for 7-syn substitution resulting in a preference for the E product (see Hamilton, J. G.; Ivin, K. J.; Rooney, J. J. *J. Mol. Catal.* 1986, 36, 115-125). Benzonorbornadiene 9e, possessing $sp^2$ carbons at the 2 and 3 positions, also resulted in reduced Z-selectivity, although the products were formed in excellent enantiomeric excess. Regardless of the E/Z selectivity, it was observed that in cases where both geometrical isomers could be isolated, the E and Z isomers were formed with identical enantioenrichment (entries 3-5).

TABLE 1

Selected examples of Z-selective AROCM catalyzed by 5.

| Entry | 9a-h | R² (10a-d) | Product | Yield (%) | Z/E ratio | ee Z (%) (ee E) (%)ᵃ |
|---|---|---|---|---|---|---|
| 1ᵇ | 9a | OAc | 11a | 64 | 95:5 | 93 (−) |
| 2ᵇ | 9b | OAc | 11b | 58 | 98:2 | 75 (−) |
| 3ᵇ | 9c | OAc | 11c | 40 | 7:3 | 95 (95) |
| 4 | 9d | OAc | 11d | 56 | 15:85 | >98 (>98) |
| 5 | 9e | OAc | 11e | 55ᶜ | 76:24 | 94 (93) |

TABLE 1-continued

Selected examples of Z-selective AROCM catalyzed by 5.

[Reaction scheme: 9a-h + 10a-d (R² group) → 11a-i, using catalyst 5 (1 mol %), 23° C., 1-1.5 h, THF. Catalyst 5 is a ruthenium complex bearing an adamantyl/mesityl-substituted imidazolinylidene ligand, a nitrato ligand, and an iPr-phenoxy benzylidene.]

| Entry | 9a-h | R² (10a-d) | Product | Yield (%) | Z/E ratio | ee Z (%) (ee E) (%)[a] |
|---|---|---|---|---|---|---|
| 6[d] | 9f (cyclobutene with OH, OH) | OBz | 11f | 67 | 75:25 | 91 (67) |
| 7[d] | 9g (cyclobutene with OBz, OBz) | OH | 11g | 69 | 75:25 | 96 (82) |
| 8[d] | 9h (cyclobutene with OBn, OBn) | OAc | 11h | 79 | 85:15 | 95 (–) |
| 9[d] | 9h (cyclobutene with OBn, OBn) | CH₂C(O)CH₃ | 11i | 65 | 90:10 | 92 (84) |

[a]Determined by chiral SFC on chromatographically purified products.
[b]From reference Hartung, J.; Grubbs, R. H. *J. Am. Chem. Soc.* 2013, 135, 10183-10185.
[c]Determined by ¹H NMR spectroscopy.
[d]From reference Hartung, J.; Grubbs, R. H. *Angew. Chem. Int. Ed.* 2014, 53, 3885-3888.

In contrast to the reactions employing norbornenes, the AROCM of cyclobutenes occurred with higher yield and similar levels of Z-selectivity (see Hartung, J.; Grubbs, R. H. *Angew. Chem. Int. Ed.* 2014, 53, 3885-3888). AROCM of cyclobutenes tolerated commonly used oxygen protecting groups as well as free alcohols on both the cyclobutene (9f) and terminal olefin (10c) reactants. Notably, in stark contrast to the outcome for the norbornene AROCM, the ee of the Z- and E-products differed considerably. This difference was observed in all 7 cases where both isomers could be analyzed, and the ee's of Z- and E-products ranged from 91 and 67% ee, to 93 and 86% ee (for example, Table 1, entries 6-9).

In order to determine the stereochemical relationship between the double bond isomers, E-9e and Z-9e were hydrogenated to afford 12. Both reactions afforded the same major enantiomer of 12 as determined by chiral SFC (Scheme 4), demonstrating that the absolute configurations at the 1- and 3-positions of E-9e and Z-9e were identical. The equal magnitude and sense of enantioenrichment suggests a common intermediate in the AROCM of norbornenes from which the E and Z products are ultimately generated.

Scheme 4. Determination of Relative Stereoinduction in E and Z products

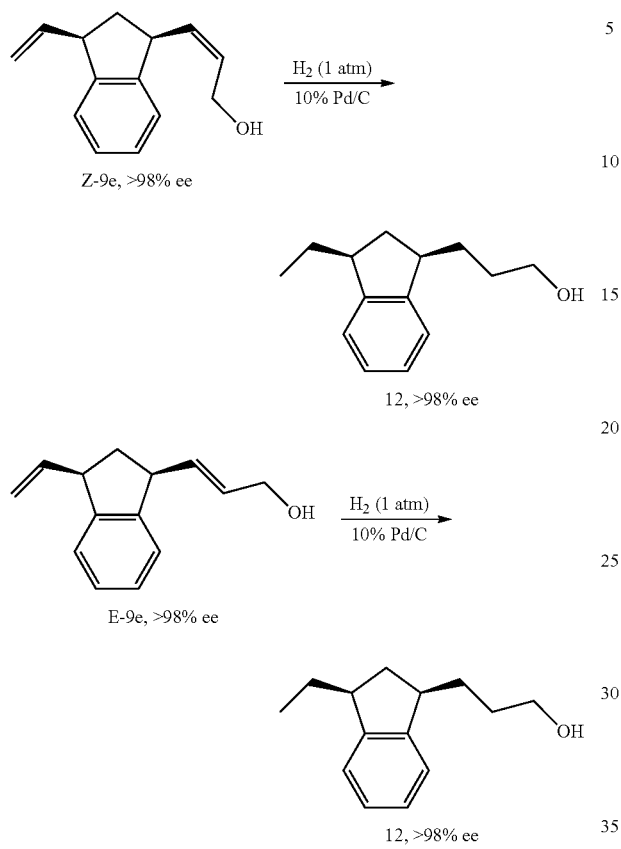

In contrast, the E and Z AROCM products, derived from cyclobutenes, are formed with different ee's, suggesting that the initial ring-opening step occurs through the alkylidene derived from the terminal olefin. In the proposed pathway for the AROCM of cyclobutenes with 5, the initial ring opening of the strained olefin with an alkylidene derived from the terminal olefin is diastereo- and enantiodetermining, resulting in the difference in enantioenrichment for the E and Z products.

Scheme 5. Proposed Change in Mechanism for AROCM of Norbornenes and Cyclobutenes

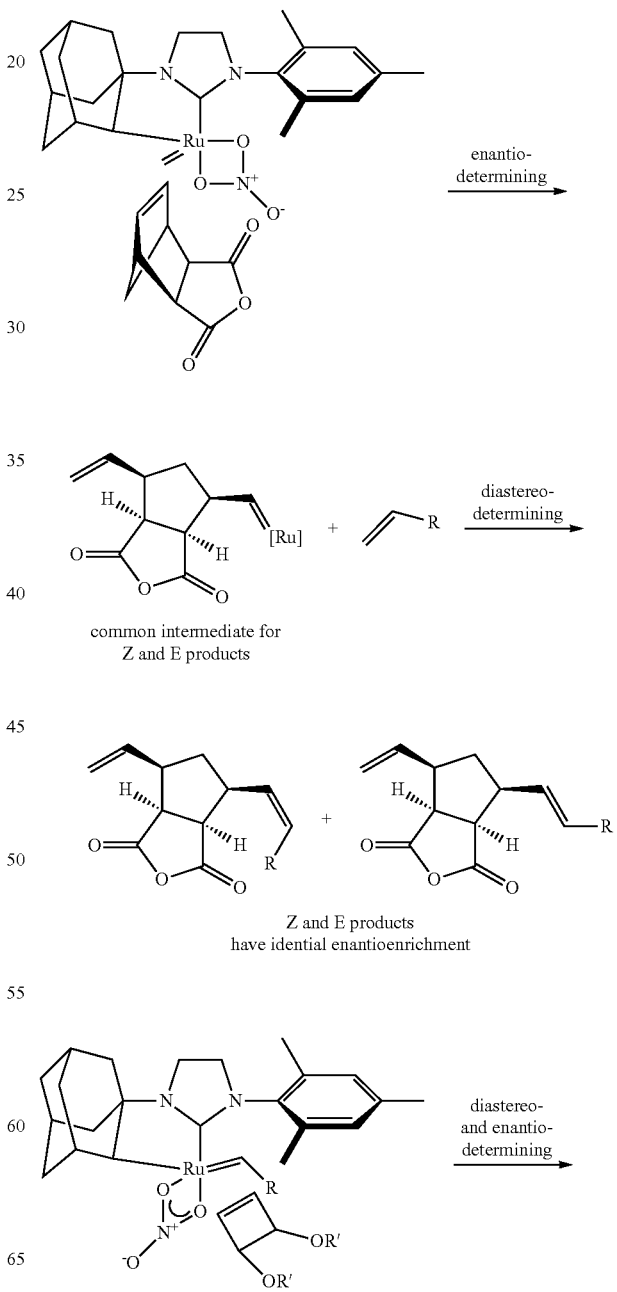

A possible explanation for the identical enantioenrichment of the Z and E-isomers is that a secondary metathesis process isomerizes some of the Z-product to the more thermodynamically favored E-product. However, this can be ruled out by the observation that the E/Z ratio of AROCM products was constant throughout the course of the reaction and for several hours after complete conversion. Likewise in the cyclobutene AROCM, resubmission of product Z-11f to the reaction conditions in the presence of enantiopure catalyst 5 resulted in recovery of the pure Z-product in identical enantioenrichment and Z/E ratio. These experiments strongly suggested that secondary metathesis proceeds at a negligible rate as compared to the productive AROCM reaction.

Our observations regarding AROCM of norbornenes and cyclobutenes suggest that the structure and strain energy of the cyclic olefin reactant dramatically alter the catalytic pathway responsible for the mono-cross products (Scheme 5). The identical enantioenrichment of the E and Z products formed in the AROCM of norbornenes suggests that a methylidene intermediate is involved in the enantiodetermining ring-opening step. The resultant alkylidene then reacts with an equivalent of terminal olefin to afford the monocross products. Since the enantiodetermining step precedes the olefin geometry determining step, the E and Z products must necessarily have identical enantioenrichment.

-continued

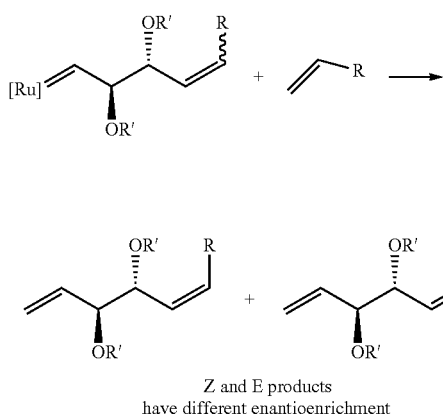

Z and E products have different enantioenrichment

Without being bound by theory, the increased strain and lower steric demand of the cyclobutenes results in propagation through a Ru-alkylidene species, while the bulkier and less strained norbornenes result in propagation through a Ru-methylidene. The absolute configuration of the AROCM products requires that the methylidene intermediate of the cyclobutene AROCM possess the opposite configuration at ruthenium compared to the alkylidene in the norbornene AROCM.

To better understand the impact of concentration and stoichiometry on the AROCM of norbornenes and cyclobutenes, 9b and 9c were reacted with allyl acetate were studied in further detail. In the case of 2,3-di-endo substituted norbornene 9b, the Z/E ratio remained constant and the ee was only slightly affected by concentration and equivalents of olefin (Table 2). A similar independence of diastereoselectivity and ee were observed in the AROCM of cyclobutenes (see Hartung, J.; Grubbs, R. H. *Angew. Chem. Int. Ed.* 2014, 53, 3885-3888).

TABLE 2

Effect of Concentration and Equivalents of Terminal Olefin on the AROCM of Norbornene 9b

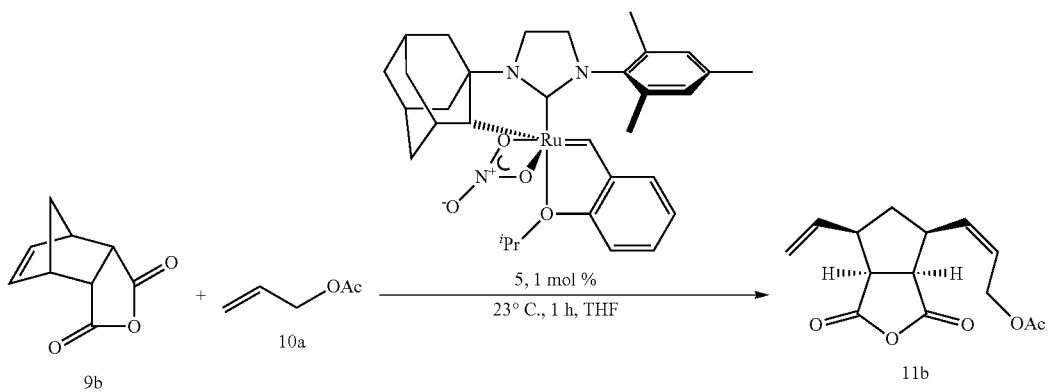

| Concentration (M) | Equiv 10a | Conversion (%)[a] | Z/E ratio[b] | ee (%)[c] |
|---|---|---|---|---|
| 0.05 | 7 | >95[d] | 97:3 | 75 |
| 0.1 | 7 | >95[e] | 97:3 | 74 |
| 0.5 | 7 | >95 | 98:2 | 75 |
| 0.5 | 3 | 60 | 97:3 | 72 |

[a]Determined by 500 MHz $^1$H NMR.
[b]Determined by GC.
[c]Determined by chiral SFC on chromatographically purified products.
[d]Full conversion achieved after 16 h.
[e]Full conversion achieved after 4 h.

While the ee of Z-11c produced by the AROCM of 9c with allyl acetate was unaffected by concentration and equivalents of terminal olefin, the Z/E ratio was dependent on both variables with higher concentration and more terminal olefin favoring Z-11c (Table 3). Thus in the absence of chelating substituents on the strained olefin component, the diastereodetermining cross metathesis with the terminal olefin is dependent on the concentration of the terminal olefin. A similar dependence of olefin geometry on concentration is observed in ROMP catalyzed by homogeneous alkylidene initiators (see Oskam, J. H.; Schrock, R. R. *J. Am. Chem. Soc.* 1993, 115, 11831-11845, Bishop, J. P.; Register, R. A. Polymer 2010, 51, 4121-4126). In ROMP, it has been proposed that the concentration dependence arises from a rate competition between first order rotation of the alkylidene and second order [2+2] cycloaddition with the incoming monomer. Higher concentrations have a greater influence on the second order process. In the current AROCMs, a similar effect likely occurs with the dependence on concentration and the incoming reactant. This dependence suggests that cross metathesis to release the mono-cross product competes with rotation of the alkylidene.

*Am. Chem. Soc.* 2006, 128, 1840-1846, Fournier, P.-A.; Collins, S. K. *Organometallics* 2007, 26, 2945-2949, Fournier, P.-A.; Savoie, J.; Stenne, B.; Bedard, M.; Grandbois, A.; Collins, S. K. *Chem.-Ear. J.* 2008, 14, 8690-8695, Grandbois, A.; Collins, S. K. *Chem.-Eur. J.* 2008, 14, 9323-9329, Savoie, J.; Stenne, B.; Collins, S. K. *Adv. Synth. Catal.* 2009, 351, 1826-1832, Tiede, S.; Berger, A.; Schlesiger, D.; Rost, D.; Lühl, A.; Blechert, S. *Angew. Chem. Int. Ed.* 2010, 49, 3972-3975, Stenne, B.; Timperio, J.; Savoie, J.; Dudding, T.; Collins, S. K. *Org. Lett.* 2010, 12, 2032-2035, Van Veldhuizen, J. J.; Gillingham, D. G.; Garber, S. B.; Kataoka, O.; Hoveyda, A. H. *J. Am. Chem. Soc.* 2003, 125, 12502-12508, Fujimura, O.; Grubbs, R. H. *J. Am. Chem. Soc.* 1996, 118, 2499-2500, Fujimura, O.; Grubbs, R. H. *J. Org. Chem.* 1998, 63, 824-832, Alexander, J. B.; La, D. S.; Cefalo, D. R.; Hoveyda, A. H.; Schrock, R. R. *J. Am. Chem. Soc.* 1998, 120, 4041-4042, La, D. S.; Alexander, J. B.; Cefalo, D. R.; Graf, D. D.; Hoveyda, A. H.; Schrock, R. R. *J. Am. Chem. Soc.* 1998, 120, 9720-9721, Zhu, S. S.; Cefalo, D. R.; La, D. S.; Jamieson, J. Y.; Davis, W. M.;

TABLE 3

Effect of Concentration and Equivalents of Terminal Olefin on the AROCM of Norbornene 9c

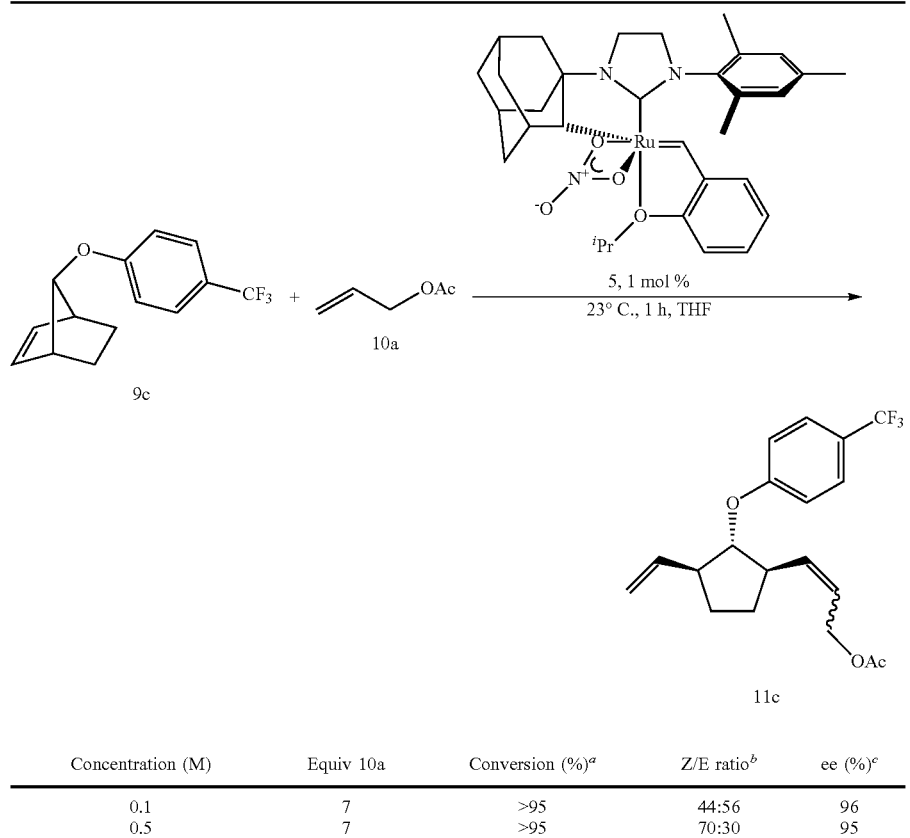

| Concentration (M) | Equiv 10a | Conversion (%)[a] | Z/E ratio[b] | ee (%)[c] |
|---|---|---|---|---|
| 0.1 | 7 | >95 | 44:56 | 96 |
| 0.5 | 7 | >95 | 70:30 | 95 |
| 0.5 | 3 | >95 | 59:41 | 96 |

[a]Determined by 500 MHz $^1$H NMR.
[b]Determined by GC.
[c]Determined by chiral SFC on chromatographically purified products Catalyzed Asymmetric Ring Closing Metathesis A considerable amount of work has been performed on catalyst development and applications for ARCM (see Seiders, T. J.; Ward, D. W.; Grubbs, R. H. *Org. Lett.* 2001, 3, 3225-3228, Funk, T. W.; Berlin, J. M.; Grubbs, R. H. *J.* Hoveyda, A. H.; Schrock, R. R. *J. Am. Chem. Soc.* 1999, 121, 8251-8259, Dolman, S. J.; Sattely, E. S.; Hoveyda, A. H.; Schrock, R. R. *J. Am. Chem. Soc.* 2002, 124, 6991-6997, Weatherhead, G. S.; Houser, J. H.; Ford, J. G.; Jamieson, J. Y.; Schrock, R. R.; Hoveyda, A. H. *Tetrahedron Lett.* 2000, 41, 9553-9559, Cefalo, D. R.; Kiely, A. F.; Wuchrer, M.;

Jamieson, J. Y.; Schrock, R. R.; Hoveyda, A. H. *J. Am. Chem. Soc.* 2001, 123, 3139-3140, Kiely, A. F.; Jernelius, J. A.; Schrock, R. R.; Hoveyda, A. H. *J. Am. Chem. Soc.* 2002, 124, 2868-2869, Dolman, S. J.; Schrock, R. R.; Hoveyda, A. H. *Org. Lett.* 2003, 5, 4899-4902, Tsang, W. C. P.; Hultzsch, K. C.; Alexander, J. B.; Bonitatebus, Peter J.; Schrock, R. R.; Hoveyda, A. H. *J. Am. Chem. Soc.* 2003, 125, 2652-2666, Dolman, S. J.; Hultzsch, K. C.; Pezet, F.; Teng, X.; Hoveyda, A. H.; Schrock, R. R. *J. Am. Chem. Soc.* 2004, 126, 10945-10953, Jernelius, J. A.; Schrock, R. R.; Hoveyda, A. H. *Tetrahedron* 2004, 60, 7345-7351, Sattely, E. S.; Cortez, G. A.; Moebius, D. C.; Schrock, R. R.; Hoveyda, A. H. *J. Am. Chem. Soc.* 2005, 127, 8526-8533, Lee, A.-L.; Malcolmson, S. J.; Puglisi, A.; Schrock, R. R.; Hoveyda, A. H. *J. Am. Chem. Soc.* 2006, 128, 5153-5157, Malcolmson, S. J.; Meek, S. J.; Sattely, E. S.; Schrock, R. R.; Hoveyda, A. H. *Nature* 2008, 456, 933-937, Harvey, J. S.; Malcolmson, S. J.; Dunne, K. S.; Meek, S. J.; Thompson, A. L.; Schrock, R. R.; Hoveyda, A. H.; Gouverneur, V. *Angew. Chem. Int. Ed.* 2009, 48, 762-766, Sattely, E. S.; Meek, S. J.; Malcolmson, S. J.; Schrock, R. R.; Hoveyda, A. H. *J. Am. Chem. Soc.* 2009, 131, 943-953, Ogasawara, M.; Watanabe, S.; Nakajima, K.; Takahashi, T. *J. Am. Chem. Soc.* 2010, 132, 2136-2137, Grisi, F.; Costabile, C.; Gallo, E.; Mariconda, A.; Tedesco, C.; Longo, P. *Organometallics* 2008, 27, 4649-4656, Gawin, R.; Pieczykolan, M.; Malinska, M.; Woiniak, K.; Grela, K. *Synlett* 2013, 24, 1250-1254, Ivry, E.; Ben-Asuly, A.; Goldberg, I.; Lemcoff, G. *Chem. Commun.*, 2015, 51, 3870).

The products of desymmetrizing ARCM are potentially useful in target-oriented synthesis since two differentiated olefins are present in the final enantioenriched product. These olefins provide an ideal platform for further functionalization. ARCM has been used as key step in a number of natural product total syntheses (see Burke, S. D.; Müller, N.; Beaudry, C. M. *Org. Lett.* 1999, 1, 1827-1829, Sattely, E. S.; Cortez, G. A.; Moebius, D. C.; Schrock, R. R.; Hoveyda, A. H. *J. Am. Chem. Soc.* 2005, 127, 8526-8533, Malcolmson, S. J.; Meek, S. J.; Sattely, E. S.; Schrock, R. R.; Hoveyda, A. H. *Nature* 2008, 456, 933-937, Funk, T. W. *Org. Lett.* 2009, 11, 4998-5001, Hoveyda, A. H.; Malcolmson, S. J.; Meek, S. J.; Zhugralin, A. R. *Angew. Chem. Int. Ed* Engl. 2010, 49, 34-44).

Despite much progress, ARCM substrates have largely been limited to cases where the unique olefin is considerably less bulky than the enantiotopic olefin. Only isolated examples of all-terminal trienes lacking allylic quaternary substitution have proven successful, (see Cefalo, D. R.; Kiely, A. F.; Wuchrer, M.; Jamieson, J. Y.; Schrock, R. R.; Hoveyda, A. H. *J. Am. Chem. Soc.* 2001, 123, 3139-3140, Sattely, E. S.; Cortez, G. A.; Moebius, D. C.; Schrock, R. R.; Hoveyda, A. H. *J. Am. Chem. Soc.* 2005, 127, 8526-8533). It is unclear whether the mechanism involves a direct ARCM, or an RCM of the two enantiotopic olefins to generate an achiral cyclopentene, followed by ARCM/ring-opening metathesis isomerization. Furthermore, it has been noted in several reports that attempted ARCM of various all-terminal trienes have been unsuccessful, due either to low ee (see Dolman, S. J.; Sattely, E. S.; Hoveyda, A. H.; Schrock, R. R. *J. Am. Chem. Soc.* 2002, 124, 6991-6997, Weatherhead, G. S.; Houser, J. H.; Ford, J. G.; Jamieson, J. Y.; Schrock, R. R.; Hoveyda, A. H. *Tetrahedron Lett.* 2000, 41, 9553-9559, Lee, A.-L.; Malcolmson, S. J.; Puglisi, A.; Schrock, R. R.; Hoveyda, A. H. *J. Am. Chem. Soc.* 2006, 128, 5153-5157, Ogasawara, M.; Watanabe, S.; Nakajima, K.; Takahashi, T. *J. Am. Chem. Soc.* 2010, 132, 2136-2137) or formation of oligomers (see Kiely, A. F.; Jernelius, J. A.; Schrock, R. R.; Hoveyda, A. H. *J. Am. Chem. Soc.* 2002, 124, 2868-2869). The ARCM of unhindered trienes is particularly challenging due to the difficulty in controlling the cyclization pathway, and the need to differentiate between relatively small enantiotopic groups.

Scheme 6. Possible Pathways to ARCM Products

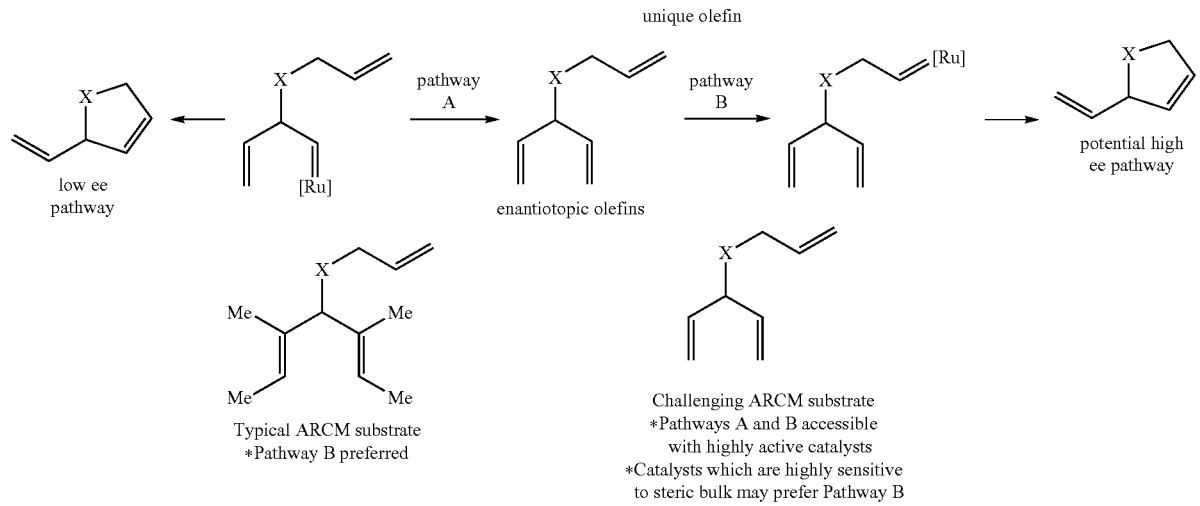

The RCM of prochiral trienes can, in principle, proceed through two distinct pathways (Scheme 6). In pathway A, the initial alkylidene formation occurs on one of the two enantiotopic olefins, followed by cyclization with the unique olefin. If initial alkylidene formation is irreversible, then this step is enantiodiscriminating. In pathway B, initial alkylidene formation occurs with the unique olefin, and this alkylidene subsequently cyclizes with one of the two enantiotopic olefins in the enantiodiscriminating step. To a first approximation, an enantiodiscriminating cyclization step is more likely to be highly enantioselective than alkylidene formation, because of the ordered nature of a cyclic transition state. Furthermore, in order to achieve high enantioselectivity, it is desirable to ensure that only one pathway is operating. Competing pathways will lead to decreased enantioselectivity unless they are both highly enantioselective for the same product enantiomer (an unlikely scenario).

The substitution pattern of the enantiotopic olefins can also impact the relative energy of diastereomeric transition states. Cavallo has performed computational studies on the origin of stereoselectivity with geared NHC Ru complexes (see Costabile, C.; Cavallo, L. *J. Am. Chem. Soc.* 2004, 126, 9592-9600). It was found that the non-reacting olefin is oriented in pseudo-equatorial and pseudo-axial positions in the respective diastereomeric cyclization transition states. Higher selectivities are therefore expected when this substituent is large, leading to a large energy difference between pseudo-equatorial and pseudo-axial configurations.

The necessity of employing highly substituted enantiotopic olefins has limited the potential utility of ARCM products. It was previously been observed that chelated complexes such as (rac)-5 are sensitive to steric bulk at the allylic position (see Quigley, B. L.; Grubbs, R. H. *Chem. Sci.* 2013, 5, 501-506). It was hypothesized that resolved complex 5 would be an ideal candidate for ARCM of trienes such as 13, since this catalyst would likely disfavor intermolecular cross metathesis of the enantiotopic olefins and favor initial reaction with the allyl fragment. This preference would bias the system to undergo enantiodetermining ring closing metathesis, a pathway that is likely to lead to higher enantioinduction. Success of this strategy would improve the scope of the ARCM reaction by allowing the generation of cyclic products lacking the cumbersome substitution on the resultant product alkenes.

Furthermore, to determine whether the addition of further steric bulk, through modification of the X-type ligand, could positively impact enantioselectivities, complexes 6a'-6h' were prepared by ligand exchange from enantioenriched iodide 7 (Scheme 7). This reaction proceeded rapidly and afforded products of sufficient purity after concentration, re-dissolution in benzene, and filtration through a short plug of Celite.

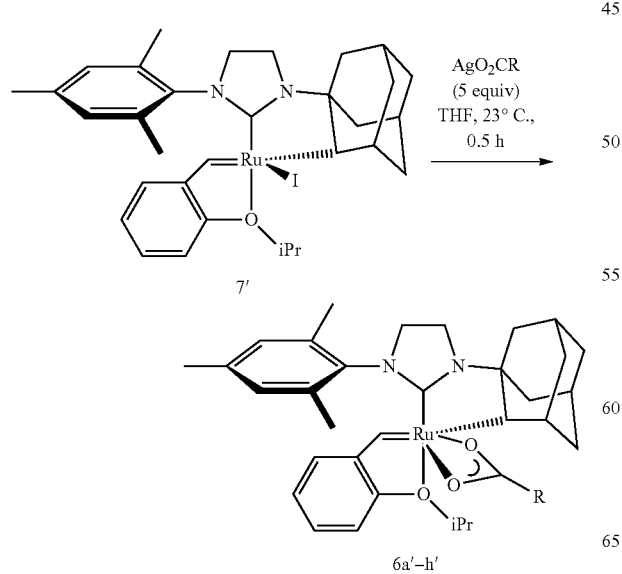

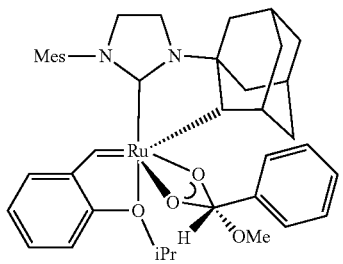

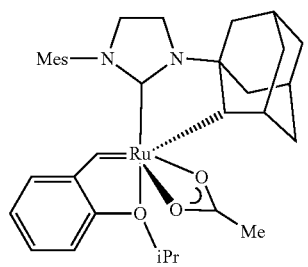

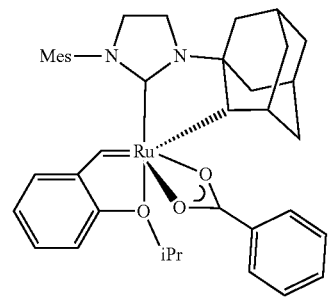

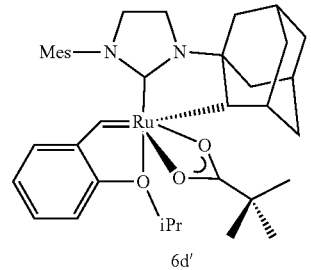

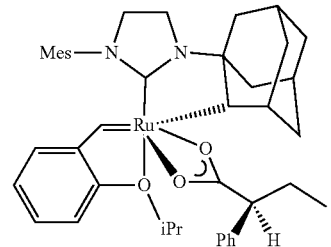

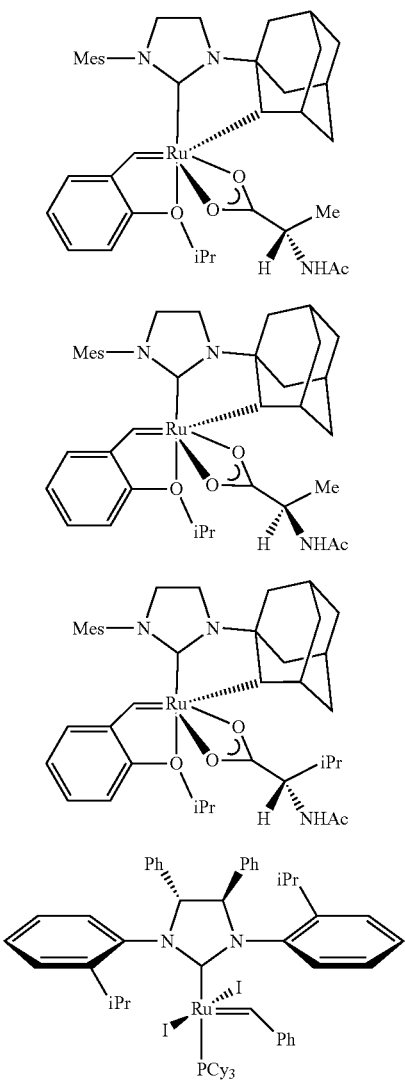

Complexes containing achiral carboxylates (6b'-6d') and enantiopure carboxylates (6a', 6e'-6h') were obtained. While the cyclometalated iodide complex was inactive in RCM, all of the carboxylates were found to be competent catalysts with varying levels of enantioselectivity (Table 4). Thus, while $\kappa^2$ (bidentate) ligands are more active than monodentate ligands, the electronics and sterics of the carboxylate ligand also impact the ARCM reaction.

TABLE 4

Efficiency and Enantioselectivity of 6a'-6h' in ARCM of 13.

| Entry | Catalyst | Conversion (%)[a] | ee (%)[b] |
|---|---|---|---|
| 1 | 7' | <2 | ND |
| 2 | 6a' | >98 | 42 |
| 3 | 6b' | 35 | 36 |
| 4 | 6c' | 35 | 53 |
| 5 | 6d' | 76 | 46 |
| 6 | 6e' | >98 | 18 |
| 7 | 6f' | >98 | 42 |
| 8 | 6g' | 48 | 43 |
| 9 | 6h' | 72 | 40 |
| 10 | 5 | >98 | 54 |
| 11 | 1 | 20 | 0 |

[a]Determined by $^1$NMR spectroscopy;
[b]determined by chiral SFC analysis

More substituted aliphatic carboxylates, such as the pivalate 6d' and N-acetyl amino carboxylates 6f'-6h', were more competent catalysts than acetate 6b', forming the product in essentially full conversion (entries 5, 7-9). While the steric bulk of the amino acid side chain had little bearing on the enantioselectivity (no difference was observed between alanine and valine), the presence of an electron-withdrawing heteroatom in the alpha position of the carboxylate afforded a more enantioselective catalyst. For example, the 2-phenylbutyric acid-derived catalyst 6e' generated the product in only 18% ee, while the relatively isosteric O-methyl mandelate 6a' provided 13 in 42% ee (entries 6 and 2). Complexes 6a'-6h' possess opposite stereochemistry at ruthenium and the adamantyl stereocenter to that of 5 (nitrate), and all favored the opposite product enantiomer. This indicates that the ruthenium and adamantyl stereocenters are the primary determinants of the sense of enantioinduction. The stereochemistry of the carboxylate has little influence on the stereochemical outcome of the ARCM as complexes 6f' and 6g', containing either D- or L-alanine carboxylates, gave identical ee (entries 7 and 8). The nitrate catalyst 5 (98% conversion, 54% ee, entry 10) thus was a significant improvement to the previous generation geared catalyst 1 (20% conversion, 0% ee, entry 11) and sought to study the reaction scope enabled by this advance.

TABLE 5

Scope of ARCM reaction with 5[a]

| Entry | Substrate | Product | Conversion (%) | Yield (%) | ee (%) |
|---|---|---|---|---|---|
| 1 | 15 | 16 | >98 | 65[b] | 69 |

TABLE 5-continued

Scope of ARCM reaction with 5[a]

| Entry | Substrate | Product | Conversion (%) | Yield (%) | ee (%) |
|---|---|---|---|---|---|
| 2 | 17 | 18 | 63[c] | 29 | 68 |
| 3 | 19 | 20 | 0 | — | — |
| 4 | 13 | 14 | >98 | 95 | 54 |
| 5 | 21 | 22 | >98 | 90 | 57 |
| 6 | 23 | 24 | 0 | — | — |
| 7 | 25 | 26 | >98 | 72 | 47 |

[a]Reaction conditions: triene (0.5M), 5 (5 mol %), THF, 23° C., 24 h
[b]Determined by $^1$H NMR using mesitylene as an internal standard.
[c]Using 10 mol % catalyst.

To probe the influence of substitution in the allylic position, nature of the heteroatom, and ring size on the efficiency and enantioselectivity, prochiral trienes composed of monosubstituted olefins were cyclized cleanly, resulting in generally high yields (Table 5). Moving from a dimethyl siloxy to the bulkier diphenyl siloxy tether resulted in a slower cyclization and required an increase in catalyst loading to achieve good conversion (entries 1 and 2). Triene 19, which contains trisubstituted enantiotopic olefins, did not undergo ring closure (entry 3). Saturated nitrogen-containing heterocycles were formed in high yield and moderate enantioselectivity, (entries 4 and 5).

A particularly challenging substrate 23, bearing a fully-substituted carbon in the allylic position of the 1,4-diene moiety, completely shut down the reaction (entry 6). On the other hand, the presence of a fully substituted carbon in the homoallylic position, as in 25, restored reactivity (Entry 7). These results suggest that reducing the steric bulk of the catalyst, perhaps by the use of alternative cyclometalated NHC ligands, may expand the scope of the reaction to form synthetically challenging tertiary ether products.

Triene 27, containing a homoallyl diphenyl silyl group, was synthesized in order to test the efficiency of forming seven membered rings. In contrast to triene 17, 27 underwent ring closure under the standard conditions in good yield, indicating that the additional methylene unit was sufficient to relieve the steric bulk of the diphenylsilyl unit. Surprisingly, the product was racemic. In order to probe whether enantioselectivity is lost due to reversibility, the reaction was performed in a sealed NMR tube and monitored by $^1$H NMR. After 4 hr, 71% conversion had been achieved. However, the reaction eventually stalled at 78% conversion despite still containing pre-catalyst. Upon purging ethylene from the NMR tube, the reaction resumed and eventually reached 92% conversion. This result suggests that in a closed vessel, the RCM is reversible, and equilibrium can be reached prior to full conversion. The reversibility of the reaction erodes any enantioenrichment that is initially achieved. Therefore efficient removal of ethylene is required to obtain enantioenrichment.

In order to remove ethylene during the course of the ARCM reaction, the reaction was performed in an open vial in a nitrogen filled glove box (Scheme 8a). After 24 h, full conversion of starting material was achieved, and the 7-membered product was generated in 37% ee. This result suggests that removal of ethylene limits reversibility and demonstrates the importance of assessing reversibility in ARCM reactions. Triene 13 was also subjected to open vial conditions (Scheme 8b). Although reactivity was slightly diminished relative to closed vial conditions, the product was generated in an almost identical 58% ee, (compared to 54% ee for closed vial). In both cases, solvent evaporated quickly, and the reaction mixture became viscous. This change in reaction medium may explain the small increase in ee (from 54 to 58) with triene 13. Therefore reversibility is not significant with triene 13. The reversible nature of the ARCM of 27, but not 13, is most likely due to the increased ring strain of 28.

Scheme 8a. Effect of open vial on enantioselectivity in ARCM of triene 27;

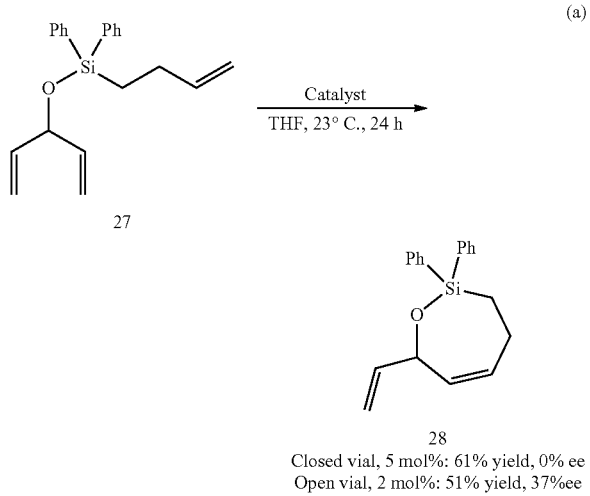

Closed vial, 5 mol%: 61% yield, 0% ee
Open vial, 2 mol%: 51% yield, 37%ee

Scheme 8b. Effect of open vial on enantioselectivity in ARCM of triene 13.

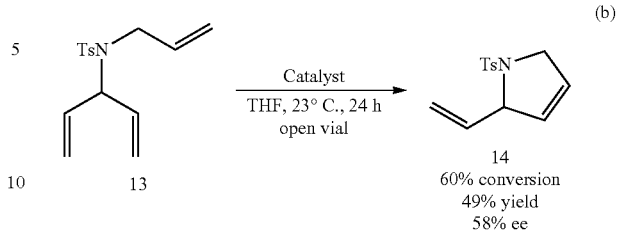

14
60% conversion
49% yield
58% ee

The absolute configuration of diene 14 was determined by X-ray crystallographic analysis to be (2S). On the basis of the absolute configuration of 14, without being bound by theory, enantioinduction likely arises from the favorable conformational effect of placing the unreacted vinyl group of the 1,4-diene fragment in a pseudo-equatorial, as opposed to pseudo-axial, orientation.

Catalyzed Asymmetric Cross Metathesis

Cross metathesis of prochiral 1,4- or 1,5- or 1,6-dienes to afford desymmetrized metathesis products has remained an elusive method for the construction of allylic and homoallylic stereocenters. The lack of success is likely due to three factors: 1) difficulty in controlling the nature of the propagating species; 2) limiting secondary metathesis events resulting in symmetrical products; and 3) designing a chiral environment capable of high levels of enantioinduction. However, a previous example of ACM suggested that enantiopure Ru-based metathesis catalysts are capable of desymmetrizing cross metathesis, although in modest yields (17-54%) and ee's (4-52%), (see Berlin, J. M.; Goldberg, S. D.; Grubbs, R. H. *Angew. Chem. Int. Ed.* 2006, 45, 7591-7595).

After optimization of reaction conditions, it was observed that cyclometalated complex 5 catalyzes the ACM of 1,4 diene 29 with cis-1,4-diacetoxy-2-butene 30 in 35% yield and with a promising ee of 50% (Eq. 1). In contrast to the previous report of E-selective ACM with $C_2$-symmetric catalysts, this method provides exclusively the Z-isomer. These results suggest that further optimization of the ligand set and choice of the proper substitution on the pro-stereogenic carbon atom of the diene reactant may result in highly enantioenriched 1,4-diene products, which will be useful chiral building blocks in complex molecule synthesis.

Cyclometalated ruthenium complexes, which are resolved by chromatographic separation and readily diversified by ligand exchange, have demonstrated high levels of enantioinduction in the reaction manifolds comprising enantioselective olefin metathesis. AROCM of cyclobutenes and norbornenes with 5 afforded, in many cases, highly Z and enantioenriched 1,4- and 1,6-dienes, respectively. In comparison to previous generations of $C_2$ symmetric ruthenium alkylidenes, complexes 5 and 6 are capable of desymmetrizing prochiral trienes composed solely of monosubstituted olefins. Preliminary results suggest that 5 is capable of ACM with a level of enantioselectivity on par with the state of the art, and complementary in its ability to afford Z products.

(Eq. 1)

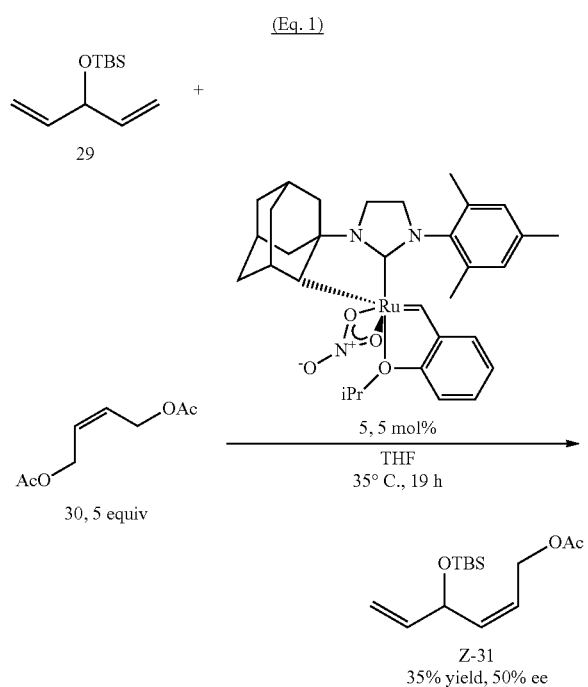

Z-31
35% yield, 50% ee

TABLE S1

Optimizing of ACM Reaction of 29 with rac-5[a]

| Equiv. 29 | Cross partner | Equiv. of Cross partner | Cat. Loading (%) | mL THF | Yield Z-31 (%)[b] |
|---|---|---|---|---|---|
| 1 | allyl acetate | 5 | 5 | 0.3 | 15 |
| 5 | allyl acetate | 1 | 5 | 0.3 | 35 |
| 1 | Cis-1,4-diacetoxy-2-butene | 5 | 5 | 0.3 | 35 |
| 1 | Cis-1,4-diacetoxy-2-butene | 5 | 2.5 | 0.3 | 35 |
| 1 | Cis-1,4-diacetoxy-2-butene | 5 | 1 | 0.3 | 6 |
| 1 | Cis-1,4-diacetoxy-2-butene | 5 | 5 | 0.2 | 30 |
| 1 | Cis-1,4-diacetoxy-2-butene | 5 | 5 | 0.1 | 30 |

[a] All reactions conducted with 0.1 mmol of limiting reagent at 35° C. for 18 h in an open vial under inert atmosphere (glove box);
[b] Yield with respect to limiting reactant; determined by integration relative to an internal standard (mesitylene) in the $^1$H NMR of the crude reaction mixture.

Based on these reactions, control of the active catalytic species through the manipulation of several experimental variables can greatly influence the outcome of the enantioselective olefin metathesis reactions. The influence of ring strain and steric bulk of the strained olefin on the mechanism of AROCM has led to a hypothesis for the active catalyst species in reactions catalyzed by 5. The efficiency and enantioselectivity of ARCM reactions catalyzed by cyclometalated catalysts is a function of both the X-type ligand and substitution pattern on the prochiral triene reactant. In cases where a medium-sized ring is formed, efficient removal of ethylene is required to prevent reversibility, which would otherwise erode enantioselectivity.

It is to be understood that while the invention has been described in conjunction with specific embodiments thereof, that the description above as well as the examples that follow are intended to illustrate and not limit the scope of the invention. Other aspects, advantages, and modifications within the scope of the invention will be apparent to those skilled in the art to which the invention pertains.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees Celsius and pressure is at or near atmospheric. The examples are to be considered as not being limiting of the invention as described herein and are instead provided as representative examples of the catalyst compounds of the invention, the methods that may be used in their preparation, and the methods of using the inventive catalysts.

All reactions were carried out in dry glassware under an Argon atmosphere using standard Schlenk line techniques or in a Vacuum Atmospheres glovebox under nitrogen atmosphere. All solvents were purified by passage through solvent purification columns and further degassed with Argon (Pangborn, A. B.; Giardello, M. A.; Grubbs, R. H.; Rosen, R. K.; Timmers, F. J., Organometallics 1996, 15, 1518-1520). NMR solvents for air-sensitive compounds were degassed by sparging with nitrogen and passed through a solvent purification column prior to use. $C_6D_6$ was purified by passage through a solvent purification column and degassed prior to use. DCM and $CDCl_3$ used for the analysis of CM reactions were filtered through a plug of basic alumina prior to use. Commercially available reagents were used as received unless otherwise noted. Substrates in the liquid state were degassed with Argon and passed through a plug of neutral alumina prior to use. Diglyme was sparged with Ar, stored over 4 Å molecular sieves and filtered over basic alumina prior to use. MeOH used in the preparation of metathesis catalysts was dried over 3 Å molecular sieves, distilled from $CaH_2$ and degassed by sparging with Ar prior to use. Other solvents involved in the reaction or preparation of organometallic species were purified by passage through solvent purification columns and degassed prior to use. Solid substrates were used after purification by silica gel column chromatography. Silica gel used for the purification of transition metal complexes was dried at 220° C. and 100 mTorr for 24 h prior to use. Flash chromatography was carried out with silica gel 60 (230-400 mesh). Other starting materials were prepared according to previously reported procedures and matched previously reported literature data.

Standard NMR spectroscopy experiments were conducted on a Varian NOVA 500 ($^1$H: 500 MHz, $^{13}$C: 125 MHz) spectrometer. Chemical shifts are referenced to the residual solvent peak ($CDCl_3$ or $C_6D_6$) multiplicity is reported as follows: (s: singlet, d: doublet, t: triplet, q: quartet, br: broad, m: multiplet). Spectra were analyzed and processed using MestReNova.

High-resolution mass spectra (HRMS) data was obtained on a JEOL MSRoute mass spectrometer using FAB+, EI+, or MALDI-TOF methods.

Analytical SFC data was obtained on a Mettler SFC supercritical $CO_2$ analytical chromatography system equipped with Chiracel OD-H, OJ-H or Chirapak AD-H columns (4.6 mm×25 cm). Column temperature was maintained at 40° C. Optical rotations were measured on a Jasco P-2000 polarimeter using a 100 mm path-length cell at 589 nm.

Gas chromatography data was obtained using an Agilent 6850 FID gas chromatograph equipped with a HP-5 (5%-phenyl)-methylpolysiloxane capillary column (Agilent). High-resolution mass spectroscopy was completed at the California Institute of Technology Mass Spectrometry Facility. NMR spectra were recorded on a Varian Inova 400 (400 MHz for $^1$H, 128 MHz for $^{11}$B, 101 MHz for $^{13}$C), automated Varian Inova 500 (500 MHz for $^1$H, 126 MHz for $^{13}$C), Varian Inova 600 (500 MHz for $^1$H, 151 MHz for $^{13}$C) or Bruker Avance III 400 (400 MHz for $^1$H, 101 MHz for $^{13}$C). $^1$H and $^{13}$C chemical shifts are expressed in ppm downfield from tetramethylsilane using the residual protiated solvent (for $^1$H) or the solvent (for $^{13}$C) as an internal standard (CDCl$_3$ $^1$H: 7.26 ppm and $^{13}$C: 77.2 ppm; DMSO-d$^6$ $^1$H: 2.50 ppm and $^{13}$C: 39.5 ppm; CD$_3$OD $^1$H: 3.31 ppm and $^{13}$C: 49.0 ppm). $^{19}$F chemical shifts are expressed in ppm downfield from CFCl$_3$ using the deuterium signal of the solvent as an internal standard.

The following abbreviations are used in the examples:

| | |
|---|---|
| RT or r.t. | room temperature |
| MeOH | methanol |
| mL | milliliter |
| CDCl$_3$ | deuterated chloroform |
| C$_6$D$_6$ | deuterated benzene |
| CD$_2$Cl$_2$ | deuterated dichloromethane |
| K$_2$CO$_3$ | potassium carbonate |
| BH$_3$ | borane |
| THF | tetrahydrofuran |
| HCl | hydrochloric acid |
| Et$_2$O | diethylether |
| HC(OEt)$_3$ | triethyl orthoformate |
| KHMDS | potassium bis(trimethylsilyl)amide |

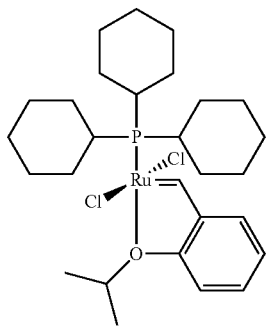

| | |
|---|---|
| C601 | [CAS203714-71-0] |
| ° C. | degrees Celsius |
| NH$_4$NO$_3$ | ammonium nitrate |
| NaOPiv | sodium pivalate |
| TEA | triethylamine |
| DCM | dichloromethane |
| MeCN | acetonitrile |
| SiO$_2$ | silicagel |
| Al$_2$O$_3$ | aluminum oxide |
| LiAlH$_4$ | lithium aluminium hydrate |
| EtOAc | ethylacetate |
| MeOH | methanol |
| DPPA | diphenylphosphoryl azide |
| CD$_3$OD | deuterated methanol |
| DMSO-d$^6$ | deuterated dimethylsulfoxide |
| CaH$_2$ | calcium hydride |
| MgSO$_4$ | magnesium sulfate |
| NaHCO$_3$ | sodium hydrogen carbonate |
| I$_2$ | iodine |
| PBr$_3$ | phosphorus tribromide |
| TLC | thin layer chromatography |
| Na$_2$SO$_4$ | sodium sulfate |
| NH$_4$Cl | ammonium chloride |
| KH | potassium hydride |
| HMPA | hexamethylphosphoramide |

Mes

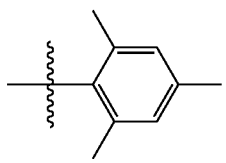 [SMILES: *c1c(C)cc(C)cc1C]

DIPP

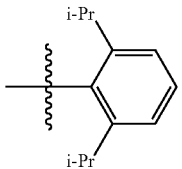 [SMILES: *c1c(C(C)C)cccc1C(C)C]

Resolution of Complex Rac-5

Complex rac-5 was resolved according to the procedure previously reported (see Hartung, J.; Grubbs, R. H. *J. Am. Chem. Soc.* 2013, 135, 10183-10185). A modification of the original procedure is described herein. The mixture of diastereomers 6a and 6a' (Scheme 3) (0.345 g, 0.464 mmol) were triturated with 1:1 Et$_2$O/pentane (5×10 mL) at 23° C. under a N$_2$ atmosphere. The remaining solid was dried under vacuum and assayed by $^1$H NMR (>95% de 6a, 84.6 mg, 0.115 mmol, 49% of theoretical yield).

Complex rac-5 was resolved according to the procedure previously reported (see Hartung, J.; Grubbs, R. H. *J. Am. Chem. Soc.* 2013, 135, 10183-10185). A modification of the original procedure is described herein. The mixture of diastereomers 6a and 6a' (Scheme 3) (0.260 g, 0.349 mmol) were triturated with 1:1 Et$_2$O/pentane (5×3 mL) at 23° C. under a N$_2$ atmosphere. The remaining solid was dried under vacuum and assayed by $^1$H NMR (>95% de 6a, 100 mg, 0.136 mmol, 77% of theoretical yield).

Synthesis of Substrates for AROCM

Substrates for AROCM were synthesized as previously reported in the literature: 9d (see La, D. S.; Sattely, E. S.; Ford, J. G.; Schrock, R. R.; Hoveyda, A. H. *J. Am. Chem. Soc.* 2001, 123, 7767-7778), 9e (see Coe, J. W.; Wirtz, M. C.; Bashore, C. G.; Candler, J. *Org. Lett.* 2004, 6, 1589-1592) were synthesized according to the provided references.

General Procedure for AROCM

In a glovebox, alkene 9d (40 mg, 0.2 mmol, 1 equiv) and allyl acetate (140 mg, 1.4 mmol, 7 equiv) were dissolved in 0.4 mL THF. To this solution was added catalyst 5 (1.27 mg, 0.002 mmol). The reaction vial was capped and stirred for 1 h and then quenched with an excess of ethyl vinyl ether. The reaction mixture was concentrated and conversion was determined by 500 MHz $^1$H NMR. The crude was subjected to flash chromatography or preparative TLC to afford the desired ARCM product (11d, 33 mg, 56% yield, 15:85 Z/E ratio, 94% ee (Z), 93% ee (E)). Pure products were submitted to analytical SFC to determine ee.

Characterization Data for AROCM Products

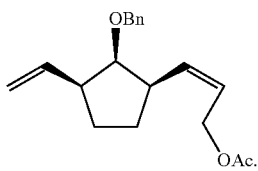

Z-11d $[\alpha]_D^{25}$=23.9° (c=0.21, CHCl$_3$); $^1$H NMR (500 MHz, CDCl$_3$) δ 7.35-7.24 (m, 5H), 5.99 (ddd, J=17.1, 10.2, 8.2 Hz, 1H), 5.90-5.83 (m, 1H), 5.55 (dtd, J=11.1, 7.0, 1.0 Hz, 1H), 5.08 (ddd, J=17.2, 2.1, 1.0 Hz, 1H), 5.02 (ddd, J=10.2, 2.0, 0.8 Hz, 1H), 4.62 (dt, J=7.1, 1.1 Hz, 2H), 4.55 (d, J=11.7 Hz, 1H), 4.50 (d, J=11.7 Hz, 1H), 3.76 (t, J=4.1 Hz, 1H), 2.91

(qd, J=9.1, 4.3 Hz, 1H), 2.62 (qd, J=8.6, 3.9 Hz, 1H), 2.06 (s, 2H), 1.82 (dq, J=9.4, 6.9 Hz, 3H), 1.75-1.67 (m, 1H). $^{13}$C NMR (125 MHz, CDCl$_3$) δ 139.25, 139.09, 136.26, 128.34, 127.74, 127.52, 123.45, 115.04, 86.93, 73.76, 60.77, 50.32, 43.45, 30.53, 30.11, 28.99, 21.14. HRMS (FAB+) calculated for C$_{19}$H$_{24}$NaO$_3$ [M+Na]: 323.1623. found 323.1627.

Separation conditions: OJ-H, 1% IPA, 2.5 mL/min. 94% ee

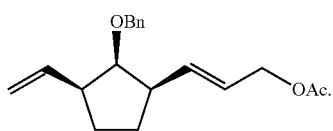

E-11d $[α]_D^{25}$=−1.1° (c=0.67, CHCl$_3$); $^1$H NMR (500 MHz, CDCl$_3$) δ 7.40-7.23 (m, 5H), 6.07-5.97 (m, 1H), 5.95-5.88 (m, 1H), 5.61 (dt, J=15.8, 6.4 Hz, 1H), 5.09 (d, J=17.3 Hz, 1H), 5.03 (dd, J=10.4, 1.9 Hz, 1H), 4.57 (d, J=11.9 Hz, 1H), 4.54-4.51 (m, 2H), 4.49 (dd, J=11.8, 1.5 Hz, 1H), 3.79 (t, J=4.3 Hz, 1H), 2.62 (dt, J=9.7, 4.6 Hz, 2H), 2.05 (d, J=1.5 Hz, 3H), 1.87-1.75 (m, 4H). $^{13}$C NMR (125 MHz, CDCl$_3$) δ 139.37, 139.10, 136.73, 128.31, 127.82, 127.53, 124.18, 114.96, 86.98, 73.70, 65.35, 50.14, 48.54, 28.91, 21.11. HRMS (FAB+) calculated for C$_{19}$H$_{24}$NaO$_3$ [M+Na]: 323.1623. found 323.1628.

Separation conditions: AD-H, 2% IPA, 2.5 mL/min. 93% ee

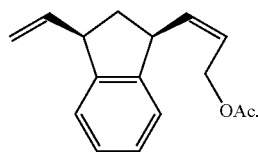

Z-11e

55% yield, 76:14 Z/E ratio.

Z-11e: $[α]_D^{25}$+41.4° (c=0.65, CHCl$_3$); $^1$H NMR (500 MHz, CDCl$_3$) δ 7.25-7.20 (m, 2H), 7.19-7.14 (m, 1H), 7.11-7.07 (m, 1H), 5.89-5.81 (m, 1H), 5.80-5.75 (m, 1H), 5.67 (ddd, J=10.7, 9.6, 1.1 Hz, 1H), 5.25 (ddd, J=17.0, 1.9, 1.0 Hz, 1H), 5.18 (dd, J=10.0, 1.8 Hz, 1H), 4.78 (dt, J=6.9, 1.0 Hz, 2H), 4.15-4.03 (m, 1H), 3.76 (dt, J=10.3, 7.7 Hz, 1H), 2.54 (dt, J=12.3, 7.0 Hz, 1H), 2.11 (d, J=0.8 Hz, 2H), 1.64 (dt, J=12.2, 10.5 Hz, 1H). $^{13}$C NMR (125 MHz, CDCl$_3$) δ 145.72, 145.25, 140.55, 137.57, 127.04, 124.77, 124.30, 124.12, 116.02, 60.59, 49.13, 42.79, 41.59, 21.16. HRMS (FAB+) calculated for C$_{16}$H$_{17}$O$_2$ [M+H−H$_2$]: 241.1229. found 241.1221.

Separation conditions: AD-H, 3% IPA, 2.5 mL/min.>98% ee

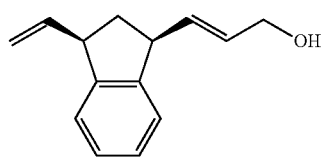

S1

E-11e was deacetylated to the compound shown above in order to aid purification.

$^1$H NMR (500 MHz, CDCl$_3$) δ 7.25-7.10 (m, 3H), 5.91-5.79 (m, 2H), 5.77-5.69 (m, 1H), 5.22 (ddd, J=17.1, 1.8, 0.9 Hz, 1H), 5.15 (dd, J=10.0, 1.9 Hz, 1H), 4.20 (t, J=5.7 Hz, 2H), 3.73 (dq, J=16.8, 8.3 Hz, 2H), 2.52 (dt, J=12.4, 7.1 Hz, 1H), 1.66 (dt, J=12.4, 10.3 Hz, 1H), 1.32 (t, J=5.7 Hz, 1H).

Z and E isomers of Si were hydrogenated (H$_2$, 1 atm, 10% Pd/H, EtOAc) to afford the tetrahydro derivative. $^1$H NMR (500 MHz, CDCl$_3$) δ 7.25-7.14 (m, 4H), 3.78-3.66 (m, 2H), 3.13-2.90 (m, 3H), 2.53 (ddt, J=20.8, 12.3, 6.8 Hz, 2H), 2.22-2.00 (m, 2H), 1.83-1.63 (m, 1H), 1.48-1.35 (m, 2H), 1.05-0.97 (m, 3H). $^{13}$C NMR (125 MHz, CDCl$_3$) δ 147.67, 147.50, 126.46, 126.41, 123.40, 123.30, 63.42, 45.30, 43.39, 39.23, 31.15, 31.04, 29.86, 27.67, 26.94, 12.05. HRMS (EI+) calculated for C$_{14}$H$_{20}$O [M+]: 204.1514. found 204.1517.

Separation Conditions: AD-H, 3% IPA, 2.5 mL/min

Preparation of Silver Carboxylates

Following a known procedure, (see Dorta, R.; Shimon, L.; Milstein, D. *J. Organomet. Chem.* 2004, 689, 751-758), L-N-acetyl alanine (200 mg, 1.53 mmol, 2 equiv.) was added to a stirring suspension of silver oxide (177 mg, 0.762 mmol, 1 equiv.) in 4 mL acetonitrile, shielded from light. The reaction was vigorously stirred for 24 h, at which time a light gray precipitate had formed. The mixture was filtered and washed with acetonitrile and ether. The resultant solid was dried under vacuum overnight while shielded from light to provide 268 mg (1.13 mmol, 74% yield) of the silver carboxylate. $^1$H NMR (500 MHz, DMSO-d$_6$) δ 7.76 (d, J=7.7 Hz, 1H), 4.15 (p, J=7.2 Hz, 1H), 1.80 (s, 3H), 1.21 (d, J=7.2 Hz, 3H). $^{13}$C NMR (125 MHz, DMSO-d$_6$) δ 176.19, 168.11, 49.43, 22.68, 19.15.

The above procedure was followed substituting L-N-acetyl valine (200 mg, 1.26 mmol) for L-N-acetyl alanine to afford the corresponding silver carboxylate (121 mg, 0.457 mmol, 36% yield). $^1$H NMR (500 MHz, DMSO-d$_6$) δ 7.53 (d, J=9.0 Hz, 1H), 4.10 (dd, J=9.0, 5.3 Hz, 1H), 2.02 (m, 1H), 1.84 (s, 3H), 0.81 (d, J=6.8 Hz, 6H). $^{13}$C NMR (125 MHz, DMSO-d$_6$) δ 175.40, 169.28, 59.43, 31.03, 22.88, 19.77, 18.51.

The above procedure was followed substituting (S)-2-phenyl butyric acid (200 mg, 1.22 mmol) for L-N acetyl alanine to afford the corresponding silver carboxylate (212 mg, 0.785 mmol, 64% yield). $^1$H NMR (500 MHz, DMSO-d$_6$) δ 7.30-7.25 (m, 2H), 7.25-7.20 (m, 2H), 7.16-7.11 (m, 1H), 3.37-3.27 (m, 1H), 1.99-1.88 (m, 1H), 1.60 (m, 1H), 0.79 (t, J=7.3 Hz, 3H). $^{13}$C NMR (125 MHz, DMSO-d$_6$) δ 177.56, 142.76, 128.07, 128.05, 126.09, 56.10, 27.56, 12.88.

Preparation of Catalysts 6b'-h'

To a solution of enantiopure ruthenium iodide 7' (1.92 mg, 0.0028 mmol) in 0.5 mL THF was added silver carboxylate from above (1.3 mg, 0.055 mmol, 2 equiv.). The mixture was stirred for 30 min and then concentrated. The resultant solid was redissolved in benzene and filtered through a short pad of Celite. The resultant purple solution was concentrated, assayed by $^1$H NMR and then used directly in the ARCM reaction. $^1$NMR spectra of complexes 6b'-d' matched previously reported spectra of the corresponding racemic complexes (see Keitz, B. K.; Endo, K.; Patel, P. R.; Herbert, M. B.; Grubbs, R. H. *J. Am. Chem. Soc.*, 2012, 134, 693-699). Diagnostic benzylidene signals (C$_6$D$_6$) of novel compounds are listed below:

6a': 15.00 ppm
6e': 14.99 ppm
6f': 15.10 ppm
6h': 15.11 ppm

Synthesis of Substrates for ARCM

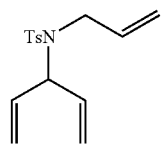

13

A procedure adapted from Jeong et al. (see Jeong, N.; Kim, D. H.; Choi, J. H. *Chem. Commun.* 2004, 1134) was used:

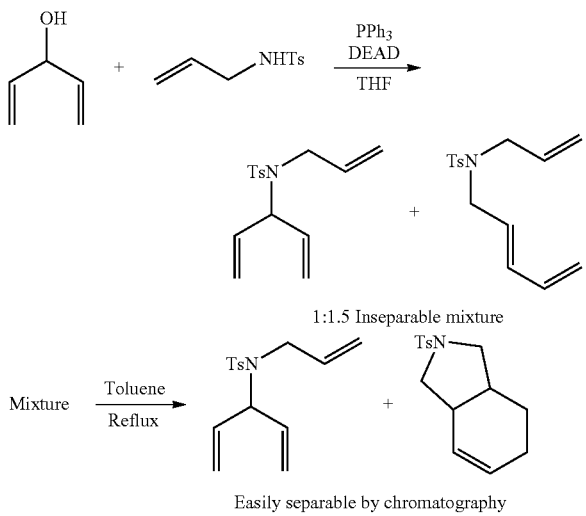

To a flame dried round bottom flask was added N-tosyl allyl amine (4.23 g, 20 mmol, 1.0 eq), triphenylphosphine (6.56 g, 25 mmol, 1.25 eq), THF (100 mL) and 1,4-pentadien-3-ol (2.43 mL, 25 mmol, 1.25 eq). The mixture was cooled to 0° C., and then diethylazodicarboxylate (40 wt % in Toluene, 11.38 mL, 25 mmol, 1.25 eq). The mixture was stirred at 0° C. for 30 min and then warmed to ambient temperature for 12 hr. The reaction was quenched with saturated NaHCO$_3$ and extracted with ether (3×30 mL). The combined organic extracts were washed with brine (30 mL), dried with MgSO$_4$ and concentrated in vacuo. Ether (30 mL) was then added, and the mixture was filtered on a glass frit to remove triphenylphosphine oxide. The solid was washed with ether, and the filtrate was concentrated in vacuo. The material was purified by column chromatography (10% ethyl acetate/hexanes) to yield 3.386 g of an inseparable mixture of the title compound and the corresponding S$_N$2' conjugated diene product in a 1:1.5 ratio. This mixture was dissolved in Toluene (24 mL) and heated to reflux for 22 hr in order to convert the undesired conjugated diene to the Diels Alder adduct. Compound 13 was then purified by column chromatography (7.5% ethyl acetate/hexanes) to give a clear oil (960 mg, 17%). $^1$H NMR (500 MHz, CDCl$_3$) δ 7.71 (d, J=8.3 Hz, 2H), 7.28-7.25 (m, 2H), 5.81-5.73 (m, 3H), 5.19 (dt, J=10.4, 1.3 Hz, 2H), 5.16 (m, 3H), 5.07 (dq, J=10.2, 1.4 Hz, 1H), 4.96 (tt, J=6.0, 1.6 Hz, 1H), 3.78 (dt, J=6.1, 1.5 Hz, 2H), 2.41 (s, 3H); $^{13}$C NMR (126 MHz, CDCl$_3$) δ 143.2, 138.2, 135.7, 135.3, 129.6, 127.6, 118.7, 117.5, 62.4, 47.7, 21.6. HRMS (FAB+) m/z calculated for [C$_{15}$H$_{19}$NSO$_2$+H]$^+$: 278.1215. found: 278.1221.

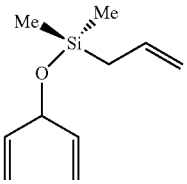

15

To a flame dried flask under argon was added CH$_2$Cl$_2$ (60 mL), 4-dimethylaminopyridine (88 mg, 0.72 mmol, 0.05 eq), triethylamine (2.4 mL, 17.2 mmol, 1.2 eq), 1,4-pentadien-3-ol (1.38 mL, 14.1 mmol, 1.0 eq) and then allyldimethylsilyl chloride (2.2 mL, 15.0 mmol, 1.06 mmol). The mixture was stirred at room temperature for 20 hr, and then quenched with H$_2$O (20 mL). The organic phase was separated, and the aqueous phase was extracted with CH$_2$Cl$_2$ (2×20 mL). The combined organic extracts were washed with brine (20 mL), dried with Na$_2$SO$_4$ and concentrated in vacuo. The crude material was passed through a pad of neutral alumina with 5% ether in pentane and then concentrated in vacuo to give 15 (2.46 g, 96%). $^1$H NMR (500 MHz, CDCl$_3$) δ 5.82 (ddd, J=17.1, 10.3, 5.7 Hz, 2H), 5.83-5.74 (m, 1H), 5.22 (dt, J=17.1, 1.6 Hz, 2H), 5.09 (dt, J=10.3, 1.5 Hz, 2H), 4.92-4.84 (m, 2H), 4.62 (tp, J=5.7, 1.5 Hz, 1H), 1.65 (dt, J=8.1, 1.2 Hz, 2H), 0.14 (s, 6H); $^{13}$C NMR (126 MHz, CDCl$_3$) δ 140.1, 134.2, 114.4, 113.8, 74.9, 25.1, −1.7. HRMS (EI+) m/z calculated for [C$_{10}$H$_{18}$OSi]$^+$: 182.1127. found: 182.1137.

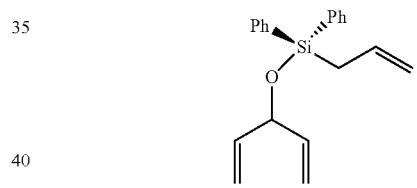

17

To a flame dried round bottom flask under argon was added diphenyldichlorosilane (0.421 mL, 2.0 mmol, 1.33 eq) and THF (10 mL). Imidazole (102 mg, 1.5 mmol, 1.0 eq) was then added, and the cloudy mixture was stirred for 5 minutes and then cooled to −78° C. 1,4-pentadien-3-ol (0.146 mL, 1.5 mmol, 1.0 eq) was then added, and the mixture was stirred for 15 min, warmed to 0° C. for 1 hr, and then stirred at ambient temperature for 1 hr. Allyl magnesium bromide (2 M in THF, 5 mL, 10 mmol) was then added dropwise. The clear yellow solution was stirred for 2.5 hr, and then quenched with saturated NH$_4$Cl (15 mL). The mixture was extracted with ethyl acetate (2×30 mL). The combined organic extracts were washed with brine (20 mL), dried with MgSO$_4$, and concentrated in vacuo. The product was isolated by column chromatography (0→3% ethyl acetate/hexanes) to give a 5:1 mixture of the desired product and the disilanol byproduct (347 mg, 61% corrected yield). Analytically pure material can be obtained by preparatory TLC (0.8% ethyl acetate/hexanes, run twice). $^1$H NMR (500 MHz, CDCl$_3$) δ 7.65-7.62 (m, 4H), 7.46-7.42 (m, 2H), 7.41-7.36 (m, 4H), 5.90-5.81 (m, 3H), 5.21 (dt, J=17.2, 1.5 Hz, 2H), 5.09 (dt, J=10.3, 1.4 Hz, 2H), 4.96 (ddt, J=17.0, 2.1, 1.5 Hz, 1H), 4.91 (ddt, J=10.1, 2.1, 1.1 Hz, 1H), 4.73 (tp, J=5.7, 1.4 Hz, 1H), 2.23 (dt, J=7.9, 1.3 Hz, 2H); $^{13}$C NMR (126 MHz, CDCl$_3$) δ 139.7, 135.1, 134.9, 133.2, 130.0, 127.8, 115.3, 114.7, 75.7, 22.6. HRMS (EI+) m/z calculated for $[C_{20}H_{22}OSi]^+$: 306.1440. found: 306.1452.

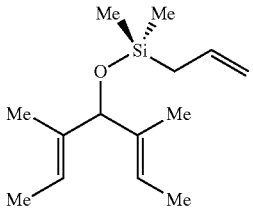

19

Compound 19 was synthesized according to a literature procedure (see Funk, T. W.; Berlin, J. M.; Grubbs, R. H. *J. Am. Chem. Soc.* 2006, 128, 1840).

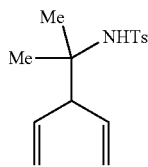

S2

A procedure adapted from Gomez, et al. (see Bosque, I.; Bagdatli, E.; Foubelo, F.; Gonzalez-Gomez, J. C. *J. Org. Chem.* 2014, 79, 1796) was followed. Bromo diene was synthesized by dropwise addition of 1,4-pentadien-3-ol (0.97 mL, 10 mmol) to a solution of $PBr_3$ (0.38 mL, 4 mmol) in 5 mL ether at 0° C. Upon complete conversion of the alcohol, as determined by TLC, the reaction was quenched with brine. The organic layer was separated, washed with saturated $NaHCO_3$ solution, dried over $MgSO_4$, filtered and carefully concentrated at 23° C. under a stream of Ar.

Toluenesulfonamide (0.58 g, 3.4 mmol), Indium powder (0.49 g, 4.2 mmol, 1.25 equiv), titanium (IV) ethoxide (1.78 mL, 8.48 mmol, 2.5 equiv), and acetone (0.27 mL, 3.7 mmol, 1.1 equiv) were dissolved in 20 mL THF and the mixture was stirred at 65° C. for 14 h. The bromide prepared above (1.04 g crude weight) was added directly to the reaction and heated at 65° C. for an addition 8 h. After cooling to 23° C., the reaction mixture was added to a 4:1 EtOAc/brine mixture and filtered through Celite. The crude residue was concentrated and subjected to flash chromatography to afford 0.42 g S2 (1.50 mmol, 44% yield with respect to toluenesulfonamide).

$^1$H NMR (500 MHz, CDCl$_3$) δ 7.78-7.73 (m, 2H), 7.30-7.26 (m, 2H), 5.77 (ddd, J=17.1, 10.3, 8.5 Hz, 2H), 5.20 (ddd, J=10.3, 1.7, 0.7 Hz, 2H), 5.17 (dd, J=1.7, 1.0 Hz, 1H), 5.13 (dd, J=1.7, 1.0 Hz, 1H), 4.58 (s, 1H), 2.85 (tt, J=8.5, 0.9 Hz, 1H), 2.42 (s, 3H), 1.16 (s, 6H). $^{13}$C NMR (125 MHz, CDCl$_3$) δ 143.00, 140.84, 135.85, 129.58, 127.17, 118.94, 59.48, 58.25, 25.06, 21.64. HRMS (FAB+) calculated for $C_{15}H_{22}SNO_2$ [M+H]: 280.1371. found 280.1370.

At 0° C., S2 (200 mg, 0.717 mmol) was added to a suspension of KH (31.6 mg, 0.788 mmol, 1.1 equiv) in 4 mL THF. After stirring for 1 h, allyl bromide (250 μL, 2.87 mmol, 4 equiv) and HMPA (4 mL) were added and the reaction was warmed to 23° C. After stirring for 24 h, the reaction was carefully quenched with water at 0° C. Excess water was added and the solution extracted with ether. The combined organic layers were washed with brine and dried over $MgSO_4$. Filtration and concentration afforded a crude residue, which was subjected to flash chromatography to afford 21 (107 mg, 0.335 mmol, 47% yield).

$^1$H NMR (500 MHz, CDCl$_3$) δ 7.76-7.71 (m, 2H), 7.25 (dt, J=8.0, 0.8 Hz, 2H), 5.91-5.77 (m, 3H), 5.15 (qd, J=1.9, 1.0 Hz, 2H), 5.12 (tt, J=1.9, 0.9 Hz, 3H), 5.09 (m, 1H), 5.07 (dq, J=10.2, 1.4 Hz, 1H), 4.02 (dt, J=6.1, 1.5 Hz, 2H), 3.66 (tt, J=7.7, 1.1 Hz, 1H), 2.40 (s, 3H), 1.32 (s, 6H). $^{13}$C NMR (125 MHz, CDCl$_3$) δ 142.74, 140.85, 137.62, 137.09, 129.41, 127.51, 117.86, 116.64, 65.35, 56.64, 49.58, 25.58, 21.56. HRMS (FAB+) calculated for $C_{18}H_{26}NSO_2$ [M+H]: 320.1684. found 320.1679.

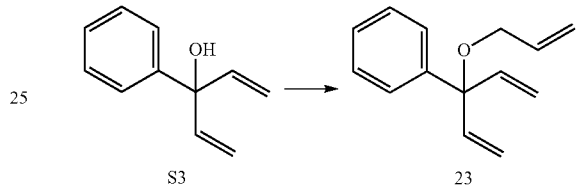

S3    23

Compound S3 was synthesized as previously reported (see Ndungu, J. M.; Larson, K. K.; Sarpong, R. *Org. Lett.* 2005, 7, 5845-5848). To a suspension of sodium hydride (60% dispersion, 0.125 g, 3.13 mmol, 2 equiv) in THF was added S3 (0.250 g, 1.56 mmol) as a solution in THF at 0° C. (total volume THF=10 mL). The reaction was stirred for 2 h, at which time allyl bromide (0.54 mL, 6.25 mmol, 4 equiv) was added dropwise. The reaction was warmed to room temperature and stirred for 16 h, at which time a conversion of about 30% was observed. The reaction was heated to 65° C. for 4 h, at which time complete conversion was observed. The reaction was cooled to room temperature, quenched with water, and diluted with ether. The organic layer was separated and washed with water and subsequently brine. The resultant organic layer was dried over $MgSO_4$, filtered, and concentrated to afford the crude product. Column chromatography afforded pure 23 (0.307 g, 1.53 mmol, 98% yield). $^1$H NMR (500 MHz, CDCl$_3$) δ 7.46-7.42 (m, 2H), 7.37-7.32 (m, 2H), 7.27 (tt, J=7.2, 1.3 Hz, 1H), 6.14 (dd, J=17.4, 10.8 Hz, 2H), 5.96 (ddt, J=17.2, 10.3, 5.0 Hz, 1H), 5.36 (dq, J=17.0, 2.0 Hz, 1H), 5.34 (dd, J=10.8, 1.4 Hz, 2H), 5.30 (dd, J=17.4, 1.4 Hz, 2H), 5.15 (dq, J=10.5, 1.7 Hz, 1H), 3.90 (dt, J=5.1, 1.7 Hz, 2H); $^{13}$C NMR (126 MHz, CDCl$_3$) δ 142.82, 140.18, 135.71, 128.23, 127.38, 127.33, 116.34, 115.60, 82.78, 64.95. HRMS (FAB+) calculated for $C_{14}H_{15}O$ [M+H—$H_2$]: 199.1123. found 199.1171.

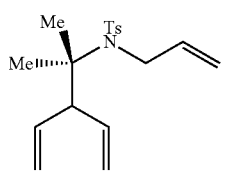

21

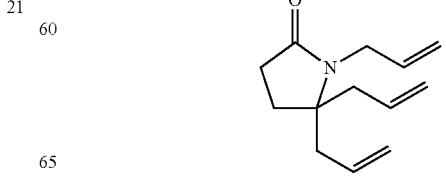

25

Compound 25 was synthesized according to a literature procedure (see Sattely, E. S.; Cortex, G. A.; Moebius, D. C.; Schrock, R. R.; Hoveyda, A. H. *J. Am. Chem. Soc.* 2005, 127, 8526-8533).

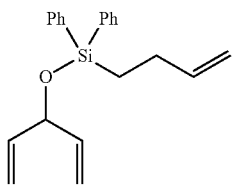

27

To a flame dried round bottom flask under argon was added diphenyldichlorosilane (0.421 mL, 2.0 mmol, 2.0 eq) and THF (10 mL). The solution was cooled to −78° C. and imidazole (68 mg, 1.0 mmol, 1.0 eq) was then added. The mixture was warmed to ambient temperature, stirred for 15 min, and then the cloudy mixture was cooled back to −78° C. 1,4-pentadien-3-ol (0.097 mL, 1.0 mmol, 1.0 eq) was added, and the mixture was stirred for 1 hr. Subsequently the mixture was warmed to ambient temperature and stirred for 2 hr. Meanwhile, to a flame dried 2-neck round bottom flask under argon was added magnesium turnings (204 mg, 8.4 mmol) and a small crystal of $I_2$ (5 mg). The flask was heated with a heat gun until a pink glow was observed, and then allowed to cool to ambient temperature. THF (10 mL) was then added, and a reflux condenser was attached. 4-bromobut-1-ene (0.812 mL, 8.0 mmol) was added, and the mixture began to heat spontaneously. The reaction achieved reflux without external heat for 15 minutes, at which point the magnesium was mostly consumed. The reaction was allowed to cool to room temperature. The Grignard solution was then added dropwise to the flask containing the silane in a 0° C. ice bath. The clear yellow solution was stirred for 2 hr, and then quenched with saturated $NH_4Cl$ (15 mL). The mixture was extracted with diethyl ether (2×30 mL). The combined organic extracts were washed with brine (20 mL), dried with $MgSO_4$, and concentrated in vacuo. The product was isolated by column chromatography (1-4% ethyl acetate/hexanes) to give a clear oil (207 mg, 65%) containing a trace impurity of the bis(homoallyl)silane byproduct. Analytically pure material can be obtained by preparatory TLC (1.5% ethyl acetate/hexanes, run twice).

$^1$H NMR (500 MHz, CDCl$_3$) δ 7.62-7.59 (m, 4H), 7.44-7.40 (m, 2H), 7.39-7.35 (m, 4H), 5.89 (ddt, J=17.1, 10.2, 6.2 Hz, 1H), 5.83 (ddd, J=17.1, 10.3, 5.8 Hz, 2H), 5.18 (dt, J=17.2, 1.5 Hz, 2H), 5.06 (dt, J=10.3, 1.4 Hz, 2H), 4.99 (dq, J=17.1, 1.7 Hz, 2H), 4.89 (ddt, J=10.1, 1.9, 1.4 Hz, 2H), 4.67 (tp, J=5.7, 1.4 Hz, 2H), 2.16 (dddd, J=12.3, 6.1, 3.1, 1.5 Hz, 2H), 1.30-1.25 (m, 2H); $^{13}$C NMR (126 MHz, CDCl$_3$) δ 141.3, 139.8, 135.3, 135.0, 130.0, 127.9, 114.7, 113.0, 75.6, 27.2, 13.8. HRMS (EI+) m/z calculated for $[C_{21}H_{24}OSi]^+$: 320.1596. found: 320.1608.

General Procedure for ARCM

In a glovebox, triene 13 (27.7 mg, 0.1 mmol) was dissolved in 35 μL, THF. To this solution was added 165 μL, of a stock solution (0.03 M in THF) of catalyst 5. The reaction vial was capped and stirred for 24 h and then quenched with an excess of ethyl vinyl ether outside of the glovebox. The reaction mixture was concentrated and conversion was determined by 500 MHz $^1$H NMR. The crude was subjected to flash chromatography or preparative TLC to afford the desired ARCM product (14, 22.6 mg, 95% yield, 54% ee). Pure products were submitted to analytical SFC to determine ee.

Characterization Data for ARCM Products

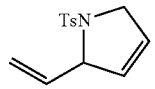

14

95% yield $[\alpha]_D^{25}$=+113° (c=1.09, CHCl$_3$); $^1$H NMR (500 MHz, CDCl$_3$) δ 7.71 (d, J=8.2 Hz, 2H), 7.31-7.28 (m, 2H), 5.79 (ddd, J=17.1, 10.1, 7.0 Hz, 1H), 5.67 (dq, J=6.1, 2.0 Hz, 1H), 5.53 (dq, J=6.3, 2.2 Hz, 1H), 5.28 (dt, J=17.1, 1.1 Hz, 1H), 5.13 (dt, J=10.1, 1.1 Hz, 1H), 4.92-4.87 (m, 1H), 4.17-4.14 (m, 2H), 2.42 (s, 3H); $^{13}$C NMR (126 MHz, CDCl$_3$) δ 143.5, 137.7, 135.6, 129.8, 129.2, 127.6, 125.3, 116.3, 69.1, 55.4, 21.6. HRMS (FAB+) m/z calculated for $[C_{13}H_{15}NSO_2+H]^+$: 250.0902. found: 250.0901.

Separation conditions: AD-H, 10% IPA, 2.5 mL/min, 54% ee

Determination of Absolute Configuration:

A racemic sample was synthesized according to the general procedure using triene 13 (83.1 mg, 0.3 mmol, 1.0 eq), rac-5 (0.375 μL, 0.04M in THF, 0.015 mmol, 0.05 eq) and THF (225 μL). Racemic 14 was isolated by column chromatography (10-20% Ethyl acetate/hexanes) to give a crystalline white solid (64 mg, 86%). This material was resolved by chiral prep-HPLC (Chiral Technologies AD-H SFC column, 21×250 mm, 5 μm particle, 20% IPA/Hexanes, 10 ml/min, 30 injections of 1 μg in 50 μL IPA, retention time=18 min, 20 min). The combined fractions of the faster eluting enantiomer (F1) were concentrated to afford a >99% ee sample (15 mg), which was then re-purified by preparative TLC (20% Ethyl acetate/hexanes) to remove a faint yellow color. A single crystal suitable for X-ray diffraction was grown by slow diffusion of pentane into a solution of F1 in diethyl ether. X-ray crystallographic analysis indicated that the absolute configuration of F1 is (S). The Flack and van Hooft parameters were 0.026 (7) and 0.021 (7) respectively.

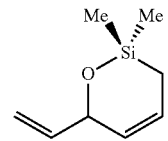

16

Due to volatility of the product, the yield was determined by NMR.

In a glovebox, 167 μL of a stock solution of catalyst 5 (0.03M in THF) was concentrated. A solution of triene 15 in 200 μL ds-THF was then added, and the capped vial was stirred at room temperature for 24 hr. Mesitylene (0.1 mmol, 13.9 μL, 1 equiv) was then added as an internal standard, and the mixture was diluted to 700 μL with ds-THF. The yield of product 16 was then determined by integration of the $^1$H NMR spectrum to be 65%. $^1$H NMR (500 MHz, THF-d$_8$) δ 5.88-5.82 (m, 2H), 5.57 (ddt, J=10.8, 2.9, 2.0 Hz, 1H), 5.20 (dt, J=17.0, 1.8 Hz, 1H), 4.98 (dt, J=10.3, 1.8 Hz, 1H), 4.87-4.81 (m, 1H), 1.26 (dt, J=4.9, 2.4 Hz, 1H), 1.23 (ddd, J=5.6, 2.9, 1.8 Hz, 1H), 0.16 (d, J=5.2 Hz, 6H). $^{13}$C NMR (126 MHz, THF-d$_8$) δ 141.3, 132.2, 124.6, 113.1, 74.4, 12.8, 0.5, −0.5.

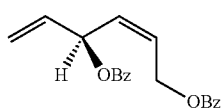

5

Product 16 was converted to the derivative shown above by treatment with Tamao-Fleming conditions and subsequent standard benzoylation conditions to afford a product amenable to ee determination.

$[\alpha]_D^{25}=-6.6°$ (c=0.07, CHCl$_3$); $^1$H NMR (500 MHz, CDCl$_3$) δ 8.09-8.01 (m, 4H), 7.59-7.51 (m, 2H), 7.50-7.39 (m, 4H), 6.31 (ddq, J=8.2, 5.6, 1.4 Hz, 1H), 6.00 (ddd, J=17.3, 10.5, 5.5 Hz, 1H), 5.94 (dtd, J=11.1, 6.6, 1.1 Hz, 1H), 5.77 (ddt, J=11.0, 8.7, 1.5 Hz, 1H), 5.44 (dt, J=17.2, 1.3 Hz, 1H), 5.29 (dt, J=10.5, 1.2 Hz, 1H), 5.11 (ddd, J=13.4, 6.5, 1.6 Hz, 1H), 5.04 (ddd, J=13.3, 6.7, 1.4 Hz, 1H). HRMS (MM) m/z calculated for [C$_{13}$H$_{13}$O$_2$]$^+$ (M-OBz): 201.0916. found: 201.0905. Separation conditions: OJ-H, 5% IPA, 2.5 mL/min. 69% ee.

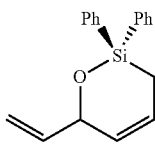

18

29% yield $[\alpha]_D^{25}=-66.3°$ (c=0.37, CHCl$_3$); $^1$H NMR (500 MHz, CDCl$_3$) δ 7.65-7.60 (m, 4H), 7.45-7.35 (m, 6H), 6.03 (dddd, J=10.6, 5.9, 4.6, 2.0 Hz, 1H), 5.94 (ddd, J=17.0, 10.2, 5.9 Hz, 1H), 5.68 (dddd, J=10.8, 3.0, 2.2, 1.6 Hz, 1H), 5.32 (dt, J=17.0, 1.5 Hz, 1H), 5.10 (dt, J=10.2, 1.5 Hz, 1H), 5.10-5.06 (m, 1H), 1.82-1.78 (m, 2H); $^{13}$C NMR (126 MHz, CDCl$_3$) δ 139.6, 135.8, 135.7, 134.6, 134.5, 131.8, 130.2, 130.2, 128.1, 128.0, 124.1, 114.2, 74.4, 10.3.

HRMS (FAB+) m/z calculated for [C$_{18}$H$_{17}$OSi]$^+$ (M+H$^+$—H$_2$): 277.1049. found: 277.1054.

Separation conditions: AD-H, 7% IPA, 2.5 mL/min. 67% ee

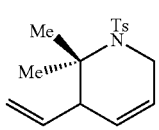

22

90% yield $[\alpha]_D^{25}=-107°$ (c=0.92, CHCl$_3$); $^1$H NMR (500 MHz, CDCl$_3$) δ 7.72 (d, J=8.2 Hz, 2H), 7.28 (d, J=8.0 Hz, 2H), 5.77-5.71 (m, 1H), 5.62 (dt, J=17.2, 9.6 Hz, 1H), 5.58-5.52 (m, 1H), 5.06-5.03 (m, 1H), 5.03-4.99 (m, 1H), 4.17 (dd, J=18.0, 2.7 Hz, 1H), 4.12-4.03 (m, 1H), 2.53 (ddd, J=8.9, 4.2, 2.1 Hz, 1H), 2.43 (s, 3H), 1.24 (s, 3H), 1.21 (s, 2H). $^{13}$C NMR (125 MHz, CDCl$_3$) δ 143.03, 140.18, 137.30, 129.58, 127.59, 127.24, 122.95, 117.23, 58.46, 52.73, 44.73, 24.86, 24.53, 21.63. HRMS (FAB+) calculated for C$_{16}$H$_{22}$NO$_2$S [M+H]: 292.1371. found 292.1366.

Separation conditions: OJ-H, 5% IPA, 2.5 mL/min. 57% ee

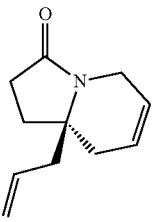

26

72% yield. Spectral characterization of 26 matches a previous report of its synthesis; the sign of the optical rotation indicates that the enantiomer is formed in preference (Sattely, E. S.; Cortex, G. A.; Moebius, D. C.; Schrock, R. R.; Hoveyda, A. H. J. Am. Chem. Soc. 2005, 127, 8526-8533. Lit. $[\alpha]_D^{25}=+57.7°$ (88% ee, c=1, CHCl$_3$); $[\alpha]_D^{25}=28.4°$ (47% ee, c=1.27, CHCl$_3$).

Separation conditions: AD-H, 10% IPA, 2.5 mL/min. 47% ee

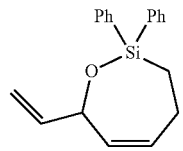

28

Following the general procedure for ARCM (capped vial), diene 28 was isolated in 61% yield, 0% ee. In order to prevent reversibility caused by the presence of ethylene, the procedure was modified:

In a glovebox, triene 27 (15 mg, 0.047 mmol, 1 equiv) was dissolved in 67 μL THF. To this solution was added 33 μL of a stock solution (0.03 M in THF) of catalyst 5. The reaction vial was left uncapped and stirred for 24 h. The reaction was then diluted with 500 μL ether and quenched with an excess of ethyl vinyl ether outside of the glovebox. The mixture was purified as above to yield the desired product (28, 7.0 mg, 51% yield, 37% ee).

$[\alpha]_D^{25}=+23°$ (c=0.51, CHCl$_3$); $^1$H NMR (500 MHz, CDCl$_3$) δ 7.67-7.57 (m, 4H), 7.45-7.32 (m, 6H), 6.02 (ddd, J=17.1, 10.3, 5.2 Hz, 1H), 5.96 (dtd, J=11.3, 6.9, 2.1 Hz, 1H), 5.66 (ddt, J=11.3, 4.9, 1.2 Hz, 1H), 5.41 (dt, J=16.9, 1.6 Hz, 1H), 5.15 (dt, J=10.2, 1.7 Hz, 1H), 5.16-5.12 (m, 1H), 2.52 (qt, J=6.6, 1.1 Hz, 2H), 1.55-1.48 (m, 1H), 1.31 (ddd, J=15.0, 7.3, 5.7 Hz, 1H); $^{13}$C NMR (126 MHz, CDCl$_3$) δ 140.1, 136.4, 135.8, 134.6, 134.4, 134.1, 133.1, 130.0, 129.9, 128.2, 127.9, 114.0, 71.2, 22.2, 12.5. HRMS (EI+) m/z calculated for [C$_{19}$H$_{20}$OSi]+: 292.1284. found: 292.1286.

Separation conditions: AD-H, 2% IPA, 2.5 mL/min, 37% ee.

Tentative Model for ARCM Enantioinduction

Based on previous computational studies of terminal olefin homodimerization with catalyst rac-5, (see Liu, P.; Xu, X.; Dong, X.; Keitz, B. K.; Herbert, M. B.; Grubbs, R. H.; Houk, K. N. J. Am. Chem. Soc. 2012, 134, 1464-1467) and without being bound by theory, we propose a side-bound ruthenacyclobutane mechanism is likely. The non-reacting vinyl group is located on a pseudo-equatorial position of an envelope-type conformation in S4. Isomerization of the ruthenacyclobutane leads to S5, followed by retro-[2+2] to release the product.

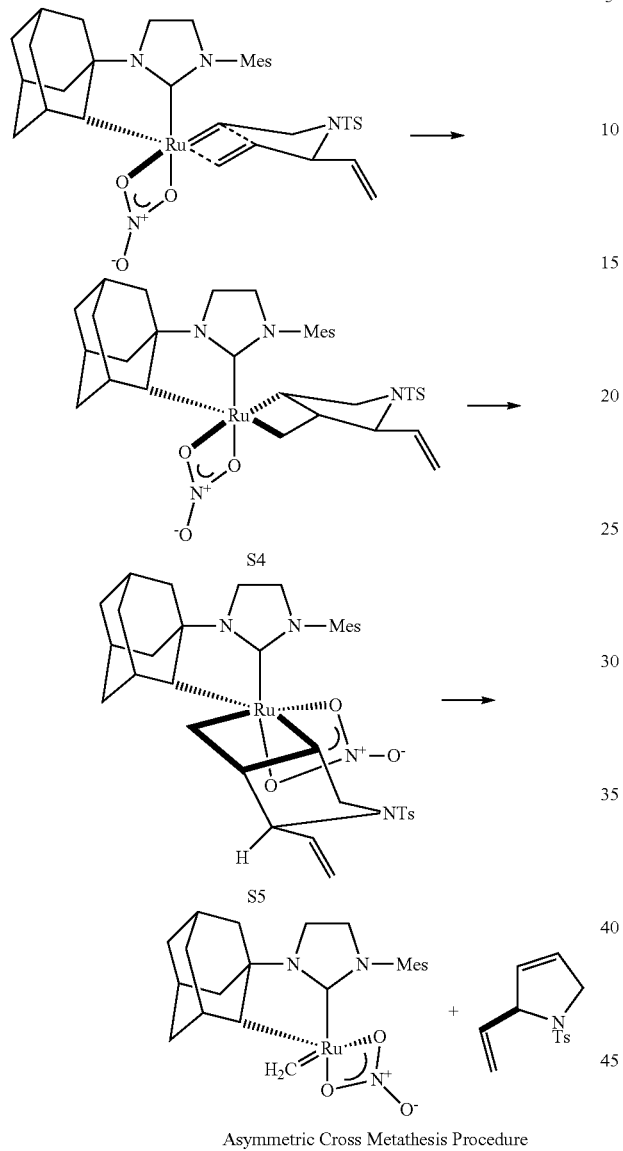

Asymmetric Cross Metathesis Procedure

In a glovebox, TBS-protected alcohol 29 (20 mg, 0.1 mmol) and cis-1,4-diacetoxy-2-butene (86 mg, 0.5 mmol) were added to a glass vial and the mixture dissolved in 0.3 mL THF. Catalyst 5 was added to the mixture as a stock solution (5 mol %, 0.005 mmol, 165 µL of a 0.03 M solution) and the reaction heated to 35° C. for 18 h while uncapped. The reaction was removed from the glovebox, quenched with ethyl vinyl ether, and concentrated. Flash chromatography afforded 9.5 mg (0.035 mmol, 35% yield, 93% Z). TBS deprotection and acylation with (S)-MTPA-C$_1$ enabled determination of ee (50%) and absolute configuration (R).

$^1$H NMR (500 MHz, CDCl$_3$) δ 5.78 (ddd, J=17.2, 10.3, 5.1 Hz, 1H), 5.61-5.48 (m, 2H), 5.23 (dt, J=17.1, 1.6 Hz, 1H), 5.06 (dt, J=10.3, 1.6 Hz, 1H), 4.93 (ddt, J=6.7, 5.1, 1.5 Hz, 1H), 4.73-4.66 (m, 1H), 4.64-4.58 (m, 1H), 2.06 (s, 3H), 0.89 (s, 8H), 0.07 (s, 3H), 0.06 (s, 3H); $^{13}$C NMR (126 MHz, CDCl$_3$) δ 139.72, 136.75, 123.25, 114.00, 70.23, 60.54, 25.98, 20.99, 18.41, −4.55.

Synthesis of NHC Ligands

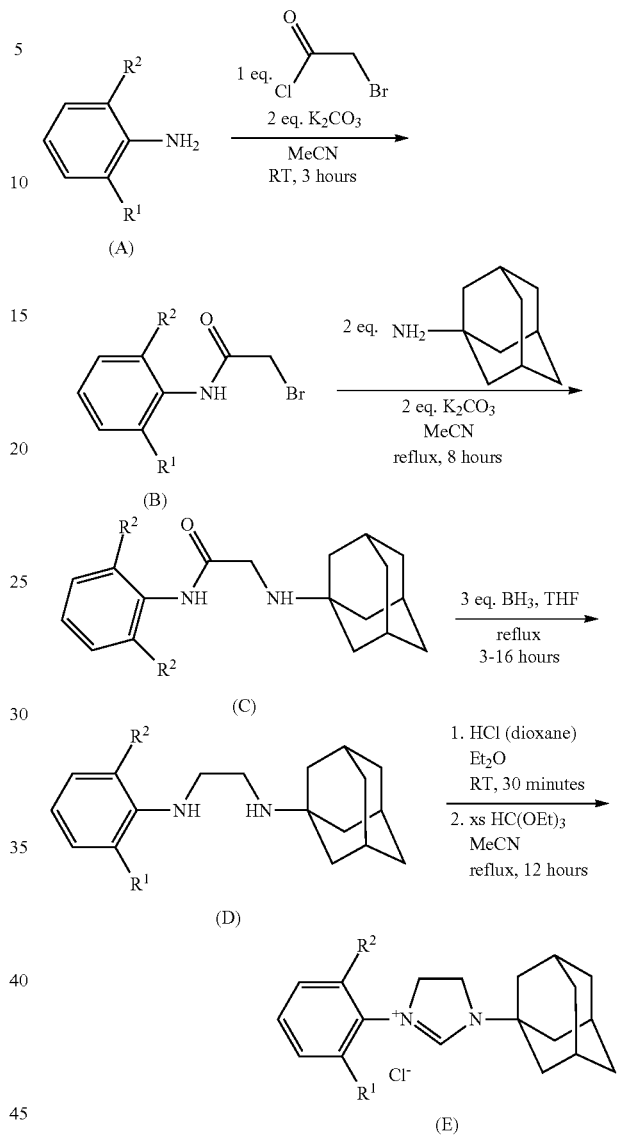

The ligands of the invention were synthesized according to following general procedures. Data is shown for the intermediates, wherein R$^1$ and R$^2$ are OMe.

General Procedure for Intermediates (A)

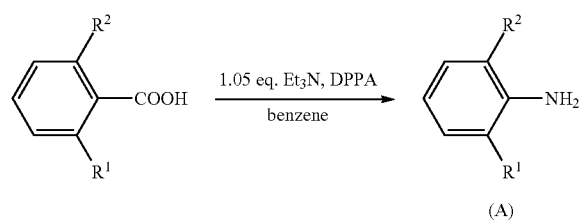

To a solution of the carboxylic acid (19.2 mmol, 1 equiv.) in benzene (60 mL, 0.3 M) was added Et$_3$N (20.2 mmol, 1.05 equiv.) and DPPA (20.2 mmol, 1.05 equiv.). The reaction mixture was then heated to reflux for 12 h. and subsequently cooled to r.t. The solution was poured into a mixture of NaOH (2M, 40 mL/1 g of RCOOH) and THF (40 mL/1 g of RCOOH) with stirring. The organic layer was separated and the aqueous layer extracted with EtOAc (3×50 mL). The combined organic layer was washed with brine, dried over $Na_2SO_4$ and concentrated in vacuo. The resultant residue was redissolved in EtOAc, filtered, concentrated in vacuo and purified by flash chromatography on silica gel to give aniline (A).

General Procedure for Intermediates (B)

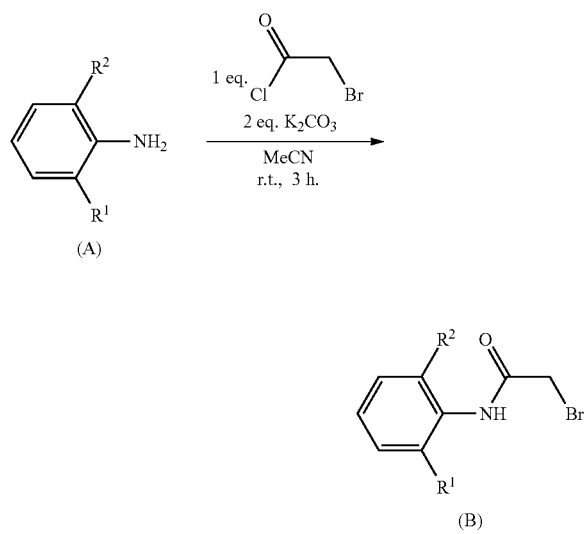

General Procedure for Intermediates (C)

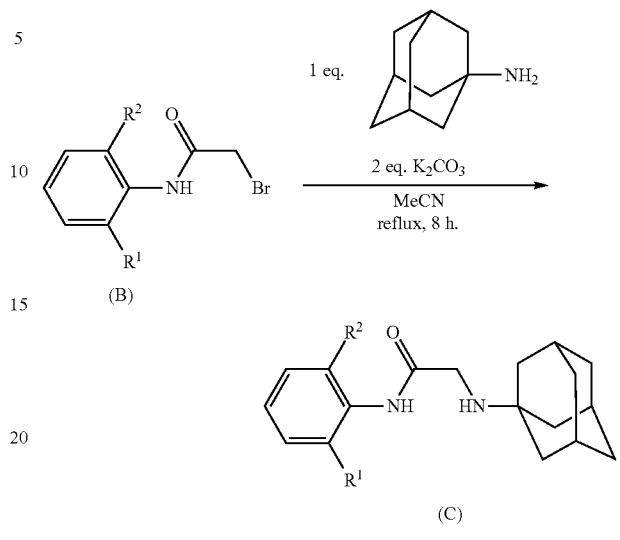

Anhydrous $K_2CO_3$ (32.8 mmol, 2 equiv.) was added to a solution of the aniline (A) (16.4 mmol, 1 equiv.) in MeCN (200 mL, 0.08 M). Bromoacetyl chloride (16.4 mmol, 1 equiv.) was then added dropwise and the reaction mixture allowed to stir at 20° C. for 3 h. The mixture was filtered, concentrated under reduced pressure and the resultant residue purified by recrystallization or flash chromatography on silica gel to give intermediate amino bromide (B).

Compound

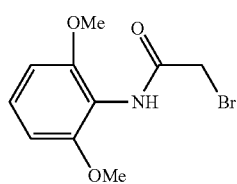 [SMILES: COc1cccc(OC)c1NC(=O)CBr]

was synthesized following the general procedure for intermediates (B), using the corresponding starting materials and reagents.

$^1$H NMR (400 MHz, $CDCl_3$) δ 7.56 (br s, 1H), 7.22 (t, J=8.4 Hz, 1H), 6.60 (d, J=8.4 Hz, 2H), 4.04 (s, 2H), 3.84 (s, 6H) ppm.

$^{13}$C NMR (101 MHz, $CDCl_3$) δ 163.9, 155.5, 128.5, 113.4, 104.4, 56.2, 29.5 ppm.

HRMS (FAB) calcd. for $C_{10}H_{13}BrNO_3$ [M+H]$^+$ 274.0079. found 274.0073.

Anhydrous $K_2CO_3$ (19.7 mmol, 2 equiv.) was added to a solution of the amido bromide (B) (9.8 mmol, 1 equiv.) in MeCN (200 mL, 0.05 M). 1-adamantylamine (14.8 mmol, 2.5 equiv.) was added to the reaction mixture, which was then heated at reflux for 12 h. The mixture was then filtered, concentrated and the resultant residue was purified by flash chromatography on silica gel.

Alternative Procedure

Anhydrous $K_2CO_3$ (19.7 mmol, 2 equiv.) was added to a solution of the amido bromide (9.8 mmol, 1 equiv.) in MeCN (200 mL, 0.05 M). 1-adamantylamine (14.8 mmol, 2 equiv.) was added to the reaction mixture, which was then heated at reflux for 8 h. The mixture was then filtered, concentrated and the resultant residue was purified by flash chromatography on silica gel.

Compound

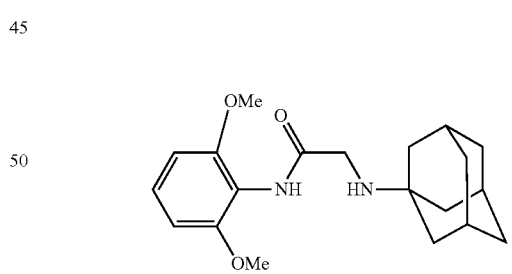

was synthesized following the general procedure for intermediates (C), using the corresponding starting materials and reagents.

$^1$H NMR (400 MHz, $CDCl_3$) δ 8.82 (br s, 1H), 7.16 (t, J=8.4 Hz, 1H), 6.59 (d, J=8.4 Hz, 2H), 3.82 (s, 6H), 3.41 (s, 2H), 2.09 (s, 3H), 1.80-1.48 (m, 13H) ppm.

$^{13}$C NMR (101 MHz, $CDCl_3$) δ 172.1, 155.7, 127.5, 114.6, 104.6, 56.2, 51.2, 44.7, 42.8, 36.8, 29.7 ppm.

HRMS (FAB) calcd. for $C_{20}H_{29}N_2O_3$ [M+H]$^+$ 345.2180. found 345.2178.

General Procedure for Intermediates (D)

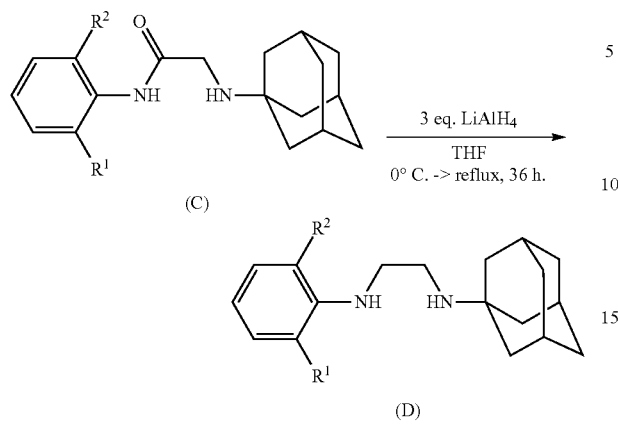

THF (100 mL, 0.2 M) was added to a flame-dried, two-neck flask under an atmosphere of argon and cooled to 0° C. LiAlH$_4$ (51.5 mmol, 3 equiv.) was added portionwise with stirring. The amido amine (C) (17.2 mmol, 1 equiv.) was dissolved in THF (20 mL) and added to the reaction mixture dropwise. The reaction was then warmed to reflux for 36 h. before cooling to room temperature. H$_2$O (2 mL), 15 w/w % NaOH (2 mL) and H$_2$O (6 mL) were added slowly sequentially to the reaction mixture. THF was removed in vacuo and the residue partitioned between EtOAc (125 mL) and H$_2$O (50 mL). The aqueous layer was extracted with EtOAc (2×50 mL) and the combined organic layers were washed with H$_2$O (100 mL), dried over Na$_2$SO$_4$, filtered and concentrated in vacuo.

Alternative Procedure

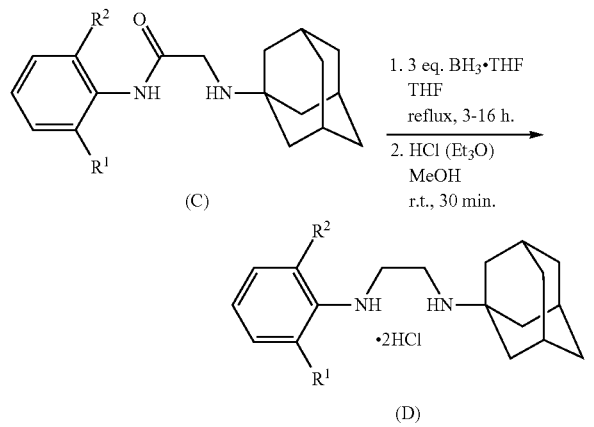

Amido amine (2.9 mmol, 1 equiv.) was added to a flame-dried, heavy-walled Schlenk flask under an atmosphere of argon. BH$_3$.THF in THF (1.0 M, 8.7 mmol, 3 equiv.) was then added slowly. When gas evolution had ceased, the Schlenk flask was sealed and heated to reflux for 8 h. The reaction mixture was then cooled to r.t. and MeOH (20 mL) was added slowly and then removed in vacuo. A further portion of MeOH (40 mL) was added and then removed in vacuo. The resulting residue was then dissolved in MeOH (40 mL) and HCl in Et$_2$O (2.0 M, 14.5 mmol, 5 equiv.) was added and stirred at 20° C. for 30 min. The reaction mixture was then concentrated in vacuo and the resultant solid triturated with Et$_2$O (40 mL), filtered, washed with Et$_2$O (3×20 mL) and dried in vacuo.

Compound 5

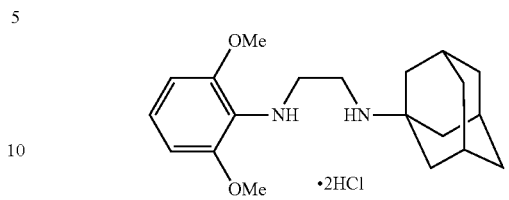

was synthesized following the general procedure for intermediates (D), using the corresponding starting materials and reagents.

$^1$H NMR (400 MHz, CD$_3$OD) δ 7.49 (t, J=8.5 Hz, 1H), 6.90 (d, J=8.5 Hz, 2H), 4.01 (s, 6H), 3.70 (t, J=7.0 Hz, 2H), 3.37 (t, J=7.0 Hz, 2H), 2.23 (s, 3H), 1.99 (s, 3H), 1.99 (s, 3H), 1.78 (app q, J=12.5 Hz, 6H) ppm.

$^{13}$C NMR (101 MHz, CD$_3$OD) δ 154.7, 132.9, 112.8, 106.3, 59.6, 57.4, 47.2, 39.4, 36.6, 36.4, 30.6 ppm.

HRMS (FAB) calcd. for C$_{20}$H$_{31}$N$_2$O$_2$ [M–H]$^+$331.2375. found 331.2386.

General Procedure for Intermediates (E)

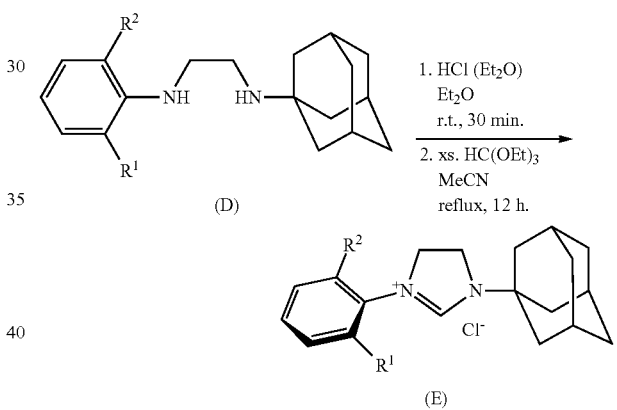

To a solution of diamine (2.0 mmol, 1 equiv.) in Et$_2$O (10 mL) was added HCl in Et$_2$O (2.0 M, 4.0 mmol, 2 equiv.) and the reaction mixture was stirred at 20° C. for 30 min. The resultant precipitate was filtered, washed with Et$_2$O (2×20 mL) and dried in vacuo. To the resultant solid was added HC(OEt)$_3$ (30 mmol, 15 equiv.) and MeCN (v/v with HC(OEt)$_3$). The reaction mixture was heated to reflux for 12 h. and subsequently cooled to r.t. MeCN was removed in vacuo and the resulting residue triturated with Et$_2$O (20 mL). The Et$_2$O was decanted and the resulting solid triturated with two further portions of Et$_2$O (2×20 mL). The product was dried in vacuo at 35° C.

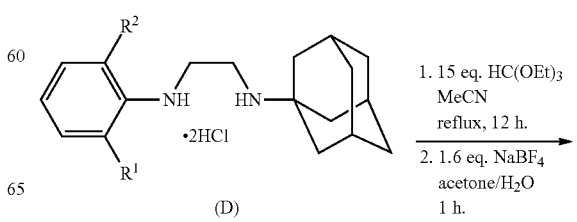

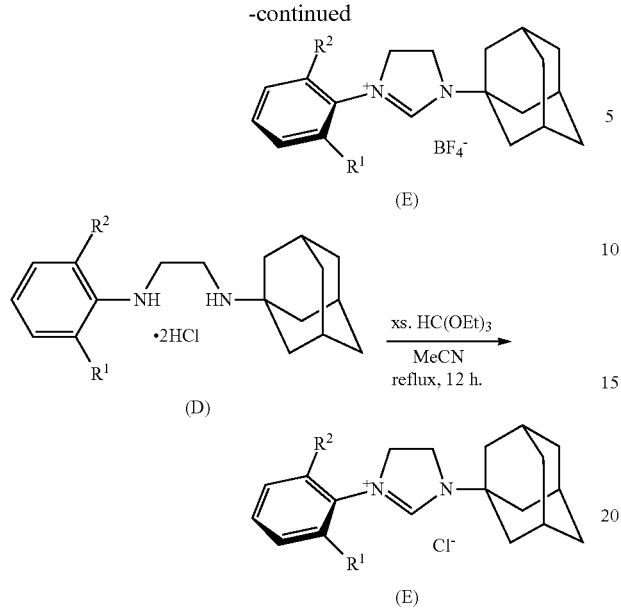

To the diamine dihydrochloride salt (1.3 mmol, 1 equiv.) was added HC(OEt)$_3$ (19.5 mmol, 15 equiv.) and MeCN (v/v with HC(OEt)$_3$). The reaction mixture was heated to reflux for 12 h. and subsequently cooled to r.t. MeCN was removed in vacuo and the resulting residue triturated with Et$_2$O (20 mL). The Et$_2$O was decanted and the resulting solid triturated with two further portions of Et$_2$O (2×20 mL). The product was dried in vacuo at 35° C.

Alternative Procedure

To the diamine dihydrochloride salt (1.1 mmol, 1 equiv.) was added HC(OEt)$_3$ (15.8 mmol, 15 equiv.) and MeCN (2 equiv. v/v with HC(OEt)$_3$). The reaction mixture was heated to reflux for 12 h. and subsequently cooled to r.t. MeCN was removed in vacuo and the resulting residue triturated with Et$_2$O (20 mL). The Et$_2$O was decanted and the resulting solid triturated with two further portions of Et$_2$O (2×20 mL). To the resulting solid was added 2:1 acetone:H$_2$O (6 mL) and NaBF$_4$ (1.7 mmol, 1.6 equiv.) and the reaction mixture was stirred at 25° C. for 1 hour. The acetone was then removed in vacuo and the product extracted with DCM (2×15 mL), dried over Na$_2$SO$_4$, filtered, concentrated and dried in vacuo at 35° C.

Compound

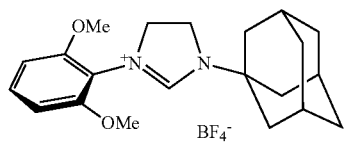

was synthesized following the general procedure for intermediates (E), using the corresponding starting materials and reagents.

$^1$H NMR (400 MHz, CDCl$_3$) δ 7.90 (s, 1H), 7.30 (t, J=8.5 Hz, 1H), 6.62 (d, J=8.5 Hz, 2H), 4.40-4.18 (m, 4H), 3.89 (s, 6H), 2.26 (s, 3H), 2.01 (s, 3H), 2.00 (s, 3H), 1.80-1.67 (m, 6H) ppm.

$^{13}$C NMR (101 MHz, CDCl$_3$) δ 155.7, 155.3, 130.8, 113.3, 104.7, 57.9, 56.6, 50.4, 44.9, 41.1, 35.6, 29.3 ppm.

HRMS (FAB) calcd. for C$_{21}$H$_{29}$N$_2$O$_2$ [M$^+$] 341.2229. found 341.2231.

Synthesis of Ruthenium Catalysts

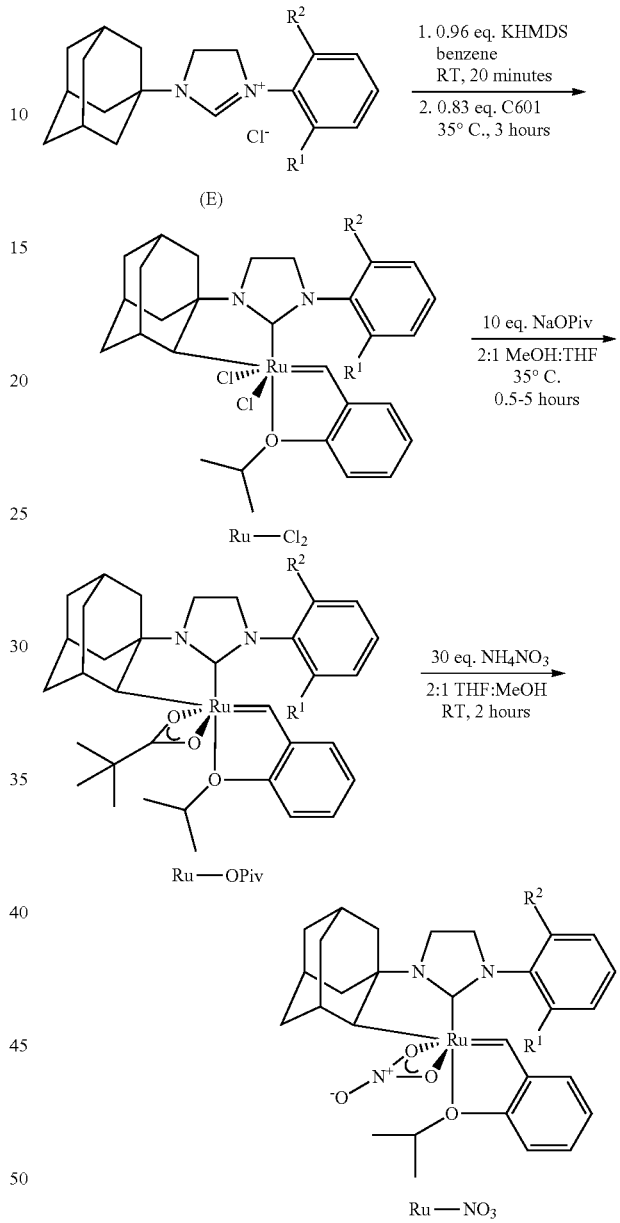

General Procedure for Ru—Cl$_2$

In a nitrogen-filled glovebox, intermediate (E) (1.15 mmol, 1.0 equiv.) and KHMDS (1.11 mmol, 0.96 equiv.) were weighed into a vial, to which benzene (6 mL, 0.2 M) was added. The suspension was stirred at 20° C. for 15 mins, at which stage C601 (0.82 mmol, 0.71 equiv.) was added and the reaction stirred at 35° C. for 3 h. The solution was then removed from the glovebox and pentane (6 mL, v/v with benzene) was added. The resultant green precipitate was filtered and washed with pentane and then with 1:1 pentane:Et$_2$O until the washings were clear. The residue was purified by silica gel plug using DCM as eluant and the product concentrated in vacuo.

Alternative Procedure

Intermediate (E) (0.66 mmol, 1.0 equiv.) and KHMDS (0.63 mmol, 0.96 equiv.) were weighed into a vial, to which benzene (4 mL, 0.2 M) was added. The suspension was stirred at 20° C. for 15 mins, at which stage C601 (0.55 mmol, 0.83 equiv.) was added and the reaction stirred at 35° C. for 3 h. The solution was then removed from the glovebox and pentane (4 mL, v/v with benzene) was added. The green precipitate was filtered and washed with 1:1 pentane:Et$_2$O until the washings were colourless. The residue was purified by silica gel plug using DCM as eluant.

Alternative Procedure

Intermediate (E) (0.35 mmol, 1.0 equiv.) and LiHMDS (0.33 mmol, 0.96 equiv.) were weighed into a vial, to which benzene (4 mL, 0.1 M) was added. The suspension was stirred at 20° C. for 15 mins, at which stage C$_{601}$ (0.28 mmol, 0.83 equiv.) was added and the reaction stirred at 35° C. for 3 h. The solution was then removed from the glovebox and pentane (4 mL, v/v with benzene) was added. The green precipitate was filtered and washed with 1:1 pentane:Et$_2$O until the washings were colourless. The residue was purified by silica gel chromatography using DCM/MeOH as eluant.

Compound

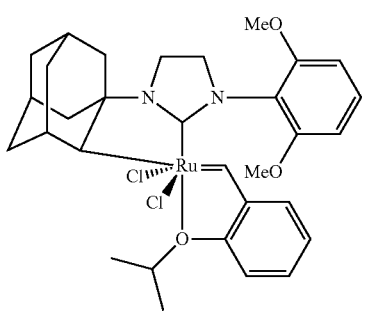

was synthesized following the general procedure for Hov-Cl$_2$, using the corresponding reagents.

$^1$H NMR (600 MHz, CDCl$_3$) δ 17.47 (s, 1H), 7.55 (ddd, J=8.6, 7.4, 1.7 Hz, 1H), 7.44 (t, J=8.4 Hz, 1H), 6.99 (dd, J=7.5, 1.6 Hz, 1H), 6.93 (d, J=8.4 Hz, 1H), 6.88 (t, J=7.4 Hz, 1H), 6.69 (d, J=8.4 Hz, 2H), 5.06 (hept, J=6.1 Hz, 1H), 4.06-3.95 (m, 2H), 3.92-3.84 (m, 2H), 3.70 (s, 6H), 2.96 (s, 6H), 2.40 (s, 3H), 1.94 (d, J=11.9 Hz, 3H), 1.82 (d, J=12.3 Hz, 3H), 1.63 (d, J=6.2 Hz, 6H) ppm.

$^{13}$C NMR (101 MHz, CDCl$_3$) δ 309.8 (d, J=43.5 Hz), 209.61, 158.66, 152.60, 145.61, 130.42, 129.42, 123.35, 122.87, 122.57, 113.41, 104.93, 74.12, 57.25, 56.60, 51.37, 44.80, 42.18, 36.30, 30.12, 22.58 ppm.

General Procedure for Ru-OPiv:

In a nitrogen-filled glovebox, to the Ru—Cl$_2$ (0.32 mmol, 1.0 equiv.) and NaOPiv (3.2 mmol, 10 equiv.) was added 2:1 MeOH:THF (10.5 mL, 0.03 M). The reaction mixture was stirred at 35° C. until the solution became purple in colour and no further colour change was noted after a 30 min interval. The solution was concentrated in vacuo and the resulting solids triturated with 2:1 pentane:Et$_2$O (10 mL), filtered and washed with 2:1 pentane:Et$_2$O until the washings were colourless. DCM was then added to elute the product, which was obtained after concentration in vacuo.

Ru-16 was synthesized following the general procedure for Ru-OPiv, using the corresponding reagents.

$^1$H NMR (600 MHz, C$_6$D$_6$) δ 15.30 (s, 1H), 7.54 (dd, J=7.4, 1.7 Hz, 1H), 7.30 (ddd, J=8.7, 7.4, 1.7 Hz, 1H), 6.99 (t, J=8.3 Hz, 1H), 6.97 (t, J=7.2 Hz, 1H), 6.73 (d, J=8.3 Hz, 1H), 6.29 (d, J=8.3 Hz, 1H), 6.23 (d, J=8.3 Hz, 1H), 4.83 (hept, J=6.3 Hz, 1H), 4.21 (q, J=9.9 Hz, 1H), 4.14 (s, 1H), 3.48 (q, J=9.3 Hz, 1H), 3.37 (s, 3H), 3.35 (s, 3H), 3.35-3.30 (m, 2H), 2.46 (br s, 1H), 2.12 (d, J=11.7 Hz, 1H), 2.06 (s, 1H), 1.89-1.80 (m, 2H), 1.73-1.67 (m, 2H), 1.60 (d, J=6.5 Hz, 3H), 1.53 (d, J=12.1 Hz, 1H), 1.51-1.43 (m, 2H), 1.29 (d, J=10.6 Hz, 1H), 1.21 (s, 9H), 1.20-1.16 (m, 1H), 1.15 (d, J=6.3 Hz, 3H), 0.73 (d, J=11.9 Hz, 1H).

$^{13}$C NMR (101 MHz, C$_6$D$_6$) δ 260.8 (d, J=10.6 Hz), 215.4, 158.0, 157.6, 154.4, 143.9, 127.6, 125.0, 123.1, 122.8, 120.3, 113.4, 105.0, 104.3, 74.3, 67.8, 62.8, 55.2, 55.0, 51.0, 42.7, 41.6, 40.7, 39.2, 38.3, 38.1, 37.5, 33.7, 31.1, 30.2, 28.1, 27.7, 21.7, 21.2 ppm General Procedure for Ru—NO$_3$:

In a nitrogen-filled glovebox, to the Ru-OPiv (0.053 mmol, 1.0 equiv.) and NH$_4$NO$_3$ (1.6 mmol, 30 equiv.) was added 2:1 THF:MeOH. The reaction mixture was stirred at 20° C. for 2 h. and then concentrated in vacuo. The resultant solids were triturated with 1:1 pentane:Et$_2$O (5 mL), filtered and washed with 1:1 pentane:Et$_2$O (2×5 mL). The product was obtained by elution of the solid with DCM and concentration of the resultant solution in vacuo.

Ru-20 was synthesized following the general procedure for Ru—NO$_3$, using the corresponding reagents.

$^1$H NMR (600 MHz, C$_6$D$_6$) δ 15.53 (s, 1H), 7.46 (d, J=7.4 Hz, 1H), 7.25-7.19 (m, 1H), 7.01 (t, J=8.4 Hz, 1H), 6.89 (t, J=7.4 Hz, 1H), 6.52 (d, J=8.4 Hz, 1H), 6.47 (d, J=8.4 Hz, 1H), 6.14 (d, J=8.4 Hz, 1H), 4.58 (hept, J=6.3 Hz, 1H), 4.19 (s, 1H), 3.99 (q, J=10.9 Hz, 1H), 3.67 (s, 3H), 3.64-3.56 (m, 1H), 3.42 (s, 3H), 3.31 (q, J=10.9 Hz, 1H), 3.26-3.20 (m, 1H), 2.28 (s, 1H), 2.03 (s, 1H), 2.00 (d, J=12.1 Hz, 1H), 1.86 (d, J=10.9 Hz, 1H), 1.77 (t, J=11.5 Hz, 2H), 1.66 (s, 1H), 1.50 (t, J=10.5 Hz, 2H), 1.46 (d, J=6.3 Hz, 3H), 1.41 (d, J=12.4 Hz, 1H), 1.17 (d, J=11.2 Hz, 1H), 1.12 (d, J=12.0 Hz, 1H), 0.94 (d, J=6.2 Hz, 3H), 0.61 (d, J=12.1 Hz, 1H) ppm.

$^{13}$C NMR (101 MHz, C$_6$D$_6$) δ 266.4 (d, J=7.9 Hz), 216.0, 159.2, 157.5, 154.8, 143.7, 129.1, 126.4, 123.2, 122.8, 118.7, 113.0, 104.5, 104.0, 74.0, 66.9, 63.2, 55.7, 55.1, 51.1, 42.6, 42.1, 40.4, 37.9, 37.9, 37.8, 33.6, 30.9, 30.0, 21.5, 20.4 ppm.

The C—H activated catalyst complexes of the invention were synthesized following the above procedures. Table 6 shows the $^1$H chemical shifts, expressed in ppm, for the diagnostic benzylidene proton for the Ru—Cl$_2$, Ru-OPiv and the Ru—NO$_3$ type catalysts. Sometimes it has been observed that catalysts with unsymmetrical aryl group exist as a mixture of conformers in solution.

TABLE 6

| R¹ | R² | Ru—Cl₂ δ (ppm) in CDCl₃ | Ru—OPiv δ (ppm) in C₆D₆ | Ru—NO₃ δ(ppm) in C₆D₆ |
|---|---|---|---|---|
| F | F | 17.25 | 15.10 | 15.39 |
| F | Me | 16.87 | 14.67, 15.24 (2:1 ratio) | 15.05, 15.55 (1:1.6 ratio) |
| F | CF₃ | 16.86 | 14.77, 15.04 (2.6:1 ratio) | 15.15, 15.37 (3.5:1) |
| F | iPr | 16.88 | 14.59 | 14.98 |
| Me | OMe | 17.00 | 14.86, 15.26 (1:2.4 ratio) | 15.17, 15.52 (2:1 ratio) |
| F | OMe | 17.35 | 15.07, 15.30 (3.4:1 ratio) | 15.38, 15.51 (6.8:1 ratio) |
| OMe | OMe | 17.47 | 15.30 | 15.53 |

Homodimerization of Allylbenzene

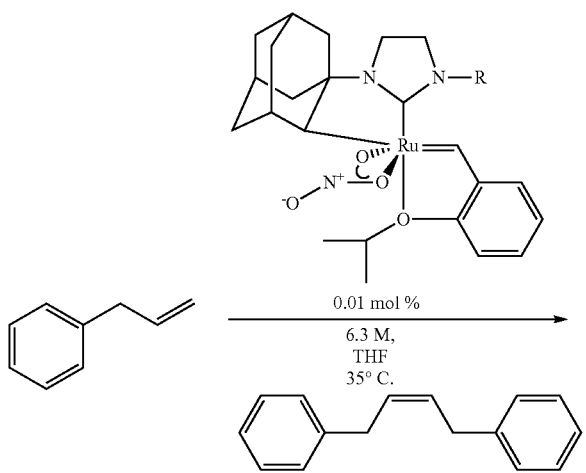

Typical procedure: homodimerization of allylbenzene at 0.01 mol % catalyst loadings In a nitrogen-filled glovebox, allylbenzene (200 µL, 1.51 mmol, 1 equiv.) and tridecane (20 µL) were combined in a 4 mL vial, to which a solution of the appropriate catalyst (0.15 µmol, 0.01 mol %) in THF (20 µL) was added. The reaction was stirred open to the atmosphere at 35° C. Samples for GC analysis were obtained by taking a 5 µL reaction aliquot and diluting to 1 mL with a 10% v/v solution of ethyl vinyl ether in DCM. Samples were shaken vigorously and allowed to stand for 10 minutes before GC analysis. All reactions were carried out in duplicate.

GC response factors were obtained for all starting materials and products using tridecane as an internal standard. Data was analysed as previously described in Ritter, T.; Hejl, A.; Wenzel, A. G.; Funk, T. W.; Grubbs, R. H. *Organometallics* 2006, 25, 5740.

Instrument conditions: inlet temperature: 250° C., detector temperature 300° C., H₂ flow: 30 mL/min, air flow: 400 mL/min, makeup flow: 30 mL/min.

GC method: 80° C. for 1.5 minutes, followed by a temperature increase of 40° C./min to 230° C. and held at that temperature for 2 minutes, then a temperature increase of 40° C./min to 300° C. and held at that temperature for 2.5 minutes. Total run time: 11.5 minutes. Table 7 shows the yield and the selectivity of the homodimerization reaction of allylbenzene at 0.01 mol % catalyst loadings.

TABLE 7

Homodimerization reaction of allylbenzene at 0.01 mol % catalyst loadings

| | 3 hours | | 6 hours | |
|---|---|---|---|---|
| Catalyst | Yield (%) | Z-selectivity (%) | Yield (%) | Z-selectivity (%) |
| Ru-17 | 48 | 97 | 58 | 95 |
| Ru-14 | 42 | 96 | 52 | 93 |
| Ru-21 | 69 | 95 | 72 | 91 |
| Ru-11 | 59 | 94 | 64 | 90 |
| Ru-9 | 50 | 94 | 59 | 84 |
| Ru-15 | 63 | 93 | 68 | 86 |
| Ru-20 | 66 | 92 | 72 | 85 |

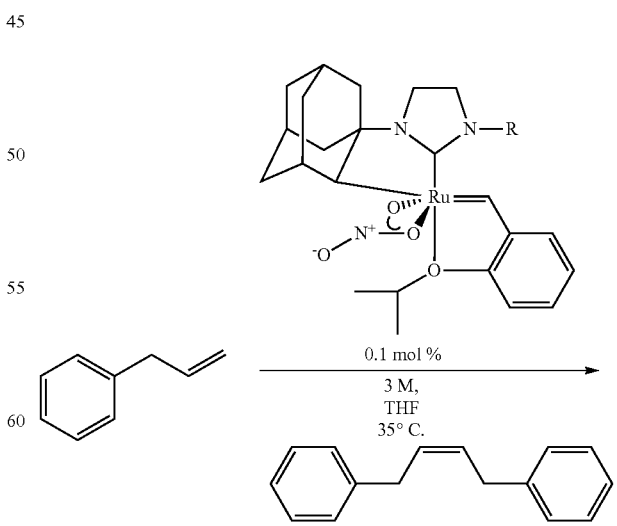

The same experiments were conducted at 0.1 mol % catalyst loading (3 M in THF), the results are shown in the Table 8. In this case, $^1$H-NMR spectra were analysed as previously described in Keitz, B. K.; Endo, K.; Herbert, M. B.; Grubbs, R. H. *J. Am. Chem. Soc.* 2011, 133, 9686, to determine conversion and Z-selectivity.

TABLE 8

| | Homodimerization reaction of allylbenzene at 0.1 mol % catalyst loadings | | | |
|---|---|---|---|---|
| R or | 3 hours | | 7 hours | |
| Catalyst | yield (%) | Z-selectivity (%) | yield (%) | Z-selectivity (%) |
| R = DIPP | 97 | 98 | 99 | 96 |
| Ru-17 | 91 | 97 | 96 | 94 |
| Ru-14 | 88 | 98 | 96 | 96 |
| Ru-21 | 90 | 92 | 96 | 82 |
| Ru-9 | 73 | 92 | 83 | 86 |
| R = Mes | 97 | 89 | 99 | 76 |
| Ru-15 | 93 | 92 | 97 | 81 |
| Ru-11 | 87 | 90 | 95 | 78 |

Screening-Scale Reactions
Reactivity with Allylic-Substituted Olefins

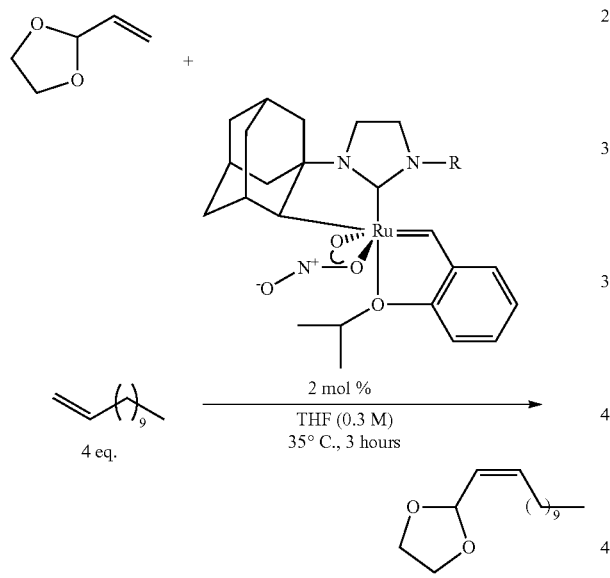

Typical procedure: CM of 2-vinyl-1,3-dioxolane and 1-dodecene

In a nitrogen-filled glovebox, 2-vinyl-1,3-dioxolane (16 μL, 0.16 mmol, 1 equiv.) and 1-dodecene (140 μL, 0.63 mmol, 4 equiv.) were combined in a 4 mL vial, to which tridecane (20 μL) was added as an internal standard. A solution of the appropriate catalyst (3.1 μmol, 2 mol %) in THF (350 μL) was added and the reaction was stirred open to the atmosphere at 35° C.

Samples for GC analysis were obtained by taking a 5 μL reaction aliquot and diluting to 1 mL with a 10% v/v solution of ethyl vinyl ether in DCM. Samples were shaken vigorously and allowed to stand for 10 minutes before GC analysis. All reactions were carried out in duplicate.

GC response factors were obtained for all starting materials and products using tridecane as an internal standard. Data was analysed as previously described in Ritter, T.; Hejl, A.; Wenzel, A. G.; Funk, T. W.; Grubbs, R. H. *Organometallics* 2006, 25, 5740.

Instrument conditions: inlet temperature: 250° C., detector temperature 300° C., H$_2$ flow: 30 mL/min, air flow: 400 mL/min, makeup flow: 30 mL/min.

GC method: 80° C. for 1.5 minutes, followed by a temperature increase of 40° C./min to 230° C. and held at that temperature for 2 minutes, then a temperature increase of 5° C./min to 245° C. and finally a temperature increase of 40° C./min to 300° C. and held at that temperature for 2.5 minutes. Total run time: 14.1 minutes. Table 9 shows the yields and the Z-selectivity in the CM of 2-vinyl-1,3-dioxolane and 1-dodecene.

TABLE 9

| | CM of 2-vinyl-1,3-dioxolane and 1-dodecene | | | |
|---|---|---|---|---|
| Catalyst | 3 hours | | 7 hours | |
| or R | Yield (%) | Z-selectivity (%) | Yield (%) | Z-selectivity (%) |
| Ru-11 | 43 | 67 | 52 | 64 |
| Ru-15 | 55 | 75 | 63 | 71 |
| R = Mes | 87 | 76 | n/a | n/a |
| R = DIPP | 94 | 94 | n/a | n/a |

Homodimerization of 4-Penten-1-ol

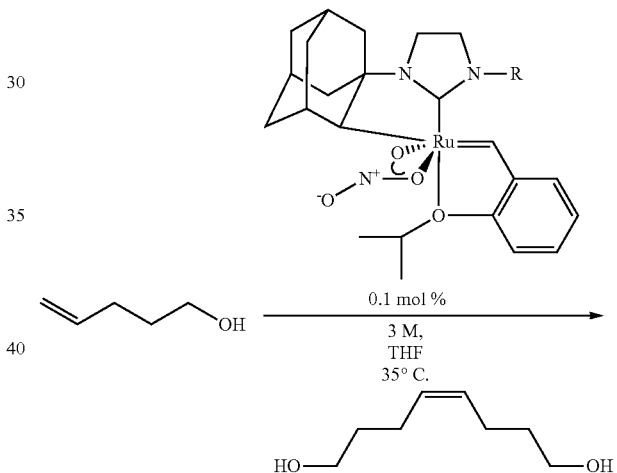

In a nitrogen-filled glovebox, 4-penten-1-ol (117 μL, 1.1 mmol, 1 equiv.) and THF (160 μL) were combined in a 4 mL vial, to which a solution of the appropriate catalyst (1.1 μmol, 0.1 mol %) in THF (100 μL) was added. The reaction was stirred open to the atmosphere at 35° C. $^1$H-NMR spectra were analysed as previously described in Keitz, B. K.; Endo, K.; Herbert, M. B.; Grubbs, R. H. *J. Am. Chem. Soc.* 2011, 133, 9686 to determine conversion and Z-selectivity. Table 10 shows the yields and the Z-selectivity in the homodimerization of 4-penten-1-ol

TABLE 10

| | Homodimerization of 4-penten-1-ol | | | |
|---|---|---|---|---|
| Catalyst | 3 hours | | 7 hours | |
| or R | Yield (%) | Z-selectivity (%) | Yield (%) | Z-selectivity (%) |
| R = Mes | 95 | 90 | 98 | 66 |
| R = DIPP | 96 | 98 | 98 | 83 |
| Ru-15 | 86 | 87 | 96 | 74 |

TABLE 10-continued

Homodimerization of 4-penten-1-ol

| Catalyst | 3 hours | | 7 hours | |
|---|---|---|---|---|
| or R | Yield (%) | Z-selectivity (%) | Yield (%) | Z-selectivity (%) |
| Ru-11 | 73 | 87 | 95 | 74 |
| Ru-17 | 31 | 94 | 87 | 89 |
| Ru-14 | 9 | 94 | 69 | 92 |
| Ru-21 | 92 | 86 | 98 | 66 |
| Ru-9 | 95 | 90 | 98 | 66 |
| Ru-20 | 86 | 87 | 96 | 74 |

Homodimerization of Methyl-10-Undecenoate

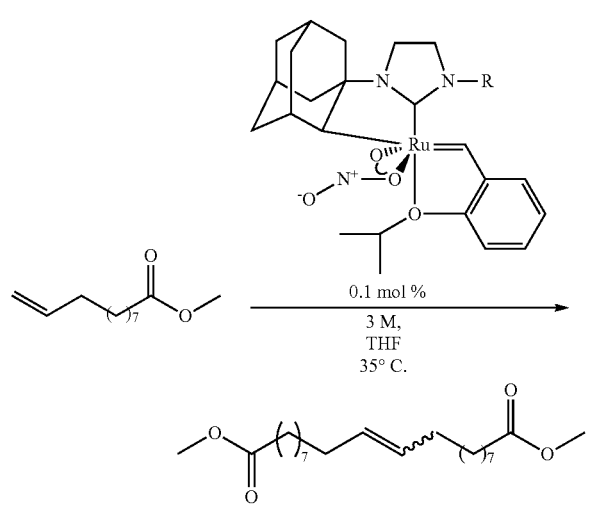

In a nitrogen-filled glovebox, methyl-10-undecenoate (130 μL, 0.57 mmol, 1 equiv.) and THF (10 μL) were combined in a 4 mL vial, to which a solution of the appropriate catalyst (0.57 μmol, 0.1 mol %) in THF (50 μL) was added. The reaction was stirred open to the atmosphere at 35° C. Samples for $^1$H-NMR analysis were obtained by taking a 5 μL reaction aliquot and diluting to 0.65 mL with a 5% v/v solution of ethyl vinyl ether in CDCl$_3$. $^1$H-NMR spectra were analysed as previously described in Keitz, B. K.; Endo, K.; Herbert, M. B.; Grubbs, R. H. *J. Am. Chem. Soc.* 2011, 133, 9686 to determine conversion and Z-selectivity. Table 11 shows the yields and Z-selectivities for the homodimerization of methyl-10-undecenoate.

TABLE 11

Homodimerization of methyl-10-undecenoate

| Catalyst | 3 hours | | 7 hours | |
|---|---|---|---|---|
| or R | Yield (%) | Z-selectivity (%) | Yield (%) | Z-selectivity (%) |
| R = Mes | 96 | 90 | 97 | 87 |
| R = DIPP | 98 | 96 | 98 | 97 |
| Ru-11 | 83 | 86 | 91 | 78 |
| Ru-15 | 91 | 88 | 93 | 82 |
| Ru-21 | 87 | 92 | 93 | 74 |
| Ru-9 | 96 | 90 | 97 | 87 |

General Procedure: CM of Vinylcyclohexane and Methyl 10-Undecenoate

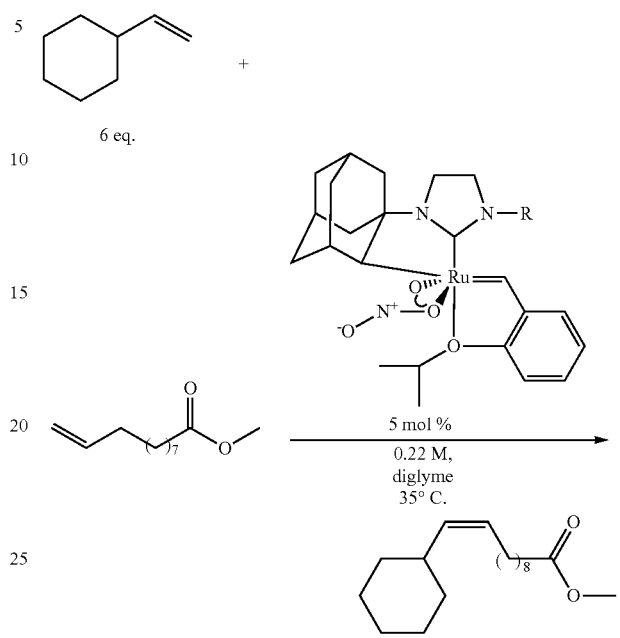

In a nitrogen-filled glovebox, vinylcyclohexane (73 μL, 0.53 mmol, 6 equiv.) and methyl 10-undecenoate (20 μL, 0.09 mmol, 1 equiv.) were combined in a 4 mL vial, to which tridecane (10 μL) was added as an internal standard. A solution of the appropriate catalyst (4.4 μmol, 5 mol %) in diglyme (300 μL) was added and the reaction was stirred open to the atmosphere at 35° C. Samples for GC analysis were obtained by taking a 5 μL reaction aliquot and diluting to 1 mL with a 10% v/v solution of ethyl vinyl ether in DCM. Samples were shaken vigorously and allowed to stand for 10 minutes before GC analysis.

GC response factors were obtained for all starting materials and products using tridecane as an internal standard. Data was analysed as previously described in Ritter, T.; Hejl, A.; Wenzel, A. G.; Funk, T. W.; Grubbs, R. H. *Organometallics* 2006, 25, 5740.

Instrument conditions: inlet temperature: 250° C., detector temperature 300° C., H$_2$ flow: 30 mL/min, air flow: 400 mL/min, makeup flow: 30 mL/min.

GC method: 80° C. for 2 minutes, followed by a temperature increase of 30° C./min to 250° C. and held at that temperature for 3 minutes, then a temperature increase of 5° C./min to 270° C. and finally a temperature increase of 30° C./min to 300° C. and held at that temperature for 3 minutes. Total run time: 18.7 minutes. Table 12 shows the yields and Z-selectivities during the CM of vinylcyclohexane and methyl 10-undecenoate reactions.

TABLE 12

CM of vinylcyclohexane and methyl 10-undecenoate

| Catalyst | 3 hours | | 6 hours | |
|---|---|---|---|---|
| | Yield (%) | Z-selectivity (%) | Yield (%) | Z-selectivity (%) |
| Ru-17 | 11 | 78 | 16 | 77 |
| Ru-14 | 13 | 77 | 18 | 76 |
| Ru-21 | 36 | 77 | 44 | 76 |

TABLE 12-continued

CM of vinylcyclohexane and methyl 10-undecenoate

| Catalyst | 3 hours | | 6 hours | |
|---|---|---|---|---|
| | Yield (%) | Z-selectivity (%) | Yield (%) | Z-selectivity (%) |
| Ru-11 | 41 | 55 | 49 | 54 |
| Ru-9 | 29 | 70 | 39 | 69 |
| Ru-15 | 39 | 70 | 46 | 69 |

What is claimed is:

1. An olefin metathesis catalyst complex, represented by Formula (VI),

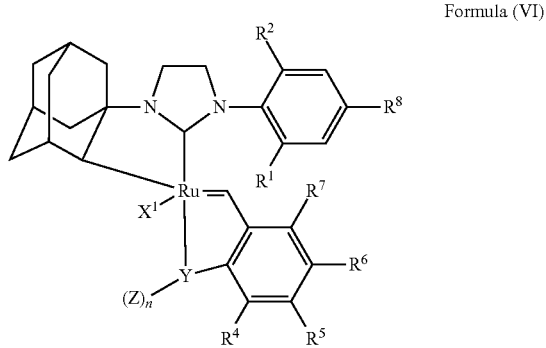

wherein:
- $R^1$ is $C_1$-$C_6$ alkyl, substituted $C_1$-$C_6$ alkyl, $C_5$-$C_8$ cycloalkyl, $C_5$-$C_8$ substituted cycloalkyl, $C_1$-$C_6$ alkoxy, or halide, where the substituents are selected from $C_1$-$C_6$ alkyl, $C_1$-$C_6$ alkoxy, or halide;
- $R^2$ is heteroatom-containing hydrocarbyl, or substituted heteroatom-containing hydrocarbyl, where the substituents are selected from $C_1$-$C_6$ alkyl, $C_1$-$C_6$ alkoxy, or halide;
- $R^8$ is selected from hydrogen, $C_2$-$C_{10}$ alkyl, substituted $C_1$-$C_{10}$ alkyl, $C_5$-$C_{10}$ aryl, substituted $C_5$-$C_{10}$ aryl, $C_5$-$C_{10}$ heteroaryl, substituted $C_5$-$C_{10}$ heteroaryl, halide (—Cl, —F, —Br, —I), hydroxyl, $C_1$-$C_6$ alkoxy, $C_5$-$C_{10}$ aryloxy, nitro (—NO$_2$), ester (—COOR$^9$), ketone (—COR$^9$), aldehyde (—COH), acyl (—COR$^9$), ester (—OCOR$^9$), carboxylic acid (—COOH), sulfonamide (—NR$^9$ SO$_2$Ar), carbamate (—NCO$_2$R$^9$), cyano (—CN), sulfoxide (—SOR$^9$), sulfonyl (—SO$_2$R$^9$), sulfonic acid (—SO$_3$H), fluoromethyl (—CF$_n$), fluroaryl (e.g., —C$_6$F$_5$, p-CF$_3$C$_6$H$_4$), where R$^9$ is hydrogen, methyl, $C_2$-$C_6$ alkyl, substituted $C_2$-$C_6$ alkyl, $C_5$-$C_{10}$ aryl, or substituted $C_5$-$C_{10}$ aryl, wherein n is 1, 2, or 3;
- $X^1$ is a bidentate anionic ligand, nitrate (NO$_3$$^-$), $C_1$-$C_{20}$ alkylcarboxylate, $C_6$-$C_{24}$ arylcarboxylate, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl;
- Y is a heteroatom selected from N, O, S, and P;
- $R^4$, $R^5$, $R^6$, and $R^7$ are each, independently, selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^4$, $R^5$, $R^6$, and $R^7$ can be linked to form one or more cyclic groups;
- n is 1 or 2; and
- Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and the olefin metathesis catalyst complex of Formula (VI) is not:

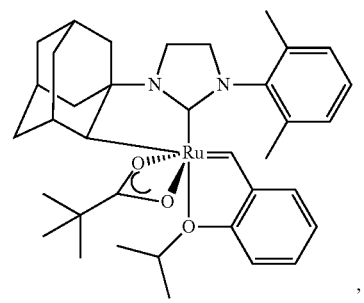

,

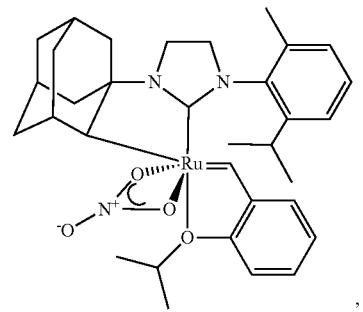

,

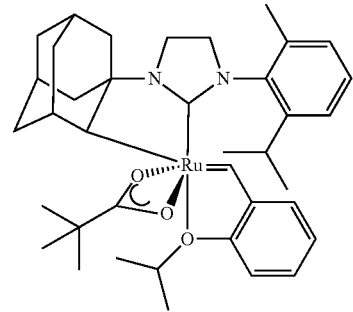

-continued

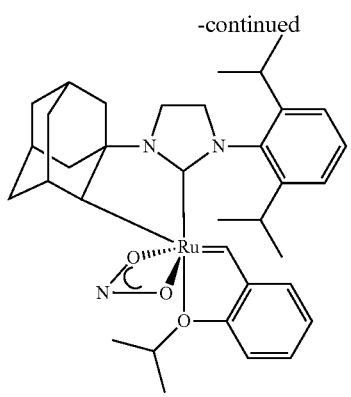

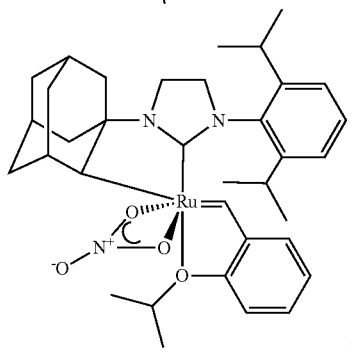

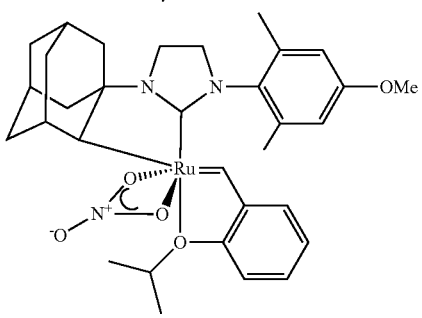

or

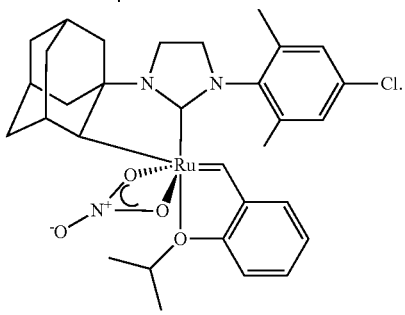

2. The olefin metathesis catalyst complex, according to claim 1, wherein:
R$^1$ is C$_1$-C$_6$ alkyl, C$_1$-C$_6$ alkoxy, or halide;
R$^2$ is C$_1$-C$_6$ alkoxy;
R$^4$, R$^5$, R$^6$, R$^7$ and R$^8$ are independently hydrogen;
Y is O;
Z is C$_1$-C$_6$ alkyl;
n is 1; and
X$^1$ is NO$_3^-$ or t-BuCO$_2$.

3. The olefin metathesis catalyst complex, according to claim 2, wherein:
R$^1$ is Me, OMe or F;
R$^2$ is MeO; and
Z is i-Pr.

4. The olefin metathesis catalyst complex, according to claim 2, wherein:
R$^1$ is Me, OMe, or F;
R$^2$ is MeO;
Z is i-Pr; and
X$^1$ is NO$_3^-$.

5. The olefin metathesis catalyst complex, according to claim 2, wherein:
R$^1$ is MeO, Me or F;
R$^2$ is MeO;
Z is i-Pr; and
X$^1$ is t-BuCO$_2$.

6. An olefin metathesis catalyst complex, selected from:

Ru-8
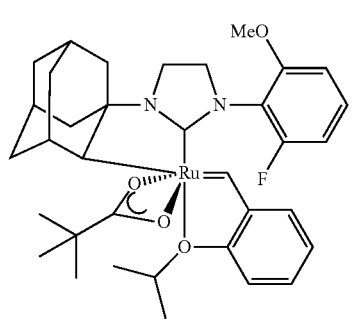

Ru-9
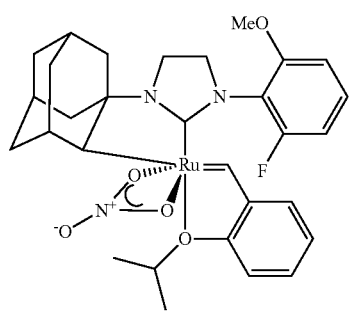

Ru-10
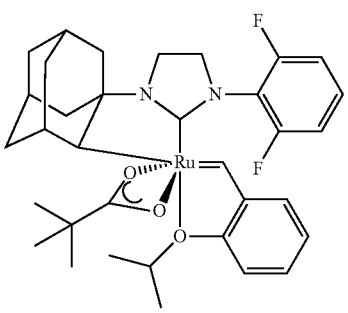

Ru-11
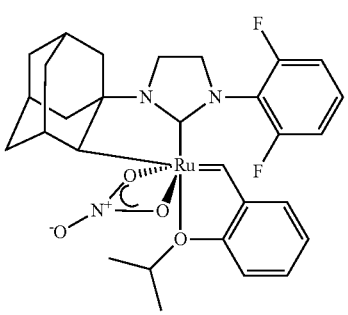

-continued
Ru-12
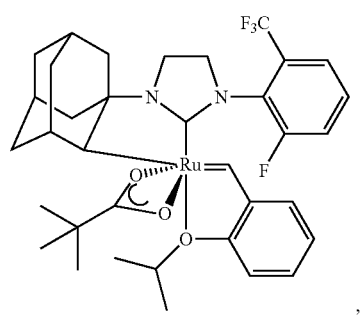
Ru-13
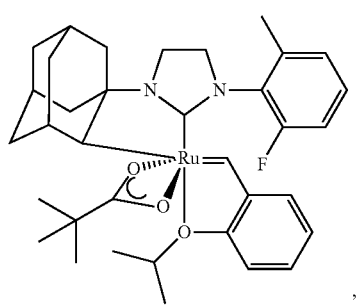
Ru-14
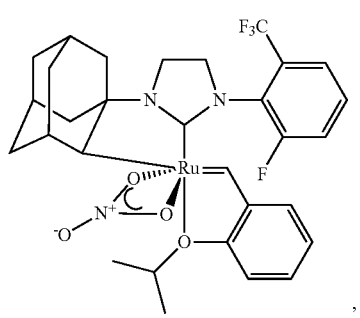
Ru-15
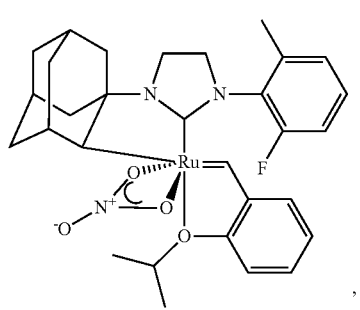
Ru-16
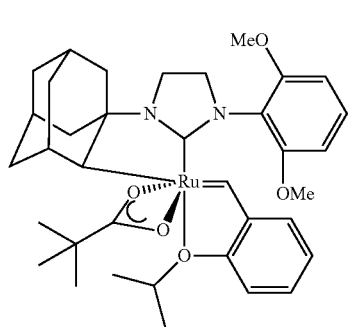
-continued
Ru-17
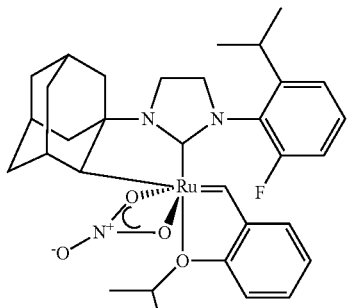
Ru-18
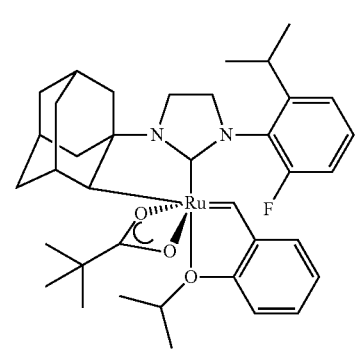
Ru-19
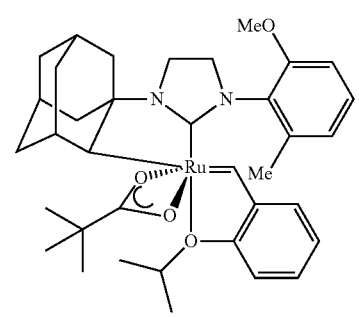
Ru-20
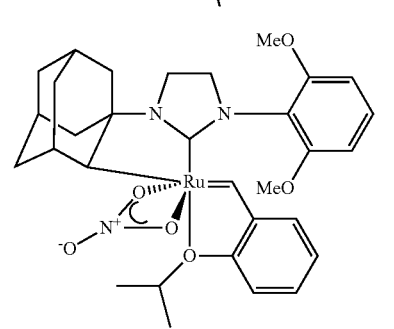
and
Ru-21
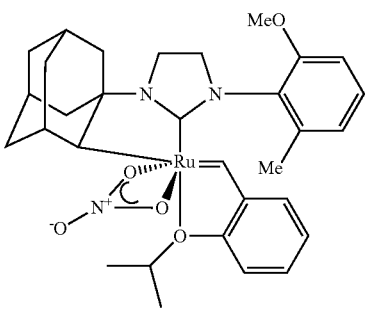
* * * * *